United States Patent
Feron et al.

(10) Patent No.: US 9,181,265 B2
(45) Date of Patent: Nov. 10, 2015

(54) SUBSTITUTED 2,3-DIHYDRO-1H-BENZO[A]PYRANO[2,3-C]PHENAZINES AS ANTI-ANGIOGENIC AND ANTI-CANCER AGENTS

(75) Inventors: Olivier Feron, Wezembeek-Oppem (BE); Olivier Riant, Brussels (BE); Robert Kiss, Sint Pieters-Leeuw (BE); Joelle Leclercq, Beaufays (BE); Gabrielle Chataigne, Lille (FR); Nicolas Vandelaer, Bossut-Gottechain (BE); Carole Lamy, Montigny le Bretonneux (FR)

(73) Assignees: UNIVERSITE CATHOLIQUE DE LOUVAIN, Louvain la Neuve (BE); UNIVERSITE LIBRE DE BRUXELLES, Brussels (BE)

( * ) Notice: Subject to any disclaimer, the term of this patent is extended or adjusted under 35 U.S.C. 154(b) by 0 days.

(21) Appl. No.: 13/997,576

(22) PCT Filed: Dec. 22, 2011

(86) PCT No.: PCT/EP2011/073825
§ 371 (c)(1),
(2), (4) Date: Jun. 24, 2013

(87) PCT Pub. No.: WO2012/085222
PCT Pub. Date: Jun. 28, 2012

(65) Prior Publication Data
US 2013/0289030 A1    Oct. 31, 2013

(30) Foreign Application Priority Data
Dec. 22, 2010  (EP) ..................... 10196652

(51) Int. Cl.
| | | |
|---|---|---|
| A61K 31/4985 | (2006.01) | |
| C07D 241/36 | (2006.01) | |
| C07D 491/052 | (2006.01) | |
| C07D 241/38 | (2006.01) | |
| C07D 491/048 | (2006.01) | |
| C07D 491/107 | (2006.01) | |
| C07D 491/153 | (2006.01) | |
| C07D 491/22 | (2006.01) | |
| C07D 497/04 | (2006.01) | |

(52) U.S. Cl.
CPC .......... *C07D 491/052* (2013.01); *C07D 241/38* (2013.01); *C07D 491/048* (2013.01); *C07D 491/107* (2013.01); *C07D 491/153* (2013.01); *C07D 491/22* (2013.01); *C07D 497/04* (2013.01)

(58) Field of Classification Search
CPC .......................... A61K 31/4985; C07D 241/36
USPC ........................................... 514/250; 544/342
See application file for complete search history.

(56) References Cited

FOREIGN PATENT DOCUMENTS

| JP | 2008 195749 | 8/2008 |
| WO | 2006/066923 | 6/2006 |
| WO | WO 2012/085222 | * 6/2012 |

OTHER PUBLICATIONS

Jordan, V. C. Nature Reviews: Drug Discovery, 2, 2003, 205.*
Vippagunta, et al. Advanced Drug Delivery Reviews, 48, 2001, 18.*
Baudelet et al., "The role of vessel maturation and vessel functionality in spontaneous fluctuations of T2*-weighted GRE signal within tumors", NMR in Biomedicine, 2006, vol. 19, pp. 69-76.
Baluk et al., "Cellular abnormalities of blood vessels as targets in cancer", Current Opinion in Genetics & Development, 2005, vol. 15, pp. 102-111.
Dewhirst, Mark W., "Intermittent Hypoxia Furthers the Rationale for Hypoxia-Inducible Factor-1 Targeting", Cancer Research, 2007, vol. 67, pp. 854-855.
Folkman, Judah, "Angiogenesis: an organizing principle for drug discovery?", Nature Reviews, Drug Discovery, 2007, vol. 6, pp. 273-286.
Hanahan et al., "Patterns and Emerging Mechanisms of the Angiogenic Switch during Tumorigenesis", Cell, 1996, vol. 86, pp. 353-364.
Martinive et al., "Reversal of temporal and spatial heterogeneities in tumor perfusion identifies the tumor vascular tone as a tunable variable to improve drug delivery", Mol. Cancer Ther., 2006, vol. 5, pp. 1620-1627.
Christofori, Gerhard, "New signals from the invasive front", Nature, 2006, vol. 441, pp. 444-450.
Dewhirst et al., "Cycling hypoxia and free radicals regulate angiogenesis and radiotherapy response", Nature Reviews, Cancer, 2008, vol. 8, pp. 425-437.
International Search Report dated Feb. 15, 2012 in corresponding PCT application.

* cited by examiner

*Primary Examiner* — Douglas M Willis
(74) *Attorney, Agent, or Firm* — Young & Thompson

(57) ABSTRACT

Novel phenazine derivatives of formula (I)

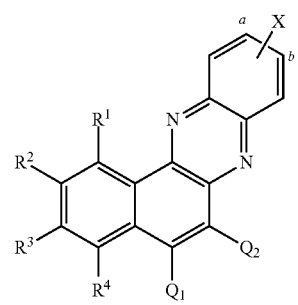

are disclosed. In particular, substituted 2,3-dihydro-1H-benzo[a]pyrano[2,3-c]phenazines are disclosed. The compounds can be used as anti-angiogenic and/or anti-tumor agents.

7 Claims, 1 Drawing Sheet

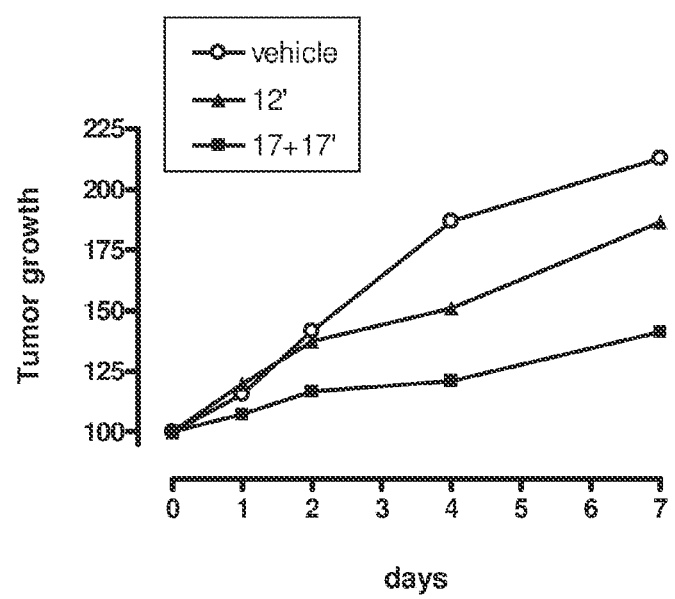

SUBSTITUTED 2,3-DIHYDRO-1H-BENZO[A]PYRANO[2,3-C]PHENAZINES AS ANTI-ANGIOGENIC AND ANTI-CANCER AGENTS

The present invention relates to novel phenazine derivatives including their pharmaceutically acceptable salts and solvates, which are useful as anti-angiogenic and/or anti-tumor agents, in particular under hypoxic conditions.

BACKGROUND OF THE INVENTION

Angiogenesis is a highly regulated process, whereby new blood vessels form from preexisting ones (Folkman J. *Angiogenesis: an organizing principle for drug discovery* Nat. Rev. Drug Discov. 2007; 6: 273-86). In adult mammals, physiologic angiogenesis is largely limited to the ovaries, uterus, and placenta, with the turnover rate of vascular endothelial cells being very low in most other tissues. Pathophysiologic angiogenesis is a characteristic of wound healing and diseased states, particularly cancer, where the number of proliferating endothelial cells increases significantly and the morphology of the vasculature is altered in multiple ways (Baluk P, Hashizume H, McDonald D M. *Cellular abnormalities of blood vessels as targets in cancer.* Curr. Opin. Genet. Dev. 2005; 15: 102-11). For many types of cancer, as tumor cells undergo dysregulated proliferation, the tumor mass initially expands beyond the support capacity of the existing vasculature, leading to decreased levels of oxygen and nutrients and the accumulation of metabolic wastes. Tumor cells respond to this deterioration of the tumor microenvironment by up-regulating several proangiogenic factors, including vascular endothelial growth factor (VEGF)-A, basic fibroblast growth factor, placental growth factor, and platelet-derived endothelial growth factor, which collectively activate quiescent endothelial cells and promote their migration into the tumor. This shift of the tumor microenvironment to an angiogenic state, or "angiogenic switch" (Hanahan D, Folkman J. *Patterns and emerging mechanisms of the angiogenic switch during tumorigenesis.* Cell 1996; 86: 353-64), is an important rate-limiting factor in tumor development. Despite the active angiogenesis induced by tumor cell-derived proangiogenic factors, structural defects associated with the tumor vasculature often lead to inefficient blood perfusion in established tumors, which contributes to tumor hypoxia. Tumor metastasis is also regulated by angiogenesis, as well as by lymphangiogenesis, where new lymphatic vessels are formed from preexisting ones (Christofori G. *New signals from the invasive front.* Nature 2006; 441: 444-50). Tumor cell dissemination, the first step in tumor metastasis, requires access to both blood and lymphatic circulation. Once successfully extravasated, the survival and further colonization of the disseminated tumor cells is dependent on angiogenesis at the secondary site. Angiogenesis is thus a key factor in the development and metastasis of a variety of tumor types and is an important hallmark of malignant disease. Moreover, angiogenesis presents unique opportunities for therapeutic intervention in cancer treatment, as first proposed by the late Judah Folkman more than thirty five years ago (Folkman J. *Tumor angiogenesis: therapeutic implications.* N Engl. J. Med. 1971; 285: 1182-6).

Today, inhibition of angiogenesis is recognized as new modality of cancer treatments. The targets of anti-angiogenic treatments are the proliferating/migrating endothelial cells into any tumor. Because this tumor-driven phenotype of endothelial cells differs from the quiescent endothelial cells lining blood vessels of healthy tissues, anti-angiogenic treatments were initially anticipated to be highly specific and thus safe drugs.

Recently, however, safety concerns were raised about anti-angiogenic drugs including anti-VEGF antibody (Avastin) and a variety of Tyrosine Kinase Inhibitors (Verheul and Pinedo., Nature Rev. Cancer, 7, 475-485 52007) (including bleeding, gastric perforation, hypertension and thrombotic events). The other biological roles played by angiogenic mediators or growth factors (such as VEGF) in maintaining the cardiovascular homeostasis are very likely to be the major cause of these life-threatening side effects.

Drugs with a higher selectivity for the tumor vasculature are therefore avidly needed.

Pathophysiologic hypoxia is actually recognized as a hallmark of most tumor types and documented to trigger angiogenesis. Even though angiogenesis aims at decreasing hypoxia, proliferating and migrating endothelial cells forming new vessels are per se exposed to low $pO_2$. In addition, two other forms of hypoxia directly impact endothelial cells in tumors. First, cyclic hypoxia arising from variations in red blood cell flux is reported to occur within tumor microvessels, thereby exposing at least intermittently tumor endothelial cells to a hypoxic environment (Martinive et al. Mol. Cancer Ther. 2006 June; 5(6):1620-7; Baudelet C. et al. NMR Biomed. 2006 February; 19(1): 69-76; Dewhirst et al. Nature Rev. Cancer 8, 425-437 (June 2008); Dewhirst Cancer Res. 2007 Feb. 1; 67(3): 854-5). Second, longitudinal hypoxia describes the $O_2$ gradient developing from the vessels supplying the tumor, i.e. the deeper the vessel penetrates in the tumor mass, the lesser oxygen is left available to diffuse in the surrounding tumor tissue.

As a summary, there is still a stringent need for potent tumor selective anti-angiogenic agents. Therefore a goal of the present invention is to satisfy this urgent need by identifying efficient pharmaceutically active compounds having tumor selective anti-angiogenic and/or cytotoxic activity.

SUMMARY OF THE INVENTION

After long and intensive research, the present inventors found a novel class of compounds that act as anti-angiogenic agents under hypoxic conditions and are thus useful to prevent or treat disorders associated with abnormal angiogenesis. The invention thus encompasses phenazine derivatives of general Formula I, their pharmaceutically acceptable salts and solvates as well as the use of such compounds or compositions comprising such compounds as anti-angiogenic agents, in particular under hypoxic conditions.

In a general aspect, the invention provides compounds of general formula I:

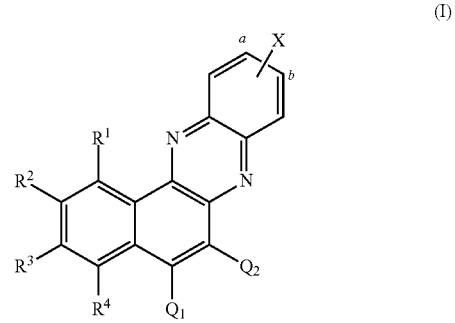

and pharmaceutically acceptable salts and solvates thereof, wherein

R$^1$ and R$^2$ are each, independently, H, halogen, hydroxyl, C1-C6 alkyl, C2-C6 alkenyl, C1-C6 alkoxy, C1-C6 alkoxycarbonyl, amino, alkylamino, dialkylamino, aryl, arylalkyl, heteroaryl, heterocyclyl, nitro, cyano, carboxy, or amide; or R$^1$ and R$^2$ are taken together to form together with the carbon atoms they are attached to a 5- or 6-membered cycloalkyl, 5- or 6-membered heterocyclyl, 5- or 6-membered aryl, or 5- or 6-membered heteroaryl, wherein said cycloalkyl, heterocyclyl, aryl or heteroaryl is optionally substituted with one or more C1-C4 alkyl group(s);

R$^3$ and R$^4$ are each, independently, H, halogen, hydroxyl, C1-C6 alkyl, C2-C6 alkenyl, C1-C6 alkoxy, C1-C6 alkoxycarbonyl, amino, alkylamino, aryl, arylalkyl, heteroaryl, heterocyclyl, nitro, cyano, carboxy, or amide;

X is either attached in position a or in position b and is selected from the group consisting of —COOR$^5$, —CONHR$^6$, —CONR$^6$R$^7$, —C(O)R$^8$, and —C(=NOH)R$^9$;

R$^5$ is C1-C6 alkyl, C2-C6 alkenyl, C2-C6 alkynyl, cycloalkyl, heterocyclyl, aryl, aralkyl or heteroaryl, wherein each of said cycloalkyl, heterocyclyl, aryl, aralkyl or heteroaryl groups is optionally substituted with one or more group(s) selected from the group consisting of C1-C4 alkyl, C1-C4 alkoxy and halogen;

R$^6$ is C1-C6 alkyl, C2-C6 alkenyl, C2-C6 alkynyl, cycloalkyl, heterocyclyl, aryl, aralkyl or heteroaryl, wherein each of said cycloalkyl, heterocyclyl, aryl, aralkyl or heteroaryl groups is optionally substituted with one or more group(s) selected from the group consisting of C1-C4 alkyl, C1-C4 alkoxy, halogen and hydroxy(C1-C4 alkyl);

R$^7$ is C1-C6 alkyl, C2-C6 alkenyl, C2-C6 alkynyl, cycloalkyl, heterocyclyl, aryl, aralkyl or heteroaryl, wherein each of said cycloalkyl, heterocyclyl, aryl, aralkyl or heteroaryl groups is optionally substituted with one or more group(s) selected from the group consisting of C1-C4 alkyl, C1-C4 alkoxy, hydroxyl, halogen and aryl; or R$^7$ is C1-C6 alkoxy; or R$^7$ is —CHR$^{10}$R$^{11}$, wherein R$^{10}$ is aryl or heteroaryl and R$^{11}$ is —C(O)NHR$^{12}$, wherein R$^{12}$ is C1-C6 alkyl or cycloalkyl; or R$^7$ and R$^6$ are taken together to form together with the nitrogen atom they are attached to a 5- or 6-membered cycloalkyl or a 5- or 6-membered heterocyclyl ring, the latter cycloalkyl or heterocyclyl rings being optionally substituted with one or more group(s) selected from the group consisting of C1-C4 alkyl, hydroxyl, aryl and aralkyl;

R$^8$ is C1-C6 alkyl, C2-C6 alkenyl, cycloalkyl, heterocyclyl, aryl, arylalkynyl or heteroaryl, wherein each of said cycloalkyl, heterocyclyl, aryl, arylalkynyl or heteroaryl groups is optionally substituted with one or more group(s) selected from the group consisting of halogen, C1-C6 haloalkyl, C1-C6 alkoxy, aryl-C1-C2 alkoxy optionally substituted by one or more group(s) selected from halogen, and C1-C4 alkylsulfonylamino;

R$^9$ is C1-C6 alkyl, C2-C6 alkenyl, cycloalkyl, heterocyclyl, aryl, arylalkynyl or heteroaryl, wherein each of the cycloalkyl, heterocycle, aryl, arylalkynyl or heteroaryl groups is optionally substituted with one or more group(s) selected from the group consisting of C1-C6 haloalkyl and C1-C6 alkoxy;

Q$^1$ and Q$^2$ are taken together to form a 5-, 6- or 7-membered unsaturated heterocyclyl together with the carbon atoms they are attached to, said heterocyclyl being unsubstituted or substituted with one or more Z$^1$; each Z$^1$ being independently selected from C1-C6 alkyl, C1-C6 alkenyl, hydroxyl, halogen, alkoxy, amino, alkylamino, dialkylamino, nitro, cyano, carboxy, or amide, or two Z$^1$ are taken together to form a 5-, 6- or 7-membered saturated or unsaturated ring together with the atom(s) they are attached to, said 5-, 6- or 7-membered saturated or unsaturated rings being optionally substituted with one or more Z$^2$, each Z$^2$ being independently selected from C1-C6 alkyl, C1-C6 alkenyl, hydroxyl, halogen, alkoxy, amino, alkylamino, dialkylamino, nitro, cyano, carboxy, or amide, or two Z$^2$ are taken together to form a 4-, 5-, 6- or 7-membered saturated or unsaturated ring together with the atoms they are attached to; said 4-, 5-, 6- or 7-membered saturated or unsaturated ring being optionally substituted by one or more further substituent(s) selected from alkyl, halo, nitro, or two of these further substituents form a methylenedioxygroup optionally substituted by one or two methyl group(s); or Q$^1$ is alkyl, alkenyl, aryl, heteroaryl, arylalkyl, alkoxy, or amino, and Q$^2$ is H; or Q$^1$ and Q$^2$ are both H;

with the proviso that the compound of general formula I is not a compound of formula II

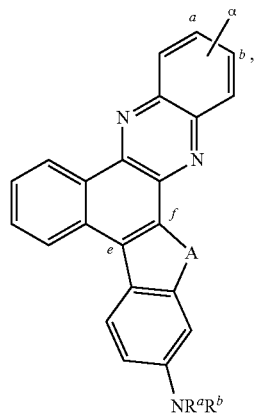

(II)

wherein

α is —COOR$^d$, wherein R$^d$ is alkyl, and is either attached in position a or in position b;

A is O, S or NR$^c$, wherein R$^c$ is H or C1-C10 alkyl; and

R$^a$ and R$^b$ are independently selected from H and C1-C10 alkyl.

In another aspect, the present invention provides a pharmaceutical composition comprising at least one compound according to the invention or a pharmaceutically acceptable salt or solvate thereof and at least one pharmaceutically acceptable carrier, diluent, excipient and/or adjuvant.

The invention also relates to the use of the above compounds or their pharmaceutically acceptable salts and solvates as anti-angiogenic agents and/or cancer cell cytotoxic agents, in particular under hypoxic conditions.

The invention also relates to the above compounds or their pharmaceutically acceptable salts and solvates for use as medicament for treating cancer and/or angiogenic disorders.

The invention further provides methods of treatment of cancer and/or angiogenic disorders comprising the administration of a therapeutically effective amount of a compound or pharmaceutically acceptable salt or solvate of the invention, to a patient in need thereof. Preferably the patient is a mammal, more preferably a human.

The invention also provides the use of a compound of formula (I) or a pharmaceutically acceptable salt or solvate thereof as a medicament. Preferably, the medicament is used for the treatment of cancer and/or angiogenic disorders.

DETAILED DESCRIPTION OF THE INVENTION

As noted above, the invention relates to compounds of formula I, as well as their pharmaceutically acceptable salts and solvates.

Preferred compounds of formula I and pharmaceutically acceptable salts and solvates thereof are those wherein $R^1$, $R^2$, $R^3$, and $R^4$ are independently selected from H, halo, hydroxyl, unsubstituted C1-C6 alkyl, unsubstituted C1-C6 alkoxy; or $R^3$ and $R^4$ are H, and $R^1$ and $R^2$ are taken together to form together with the carbon atoms they are attached to a 5- or 6-membered cycloalkyl, 5- or 6-membered heterocyclyl ring, wherein said cycloalkyl or heterocyclyl rings are optionally substituted with one or more C1-C4 alkyl group(s), preferably $R^1$, $R^2$, $R^3$ and $R^4$ are H; or $R^3$ and $R^4$ are H, and $R^1$ and $R^2$ are taken together to form together with the carbon atoms they are attached to a cyclohexyl optionally substituted with one or more C1-C2 alkyl preferably methyl group(s), more preferably, R', $R^2$, $R^3$ and $R^4$ are H; or $R^3$ and $R^4$ are each H, and $R^1$ and $R^2$ are taken together to form together with the carbon atoms they are attached to the following group:

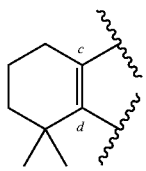

wherein c and d are the $R^1$ and $R^2$ attachment points respectively; and/or

X is either attached in position a or in position b and is selected from the group consisting of —COOR⁵, —CONHR⁶, —CONR⁶R⁷, —C(O)R⁸, and —C(=NOH)R⁹; wherein $R^5$ is selected from C1-C4 alkyl, preferably $R^5$ is methyl or ethyl, more preferably $R^5$ is methyl; and/or $R^6$, are each independently C1-C6 alkyl, cycloalkyl, aryl, aralkyl, heteroaryl, wherein each of said cycloalkyl, aryl, aralkyl, heteroaryl groups is optionally substituted with one or more group(s) selected from C1-C2 alkyl, C1-C4 alkoxy, halogen and hydroxy(C1-C2 alkyl), preferably with one or two group(s) selected from methyl, methoxy or hydroxymethyl, preferably $R^6$ is selected from methyl, cyclohexyl, benzyl optionally substituted with one or two methoxy, phenethyl, napht-1-ylmethyl, 1-phenyl-3-hydroxy-propan-2-yl preferably (S)-1-phenyl-3-hydroxy-propan-2-yl or (R)-1-phenyl-3-hydroxy-propan-2-yl, benzothiazol-2-yl, benzimidazol-2-yl; and/or $R^7$ is C1-C2 alkoxy, preferably methoxy, or —CHR¹⁰⁻¹¹, wherein $R^{10}$ is 6-membered aryl or 6-membered heteroaryl and $R^{11}$ is —C(O)NHR¹², wherein $R^{12}$ is C1-C6 alkyl or cyclohexyl, or $R^7$ and $R^6$ are taken together to form together with the nitrogen atom they are attached to a 6-membered heterocyclyl ring optionally substituted a C1-C4 alkyl, hydroxyl, 6-membered aryl or 6-membered aralkyl, preferably $R^7$ is methoxy, or —CHR¹⁰R¹¹, wherein $R^{10}$ is phenyl and $R^{11}$ is —C(O)NHR¹², wherein $R^{12}$ is tert-butyl or cyclohexyl, or $R^7$ and $R^6$ are taken together to form together with the nitrogen atom they are attached to a morpholin-4-yl, 4-hydroxypiperidin-1-yl, 4-methylpiperazin-1-yl, 4-phenylpiperazin-1-yl or 4-benzylpiperazin-1-yl group, more preferably $R^7$ and $R^6$ are taken together to form together with the nitrogen atom they are attached to a morpholin-4-yl, 4-hydroxypiperidin-1-yl, 4-methylpiperazin-1-yl, 4-phenylpiperazin-1-yl or 4-benzylpiperazin-1-yl group; or $R^7$ is:

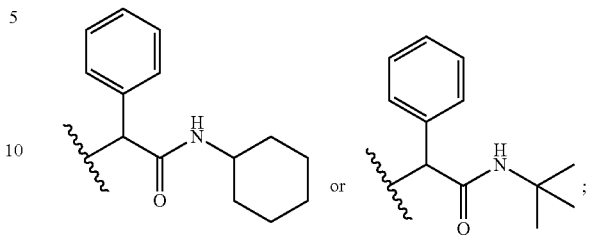

and/or $R^8$ is 6-membered aryl, 6-membered arylalkinyl or heteroaryl, wherein each of said groups is optionally substituted with one or more group(s) selected from the group consisting of halogen, C1-C2 haloalkyl, C1-C2 alkoxy, C1-C2 alkylsulfonylamino, phenyl-C1-C2 alkoxy, said phenyl-C1-C2 alkoxy group being optionally substituted by halogen, preferably $R^8$ is phenyl optionally substituted by one fluoro, chloro, $CF_3$, methoxy, methylsulfonylamino or benzyloxy group, said benzyloxy group being optionally substituted by one halogen, preferably fluoro, on the phenyl ring, phenylethynyl, pyridin-2-yl, furan-3-yl or benzothiophen-2-yl; and/or $R^9$ is phenyl;

preferably X is C(O)R⁸, wherein $R^8$ is defined as above; and/or $Q^1$ and $Q^2$ are taken together to form a 5-, 6- or 7-membered unsaturated O-, or O- and S-containing, preferably O-containing heterocyle together with the carbon atoms they are attached to, said heterocycle being optionally substituted with one or two $Z^1$; each $Z^1$ being independently selected from C1-C2 alkyl, C2-C6 alkenyl, hydroxyl, halogen, alkoxy, or two $Z^1$ are taken together to form a 6-membered saturated or unsaturated ring together with the atom(s) they are attached to, said 6-membered saturated or unsaturated ring being unsubstituted or substituted with one or two $Z^2$, each $Z^2$ being independently H, C1-C6 alkyl, or two $Z^2$ are taken together to form a 4-, 6-membered saturated or unsaturated ring together with the atoms they are attached to; the latter 4-, 6-membered ring being optionally substituted by one or more further substituent(s) selected from methyl, bromo, nitro, or two of these further substituents form a methylenedioxygroup substituted by two methyl groups; or $Q^1$ and $Q^2$ are both H, preferably $Q^1$ and $Q^2$ are taken together to form together with the carbon atoms they are attached to an unsaturated cyclic group selected from the group consisting of:

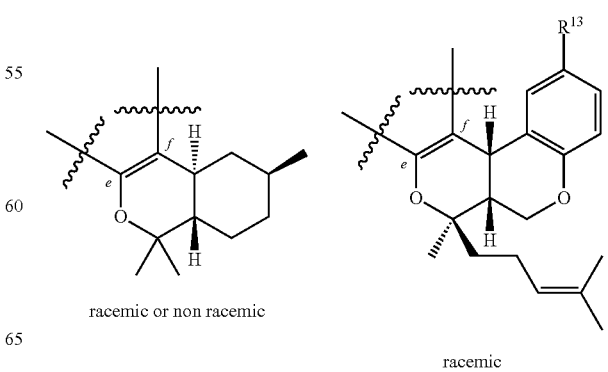

racemic or non racemic racemic

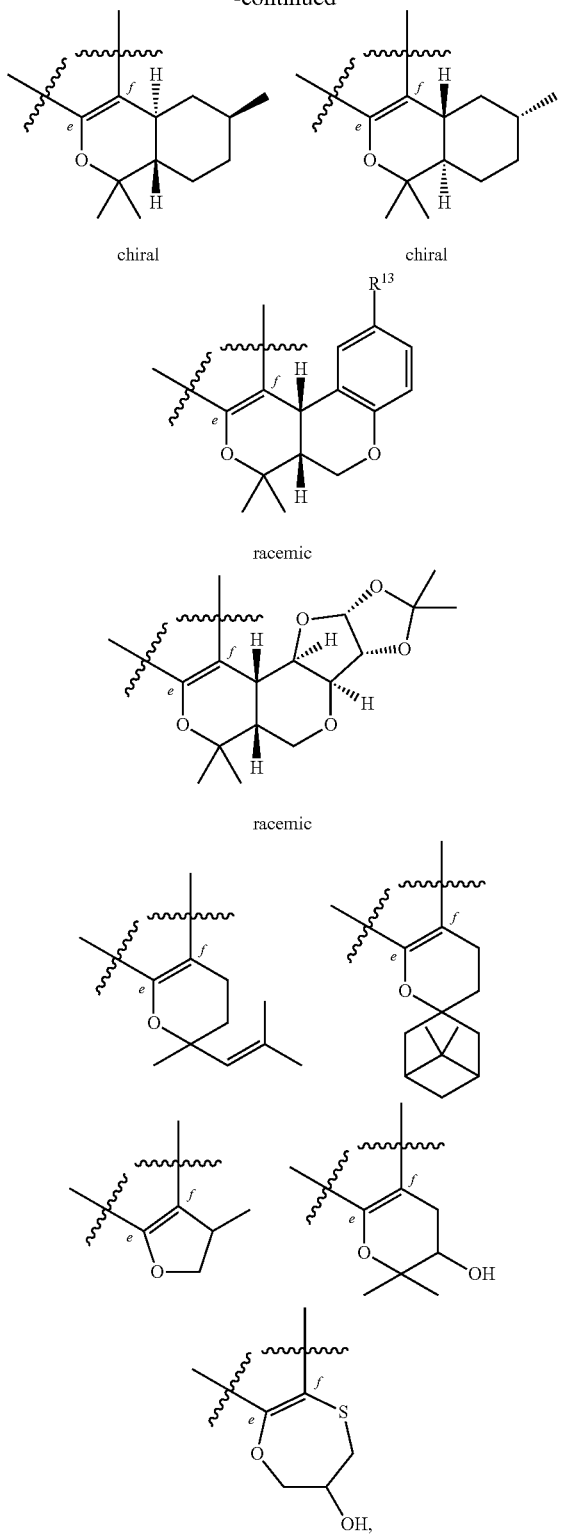

wherein R[13] is selected from H, nitro, and halogen, preferably from H, nitro and bromo, and wherein e and f are the $Q^1$ and $Q^2$ attachment points respectively; or $Q^1$ and $Q^2$ are taken together to form a 5-, 6- or 7-membered unsaturated heterocyclyl together with the carbon atoms they are attached to and $Q^1$ is attached to the carbon atom in position e via a heteroatom, said heterocyclyl being unsubstituted or substituted with one or more $Z^1$; each $Z^1$ being independently selected from C1-C6 alkyl, C1-C6 alkenyl, hydroxyl, halogen, alkoxy, amino, alkylamino, dialkylamino, nitro, cyano, carboxy, or amide, or two $Z^1$ are taken together to form a 5-, 6- or 7-membered saturated or unsaturated ring together with the atom(s) they are attached to, said 5-, 6- or 7-membered saturated or unsaturated rings being optionally substituted with one or more $Z^2$, each $Z^2$ being independently selected from C1-C6 alkyl, C1-C6 alkenyl, hydroxyl, halogen, alkoxy, amino, alkylamino, dialkylamino, nitro, cyano, carboxy, or amide, or two $Z^2$ are taken together to form a 4-, 5-, 6- or 7-membered saturated or unsaturated ring together with the atoms they are attached to; said 4, 5, 6 or 7-membered saturated or unsaturated ring being optionally substituted by one or more further substituent(s) selected from alkyl, halo, nitro, or two of these further substituents form a methylenedioxygroup optionally substituted by one or two methyl group(s); or $Q^1$ is alkyl, alkenyl, aryl, heteroaryl, arylalkyl, alkoxy, or amino, and $Q^2$ is H; or $Q^1$ and $Q^2$ are both H; preferably $Q^1$ and $Q^2$ are taken together to form a 5-, 6- or 7-membered unsaturated O-, or O- and S-containing, preferably O-containing heterocyle together with the carbon atoms they are attached to and $Q^1$ is attached to the carbon atom in position e via an O or S-, preferably O-atom, said heterocycle being optionally substituted with one or two $Z^1$; each $Z^1$ being independently selected from C1-C2 alkyl, C2-C6 alkenyl, hydroxyl, halogen, alkoxy, or two $Z^1$ are taken together to form a 6-membered saturated or unsaturated ring together with the atom(s) they are attached to, said 6-membered saturated or unsaturated ring being unsubstituted or substituted with one or two $Z^2$, each $Z^2$ being independently H, C1-C6 alkyl, or two $Z^2$ are taken together to form a 4-, 6-membered saturated or unsaturated ring together with the atoms they are attached to; the latter 4-, 6-membered ring being optionally substituted by one or more further substituent(s) selected from methyl, bromo, nitro, or two of these further substituents form a methylenedioxygroup substituted by two methyl groups; or $Q^1$ and $Q^2$ are both H; more preferably $Q^1$ and $Q^2$ are taken together to form together with the carbon atoms they are attached to an unsaturated cyclic group selected from the group consisting of:

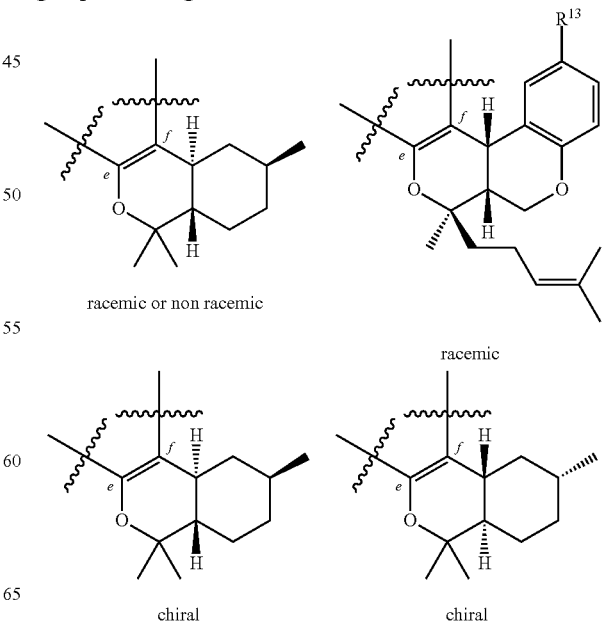

-continued

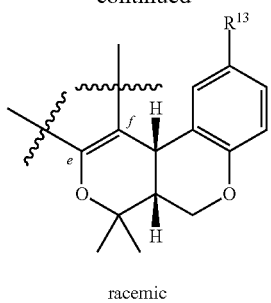

racemic

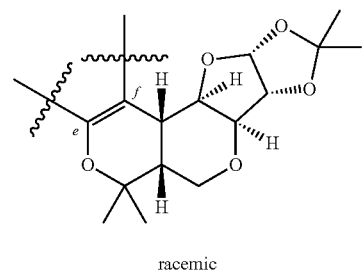

racemic

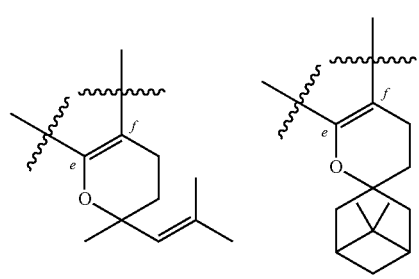

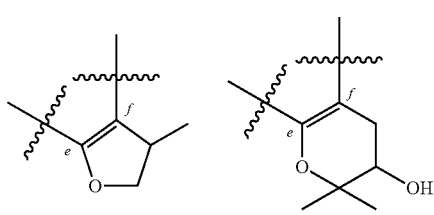

-continued

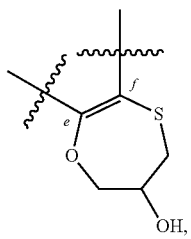

wherein $R^{13}$ is selected from H, nitro, and halogen, preferably from H, nitro and bromo, and wherein e and f are the $Q^1$ and $Q^2$ attachment points respectively.

In one particular embodiment, compounds of Formula I are those of formula Ia as well as their pharmaceutically acceptable salts and solvates:

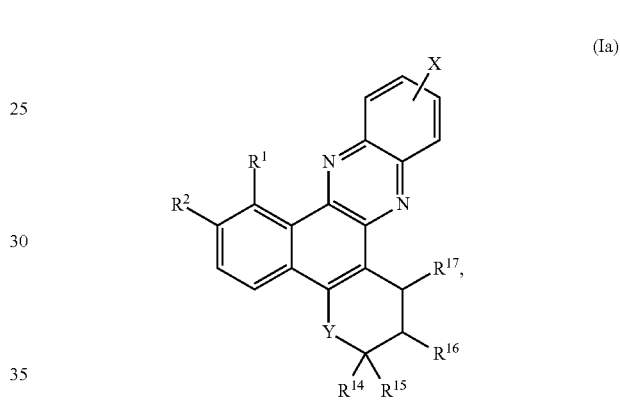

(Ia)

wherein X, $R^1$ and $R^2$ are as defined above in respect to formula I;

Y is S or O;

$R^{14}$ and $R^{15}$ are independently selected from H, C1-C4 alkyl, C2-C6 alkenyl, hydroxyl, halo, alkoxy, amino, alkylamino, nitro, cyano, carboxy, amide or $R^{14}$ and $R^{15}$ are taken together to form a 5-, 6- or 7-membered cycloalkyl ring together with the carbon atom they are attached to, said 5-, 6- or 7-membered cycloalkyl ring being unsubstituted or substituted with one or more $Z^2$, each $Z^2$ being independently selected from C1-C6 alkyl, C1-C6 alkenyl, hydroxyl, halogen, alkoxy, amino, alkylamino, nitro, cyano, carboxy, or amide, or two $Z^2$ are taken together to form a 4-, 5-, 6- or 7-membered cycloalkyl ring together with the atoms they are attached to, said 4-, 5-, 6- or 7-membered cycloalkyl ring being optionally substituted with one or two C1-C2 alkyl groups, preferably with two methyl groups, preferably $R^{14}$ and $R^{15}$ are independently selected from H, C1-C4 alkyl, C2-C6 alkenyl or are taken together to form a 5-, 6- or 7-membered cycloalkyl ring together with the carbon atom they are attached to, said 5-, 6- or 7-membered cycloalkyl ring being unsubstituted or substituted with one or more $Z^2$, each $Z^2$ being independently selected from C1-C6 alkyl, C1-C6 alkenyl, hydroxyl, halogen, alkoxy, amino, alkylamino, dialkylamino, nitro, cyano, carboxy, or amide, or two $Z^2$ are taken together to form a 4-, 5-, 6- or 7-membered cycloalkyl ring together with the atoms they are attached to, said 4-, 5-, 6- or 7-membered cycloalkyl ring being optionally substituted with one or two C1-C2 alkyl groups, preferably with two methyl groups more preferably $R^{14}$ and $R^{15}$ are independently selected from H, C1-C2 alkyl preferably methyl, C4-C6 alkenyl preferably 4-methylpent-3-en-1-yl, 2-methylprop-2-en-1-yl or are taken together to form a cyclohexyl ring together with the carbon atom they are attached to, said cyclohexyl ring being unsubstituted or substituted with one or more $Z^2$, each $Z^2$ being independently selected from C1-C2 alkyl preferably methyl, or two $Z^2$ are taken together to form a cyclobutyl ring together with the atoms they are attached to, said cyclobutyl ring being optionally substituted with one or two methyl groups;

$R^{16}$ and $R^{17}$ are independently selected from H, C1-C4 alkyl, C2-C6 alkenyl, hydroxy or $R^{16}$ and $R^{17}$ are taken together to form a 5-, 6- or 7-membered cycloalkyl or a 5-, 6- or 7-membered O- or O- and S-containing heterocyclyl ring together with the carbon atom they are attached to, said cycloalkyl or heterocycle being unsubstituted or substituted with one or more $Z^2$, each $Z^2$ being independently selected from C1-C6 alkyl, C2-C6 alkenyl, hydroxyl, halogen, alkoxy, amino, alkylamino, dialkylamino, nitro, cyano, carboxy, or amide, or two $Z^2$ are taken together to form 5-, 6- or 7-membered aryl or 5-, 6- or 7-membered O-, or O- and S-containing heterocycle together with the carbon atoms they are attached to, said aryl or heterocycle being optionally further substituted with one or two C1-C2 alkyl, bromo, nitro group(s) or two of these further substituents are taken together to form a methylenedioxygroup optionally substituted with one or two methyl groups, preferably $R^{16}$ is H and $R^{17}$ is H or OH; or $R^{16}$ and $R^{17}$ are taken together to form a cyclohexyl or 6-membered O-containing heterocyclyl preferably tetrahydropyranyl together with the carbon atom they are attached to, said cyclohexyl or heterocyclyl being substituted with one or more $Z^2$, each $Z^2$ being independently selected from H or C1-C2 alkyl, or two $Z^2$ are taken together to form a phenyl or a 5-membered O-containing heterocyclyl preferably tetrahydrofuranyl together with the carbon atoms they are attached to, said phenyl or heterocyclyl being optionally further substituted with one bromo or nitro group or two of these further substituents are taken together to form a methylenedioxygroup substituted with two methyl groups.

Preferred compounds of formula Ia are those wherein $R^1$ and $R^2$ are both H and Y is O; and/or Further preferred compounds of formula Ia are those wherein $R^1$ and $R^2$ are both H, Y is O, $R^{14}$ and $R^{15}$ are taken together to form a cyclohexyl ring together with the carbon atom they are attached to, said cyclohexyl ring being substituted with two $Z^2$ that are taken together to form a cyclobutyl together with the atoms they are attached to, said cyclobutyl ring being optionally substituted with one or two C1-C2 alkyl groups, preferably with two methyl groups; and $R^{16}$ and $R^{17}$ are H.

In one particular embodiment, compounds of Formula Ia are those of formulae Ia-1, Ia-1' or Ia-1" as well as their pharmaceutically acceptable salts and solvates:

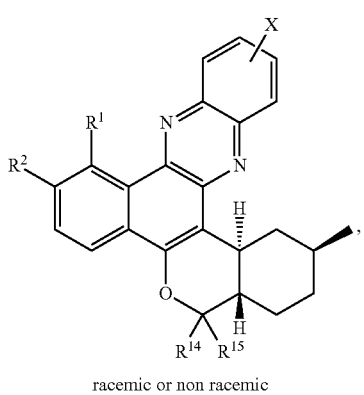

(Ia-1)

racemic or non racemic

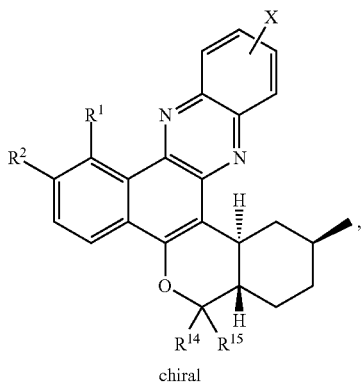

(Ia-1')

chiral

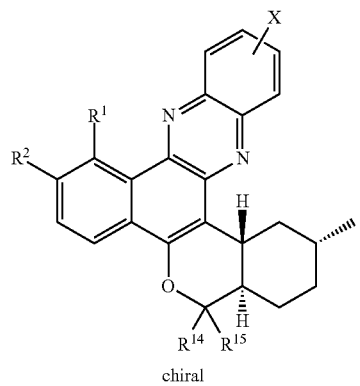

(Ia-1")

chiral wherein X, $R^1$, $R^2$, $R^{14}$ and $R^{15}$ are as defined above in respect to formula Ia.

In another particular embodiment, compounds of Formula Ia are those of Formula Ia-2 as well as their pharmaceutically acceptable salts and solvates:

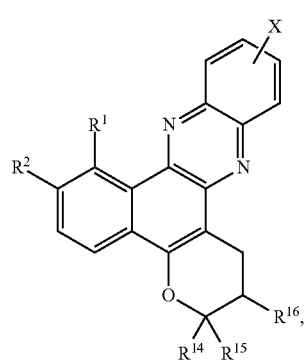

(Ia-2)

wherein X, $R^1$ and $R^2$ are as defined above in respect to formula Ia;

$R^{14}$ and $R^{15}$ are as defined above in respect to formula Ia, preferably $R^{14}$ and $R^{15}$ are independently selected from H, C1-C4 alkyl preferably methyl or C2-C6 alkenyl preferably 4-methylpent-3-en-1-yl, 2-methylprop-2-en-1-yl; and $R^{16}$ is as defined above in respect to formula Ia, preferably $R^{16}$ is selected from H, C1-C4 alkyl, C2-C6 alkenyl, and OH.

Preferred compounds of formula Ia-2 are those wherein $R^{16}$ is H or OH.

Further preferred compounds of formula Ia-2 are those wherein $R^{14}$ and $R^{15}$ are both methyl and $R^{16}$ is OH.

Other preferred compounds of formula Ia-2 are those wherein $R^{14}$ is methyl, $R^{15}$ is C2-C6 alkenyl preferably 4-methylpent-3-en-1-yl, 2-methylprop-2-en-1-yl and $R^{16}$ is H.

In another particular embodiment, compounds of Formula I are those of Formula Ib as well as their pharmaceutically acceptable salts and solvates:

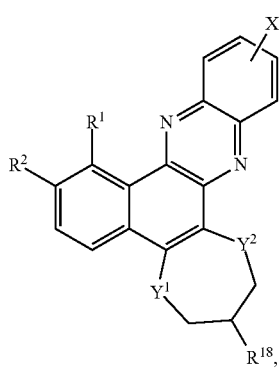
(Ib)

wherein X, $R^1$ and $R^2$ are as defined above in respect to formula I;

$Y^1$ and $Y^2$ are independently S or O, preferably one of $Y^1$ and $Y^2$ is O and the other one is S, more preferably $Y^1$ is O and $Y^2$ is S;

$R^{18}$ is selected from H, C1-C4 alkyl or OH, preferably $R^{18}$ is OH.

In another particular embodiment, compounds of Formula I are those of Formula Ic as well as their pharmaceutically acceptable salts and solvates:

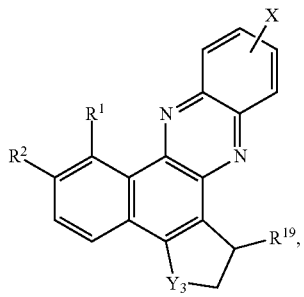
(Ic)

wherein X, $R^1$ and $R^2$ are as defined above in respect to formula I;

$Y^3$ is O or S, preferably O; and $R^{19}$ is selected from H, C1-C4 alkyl, C2-C6 alkenyl, and OH, preferably $R^{19}$ is H or methyl, more preferably $R^{19}$ is methyl.

In another particular embodiment, compounds of Formula I are those of Formula Id as well as their pharmaceutically acceptable salts and solvates:

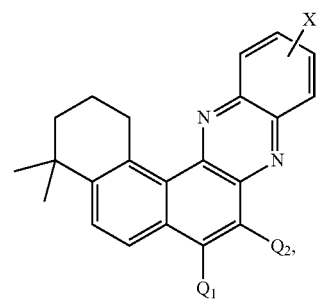
(Id)

wherein $Q^1$, $Q^2$ and X are defined as in respect to formula I.

In another particular embodiment, compounds of Formula I are those of Formulae Ie-1, Ie-2, Ie-3, Ie-4, Ie-5 and Ie-6 as well as their pharmaceutically acceptable salts and solvates:

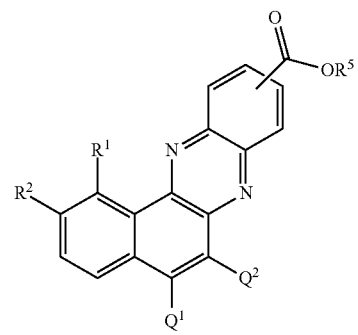
Ie-1

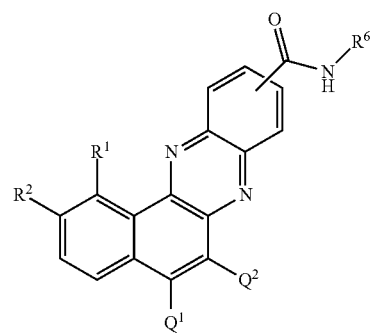
Ie-2

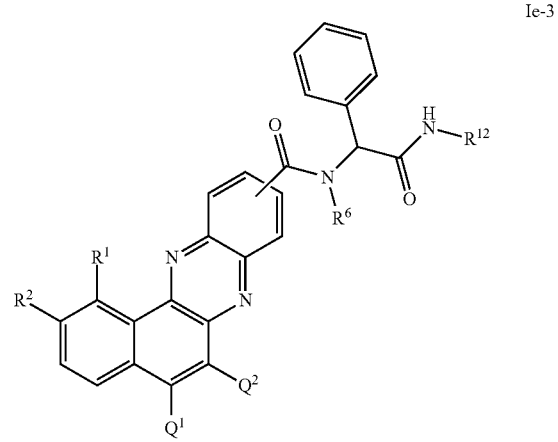
Ie-3

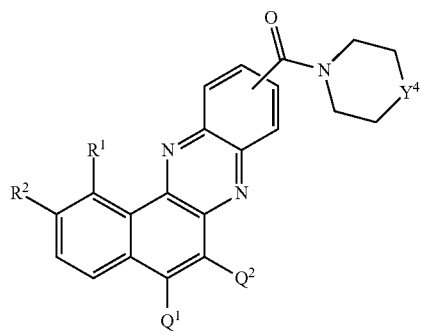

Ie-4

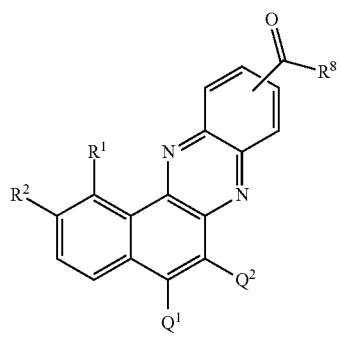

Ie-5

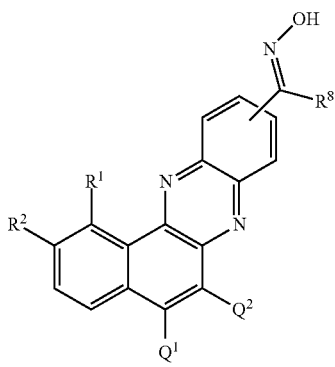

Ie-6 wherein $Q^1$, $Q^2$, $R^1$, $R^2$, $R^5$, $R^6$, $R^8$ $R^9$ and $R^{12}$ are defined as in respect to formula I;

$Y^4$ is O, S, —CHOH or N—$R^{20}$ wherein $R^{20}$ is C1-C6 alkyl, 6-membered aryl, 6-membered aralkyl preferably $Y^4$ is O, S, —CHOH or N—$R^{20}$ wherein $R^{20}$ is methyl, phenyl, benzyl.

Preferred compounds of Formulae Ie-1, Ie-2, Ie-3, Ie-4, Ie-5 and Ie-6 are those of formula Ie-5 as well as their pharmaceutically acceptable salts and solvates.

Particularly preferred compounds of the invention are those listed in Table 1 hereafter.

TABLE 1

| Compound n° | Structure |
|---|---|
| 1 racemic | |
| 1' racemic | |

TABLE 1-continued
| Compound n° | Structure |
|---|---|
| 2 | racemic 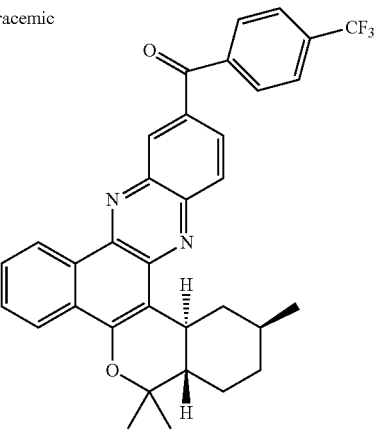 |
| 2' | racemic 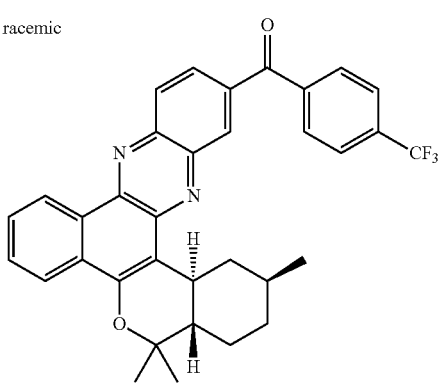 [SMILES: C[C@H]1CC[C@H]2[C@H](C1)c1c(c3ccccc3c3nc4ccc(C(=O)c5ccc(C(F)(F)F)cc5)cc4nc13)OC2(C)C] |
| 3 | racemic 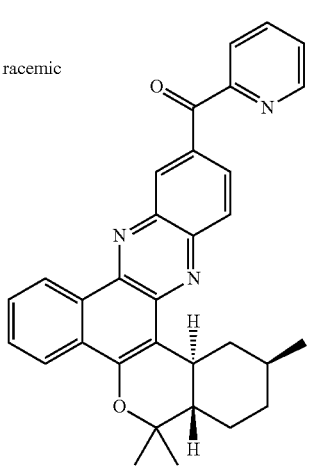 [SMILES: C[C@H]1CC[C@H]2[C@H](C1)c1c(c3ccccc3c3nc4cc(C(=O)c5ccccn5)ccc4nc13)OC2(C)C] |

TABLE 1-continued

| Compound n° | Structure |
|---|---|
| 3' | racemic |
| 5 | 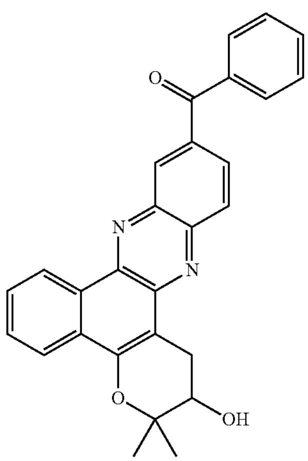 [SMILES: CC1(C)Oc2c(c3nc4ccc(C(=O)c5ccccc5)cc4nc3c3ccccc23)CC1O] |
| 5' | 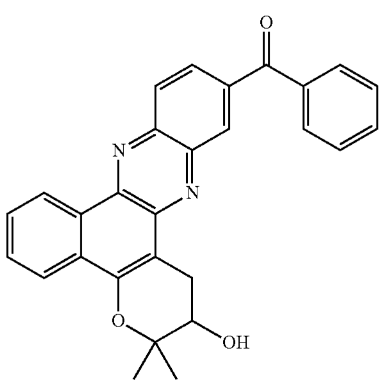 [SMILES: CC1(C)Oc2c(c3nc4cc(C(=O)c5ccccc5)ccc4nc3c3ccccc23)CC1O] |

TABLE 1-continued
| Compound n° | Structure |
|---|---|
| 7 | 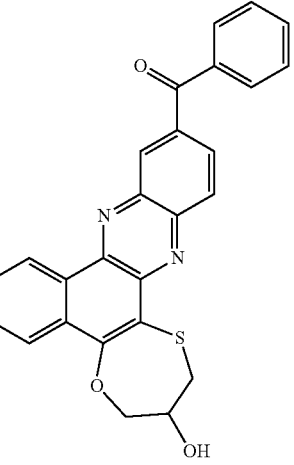 |
| 7' | 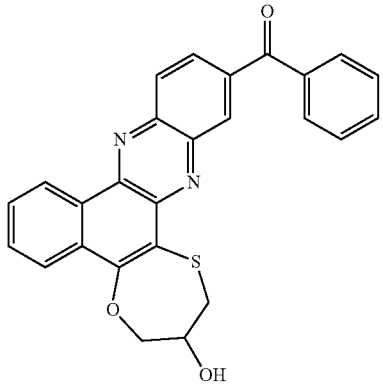 [SMILES: O=C(c1ccccc1)c1ccc2nc3c(nc2c1)c1c(c2ccccc23)OCC(O)CS1] |
| 9 | 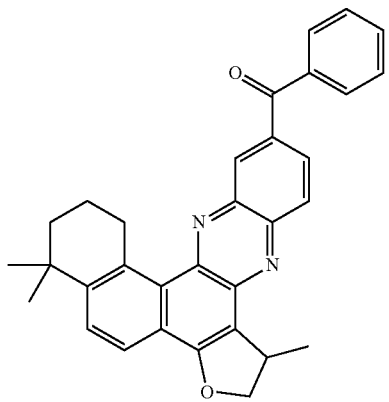 [SMILES: CC1COc2c1c1nc3ccc(C(=O)c4ccccc4)cc3nc1c1c3c(ccc21)C(C)(C)CCC3] |
| 9' | 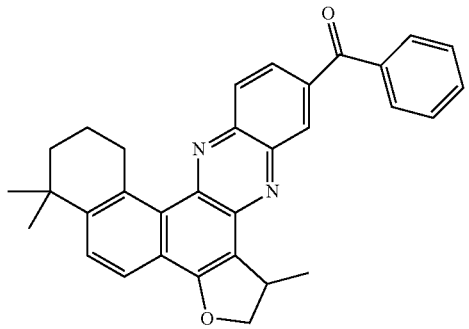 [SMILES: CC1COc2c1c1nc3cc(C(=O)c4ccccc4)ccc3nc1c1c3c(ccc21)C(C)(C)CCC3] |

TABLE 1-continued

| Compound n° | Structure |
|---|---|
| 11 | racemic |
| 11' | racemic |
| 12 | racemic |

TABLE 1-continued
| Compound n° | Structure |
|---|---|
| 12' racemic | 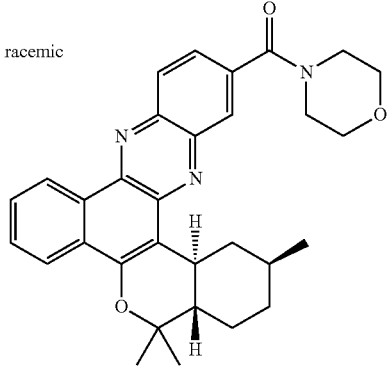 [SMILES: C[C@H]1CC[C@H]2[C@H](C1)c1c(c3ccccc3c3nc4ccc(C(=O)N5CCOCC5)cc4nc13)OC2(C)C] |
| (R)-12 chiral | 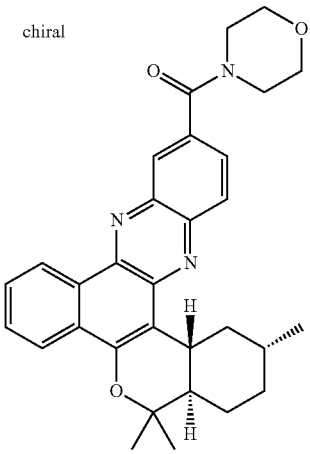 [SMILES: C[C@@H]1CC[C@@H]2[C@@H](C1)c1c(c3ccccc3c3nc4cc(C(=O)N5CCOCC5)ccc4nc13)OC2(C)C] |
| (R)-12' chiral | 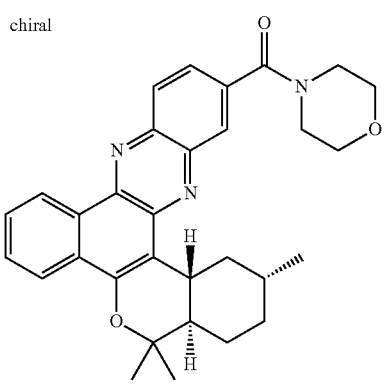 [SMILES: C[C@@H]1CC[C@@H]2[C@@H](C1)c1c(c3ccccc3c3nc4ccc(C(=O)N5CCOCC5)cc4nc13)OC2(C)C] |

TABLE 1-continued

| Compound n° | Structure |
|---|---|
| (S)-12 | chiral |
| (S)-12' | chiral |
| 14 | racemic |

TABLE 1-continued
| Compound n° | Structure |
|---|---|
| 14' racemic | 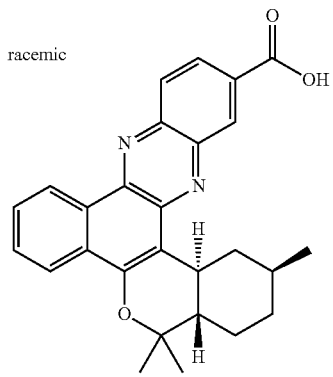 [SMILES: C[C@H]1CC[C@H]2[C@H](C1)c1c(c3ccccc3c3nc4ccc(C(=O)O)cc4nc13)OC2(C)C] |
| 16 racemic | 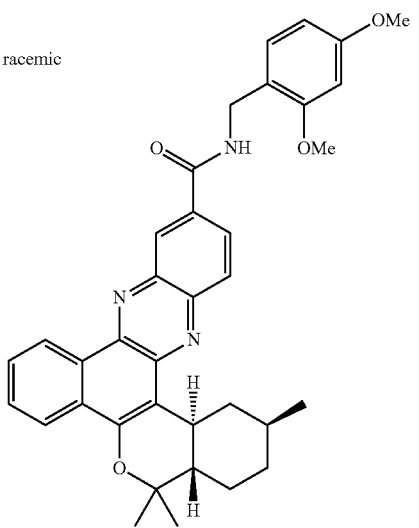 [SMILES: COc1ccc(CNC(=O)c2ccc3nc4c5c(c6ccccc6c4nc3c2)OC(C)(C)[C@H]2CC[C@H](C)C[C@H]52)c(OC)c1] |
| 16' racemic | 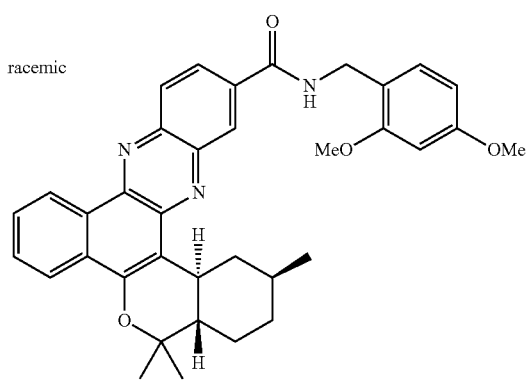 [SMILES: COc1ccc(CNC(=O)c2ccc3nc4c(nc3c2)c2c(c3ccccc34)OC(C)(C)[C@H]3CC[C@H](C)C[C@H]23)c(OC)c1] |

TABLE 1-continued
| Compound n° | Structure |
|---|---|
| (R)-16 | chiral 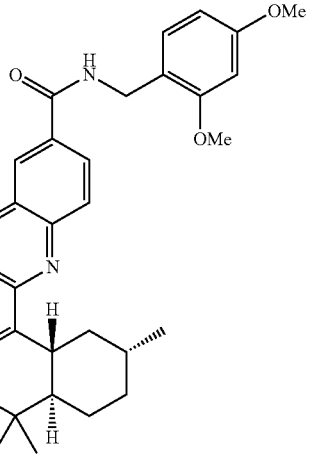 |
| (R)-16' | chiral 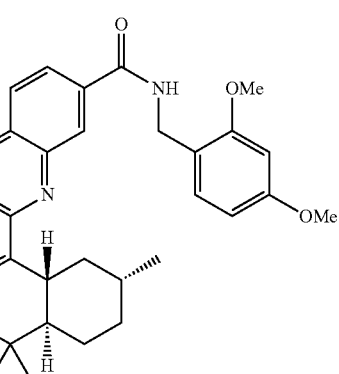 |
| (S)-16 | chiral 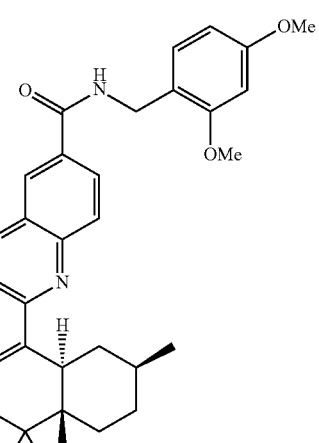 |

TABLE 1-continued

| Compound n° | Structure |
|---|---|
| (S)-16' | chiral |
| 17 | |
| 17' | |

TABLE 1-continued

| Compound n° | Structure |
|---|---|
| 18 | 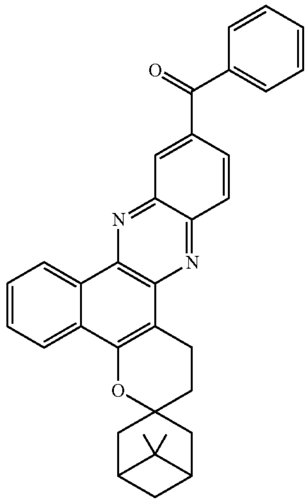 [SMILES: CC1(C)C2CC1CC1(CCc3c(c4ccccc4c4nc5cc(C(=O)c6ccccc6)ccc5nc34)O1)C2] |
| 18' | 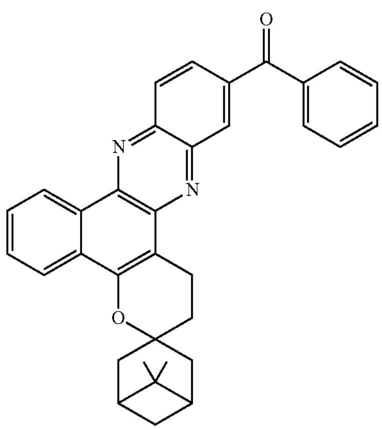 [SMILES: CC1(C)C2CC1CC1(CCc3c(c4ccccc4c4nc5ccc(C(=O)c6ccccc6)cc5nc34)O1)C2] |
| 19 | racemic |

TABLE 1-continued
| Compound n° | Structure |
|---|---|
| 19' racemic | 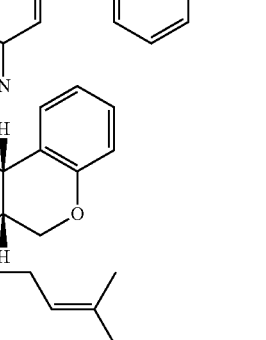 |
| 20 racemic | 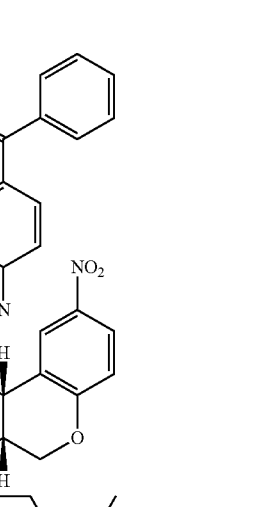 |
| 20' racemic | 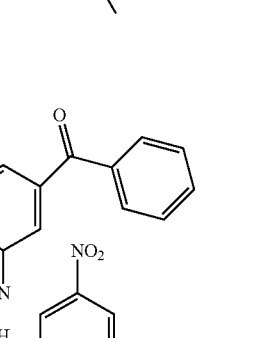 |

TABLE 1-continued
| Compound n° | Structure |
|---|---|
| 21 racemic | 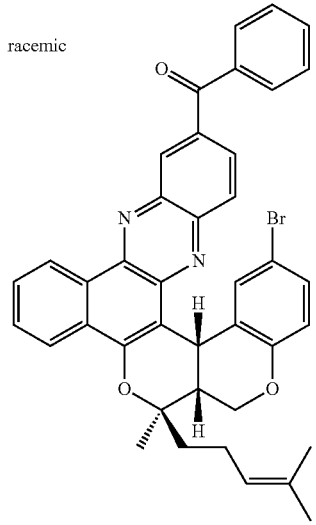 [SMILES: CC(C)=CCC[C@@]1(C)Oc2c(c3nc4ccc(C(=O)c5ccccc5)cc4nc3c3ccccc23)[C@@H]2c3cc(Br)ccc3OC[C@@H]21] |
| 21' racemic | 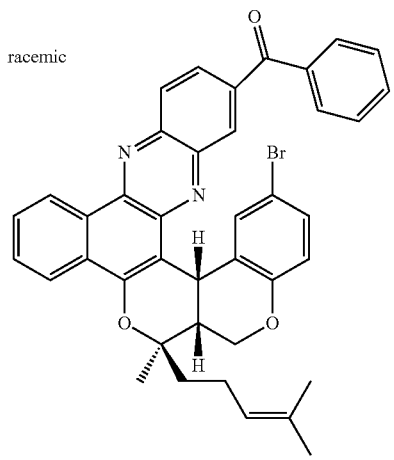 [SMILES: CC(C)=CCC[C@@]1(C)Oc2c(c3nc4cc(C(=O)c5ccccc5)ccc4nc3c3ccccc23)[C@@H]2c3cc(Br)ccc3OC[C@@H]21] |
| 22 racemic | 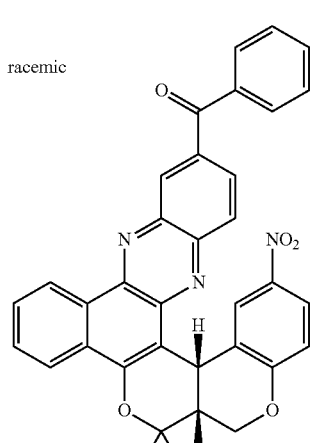 |

TABLE 1-continued
| Compound n° | Structure |
|---|---|
| 22' racemic | 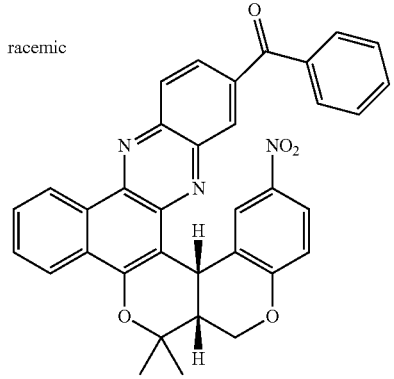 [SMILES: CC1(C)Oc2c(c3nc4cc(C(=O)c5ccccc5)ccc4nc3c3ccccc23)[C@@H]2c3cc([N+](=O)[O-])ccc3OC[C@@H]21] |
| 23 racemic | 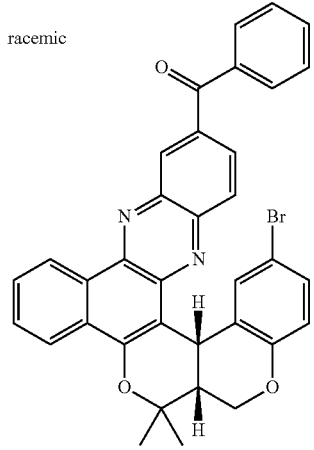 [SMILES: CC1(C)Oc2c(c3nc4ccc(C(=O)c5ccccc5)cc4nc3c3ccccc23)[C@@H]2c3cc(Br)ccc3OC[C@@H]21] |
| 23' racemic | 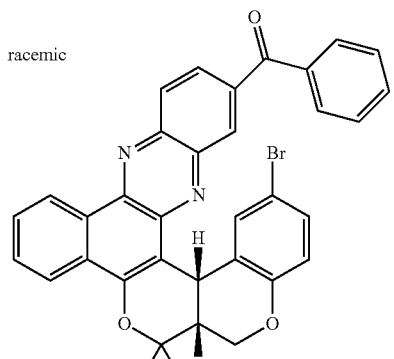 |

TABLE 1-continued
| Compound n° | Structure |
|---|---|
| 24 | racemic 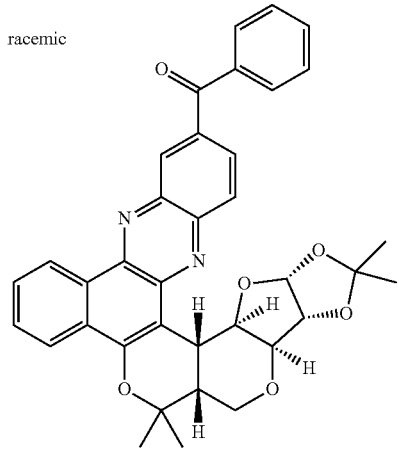 |
| 24' | racemic 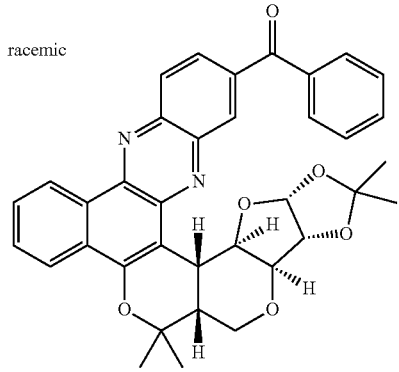 |
| 25 | 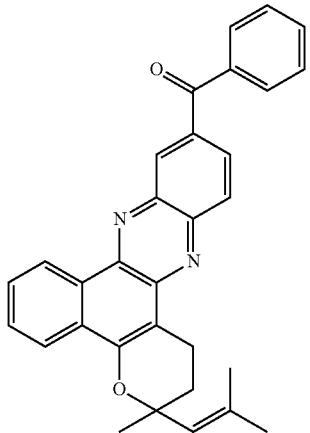 [SMILES: CC(C)=CC1(C)CCc2c(c3ccccc3c3nc4cc(C(=O)c5ccccc5)ccc4nc23)O1] |

TABLE 1-continued

| Compound n° | Structure |
|---|---|
| 25' | |
| 26 racemic | |
| 26' racemic | |

TABLE 1-continued
| Compound n° | Structure |
|---|---|
| 27 racemic | 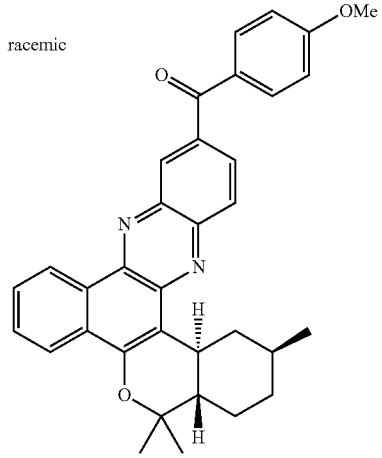 [SMILES: COc1ccc(C(=O)c2ccc3nc4c5c(c6ccccc6c4nc3c2)OC(C)(C)[C@H]2CC[C@H](C)C[C@H]52)cc1] |
| 27' racemic | 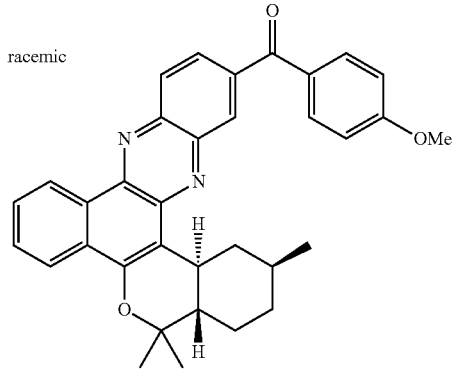 [SMILES: COc1ccc(C(=O)c2ccc3nc4c(nc3c2)c2c(c3ccccc34)OC(C)(C)[C@H]3CC[C@H](C)C[C@H]23)cc1] |
| 28 racemic | 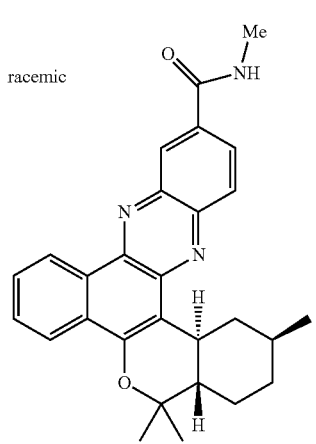 [SMILES: CNC(=O)c1ccc2nc3c4c(c5ccccc5c3nc2c1)OC(C)(C)[C@H]1CC[C@H](C)C[C@H]41] |

TABLE 1-continued
| Compound n° | Structure |
|---|---|
| 28' racemic | 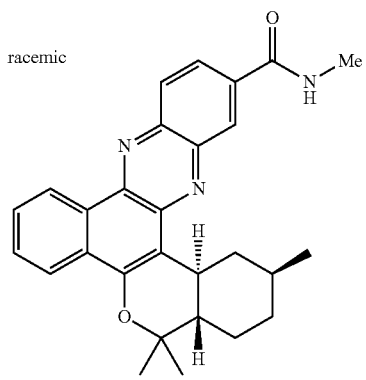 [SMILES: CNC(=O)c1ccc2nc3c(nc2c1)c1c(c2ccccc23)OC(C)(C)[C@H]2CC[C@H](C)C[C@H]12] |
| 29 racemic | 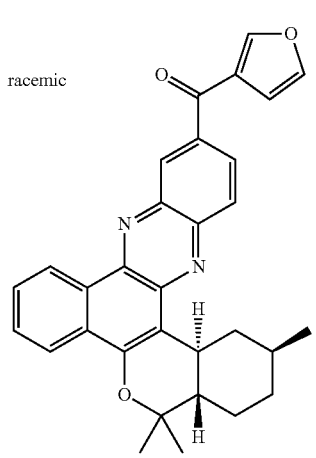 [SMILES: C[C@H]1CC[C@H]2[C@H](C1)c1c(c3ccccc3c3nc4cc(C(=O)c5ccoc5)ccc4nc13)OC2(C)C] |
| 29' racemic | 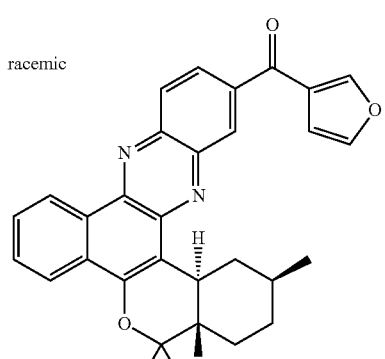 |

TABLE 1-continued
| Compound n° | Structure |
|---|---|
| 30 racemic | 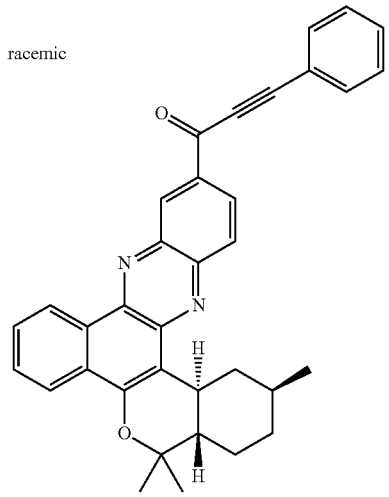 [SMILES: C[C@H]1CC[C@H]2[C@H](C1)c1c(c3ccccc3c3nc4cc(C(=O)C#Cc5ccccc5)ccc4nc13)OC2(C)C] |
| 30' racemic | 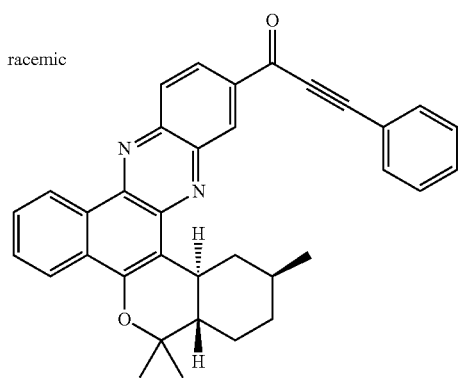 [SMILES: C[C@H]1CC[C@H]2[C@H](C1)c1c(c3ccccc3c3nc4ccc(C(=O)C#Cc5ccccc5)cc4nc13)OC2(C)C] |
| 31 racemic | 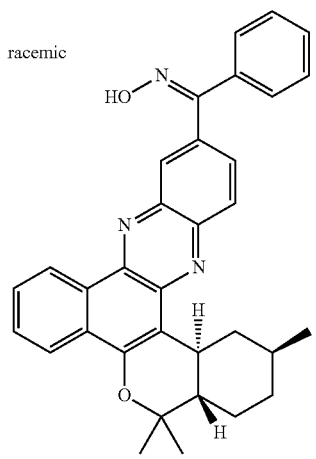 [SMILES: C[C@H]1CC[C@H]2[C@H](C1)c1c(c3ccccc3c3nc4cc(/C(=N\O)c5ccccc5)ccc4nc13)OC2(C)C] |

TABLE 1-continued
| Compound n° | Structure |
|---|---|
| 31' racemic | 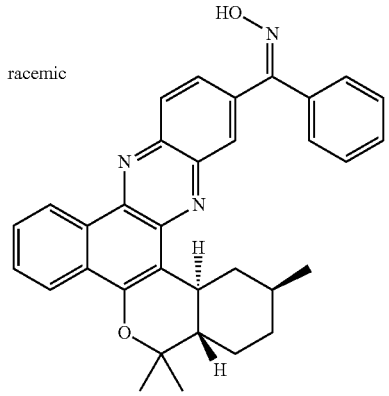 [SMILES: C[C@H]1CC[C@H]2[C@H](C1)c1c(c3ccccc3c3nc4ccc(/C(=N\O)c5ccccc5)cc4nc13)OC2(C)C] |
| 32 | 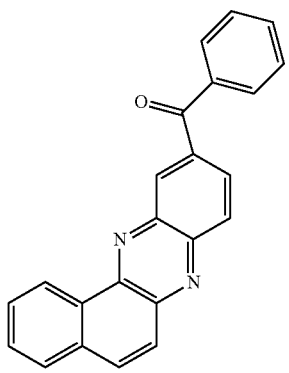 [SMILES: O=C(c1ccccc1)c1ccc2nc3ccc4ccccc4c3nc2c1] |
| 32' | 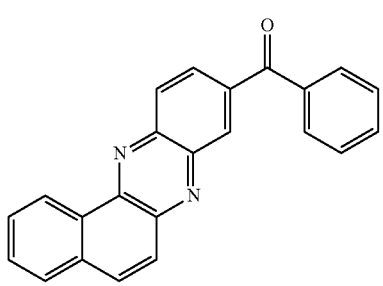 [SMILES: O=C(c1ccccc1)c1ccc2nc3c(ccc4ccccc43)nc2c1] |
| 33 racemic | 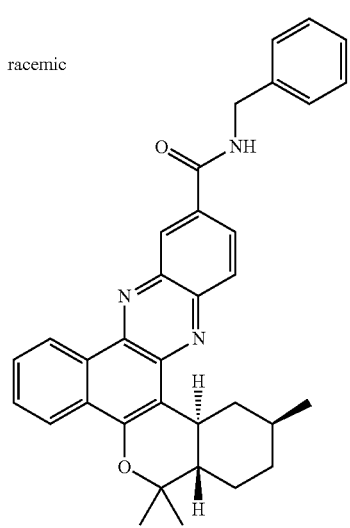 [SMILES: C[C@H]1CC[C@H]2[C@H](C1)c1c(c3ccccc3c3nc4cc(C(=O)NCc5ccccc5)ccc4nc13)OC2(C)C] |

TABLE 1-continued
| Compound n° | Structure |
|---|---|
| 33' racemic | 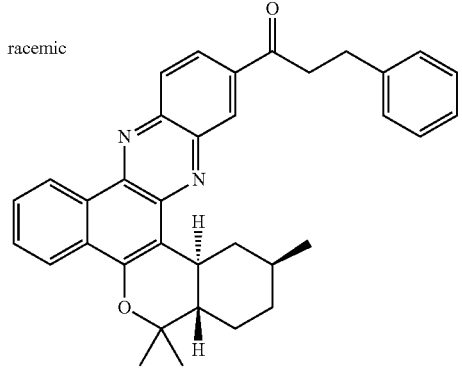 [SMILES: C[C@H]1CC[C@H]2[C@H](C1)c1c(c3ccccc3c3nc4ccc(C(=O)CCc5ccccc5)cc4nc13)OC2(C)C] |
| 34 racemic | 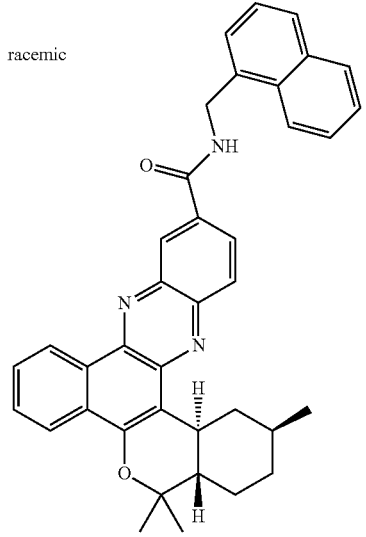 [SMILES: C[C@H]1CC[C@H]2[C@H](C1)c1c(c3ccccc3c3nc4cc(C(=O)NCc5cccc6ccccc56)ccc4nc13)OC2(C)C] |
| 34' racemic | 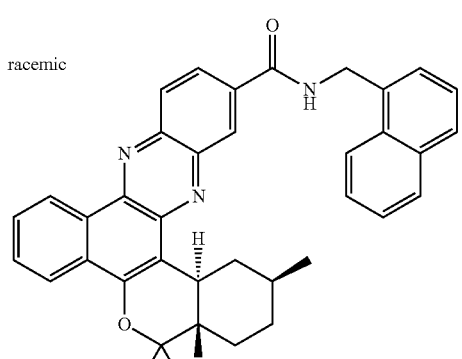 |

TABLE 1-continued
| Compound n° | Structure |
| --- | --- |
| 35 racemic | 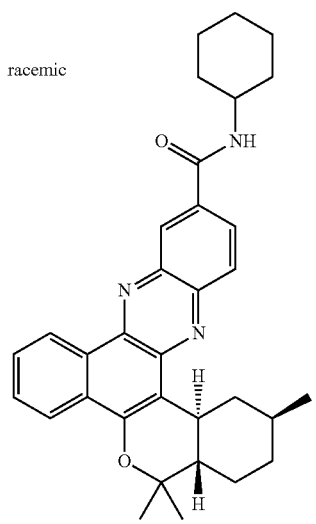 [SMILES: C[C@H]1CC[C@H]2[C@H](C1)c1c(c3ccccc3c3nc4cc(C(=O)NC5CCCCC5)ccc4nc13)OC2(C)C] |
| 35' racemic | 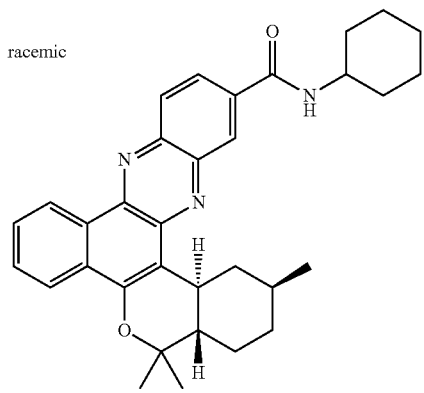 [SMILES: C[C@H]1CC[C@H]2[C@H](C1)c1c(c3ccccc3c3nc4ccc(C(=O)NC5CCCCC5)cc4nc13)OC2(C)C] |
| 36 racemic | 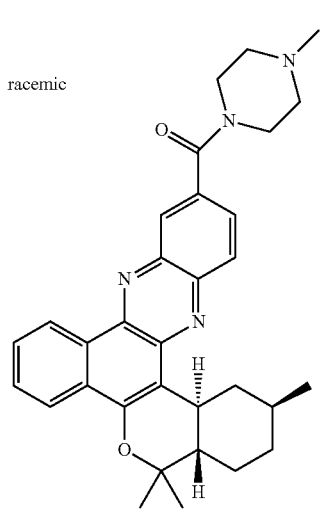 [SMILES: C[C@H]1CC[C@H]2[C@H](C1)c1c(c3ccccc3c3nc4cc(C(=O)N5CCN(C)CC5)ccc4nc13)OC2(C)C] |

TABLE 1-continued
| Compound n° | Structure |
|---|---|
| 36' | racemic 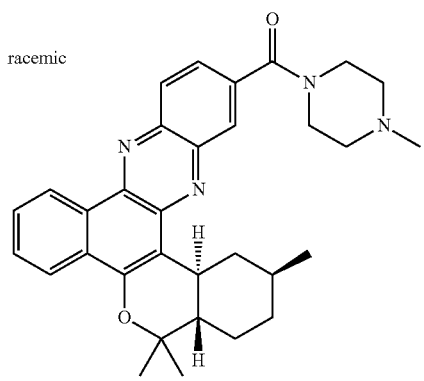 [SMILES: C[C@H]1CC[C@H]2[C@H](C1)c1c(c3ccccc3c3nc4ccc(C(=O)N5CCN(C)CC5)cc4nc13)OC2(C)C] |
| 37 | racemic 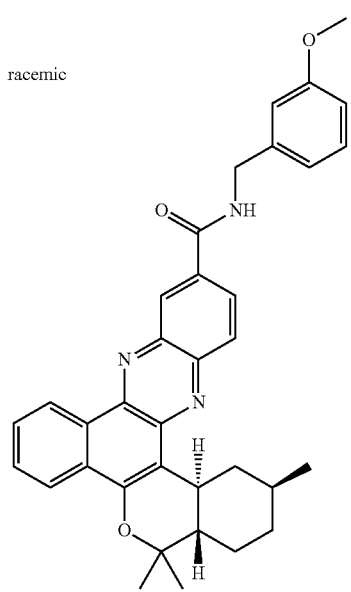 [SMILES: COc1cccc(CNC(=O)c2ccc3nc4c5c(c6ccccc6c4nc3c2)OC(C)(C)[C@H]2CC[C@H](C)C[C@H]52)c1] |
| 37' | racemic 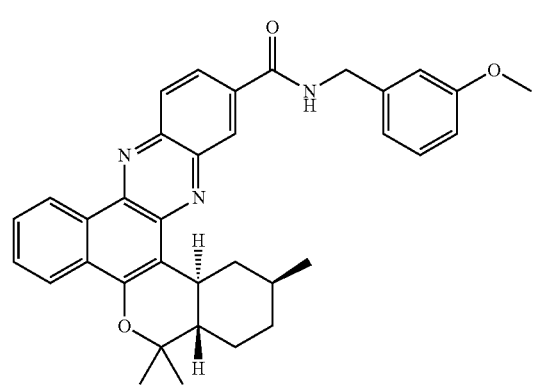 |

TABLE 1-continued
| Compound n° | Structure |
|---|---|
| 38 | 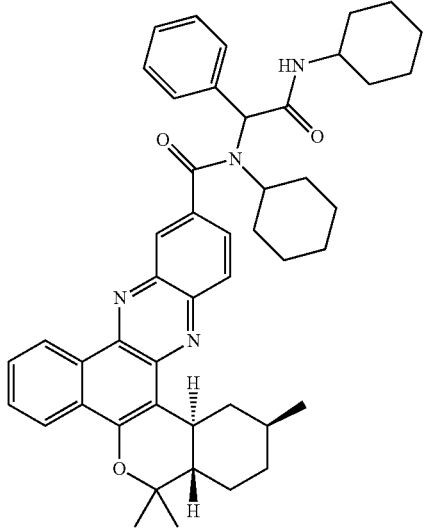 racemic |
| 38' racemic | 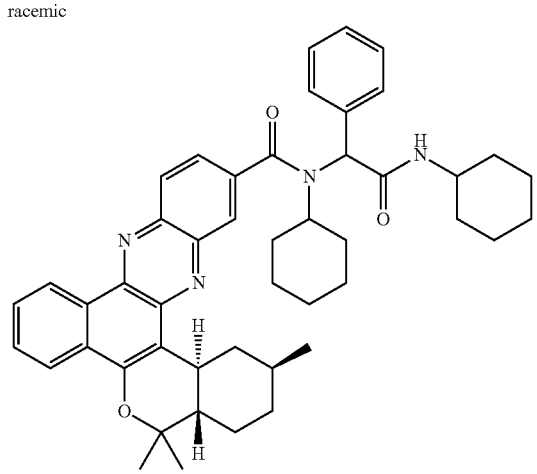 [SMILES: C[C@H]1CC[C@H]2[C@H](C1)c1c(c3ccccc3c3nc4ccc(C(=O)N(C5CCCCC5)C(C(=O)NC5CCCCC5)c5ccccc5)cc4nc13)OC2(C)C] |
| 39 racemic | 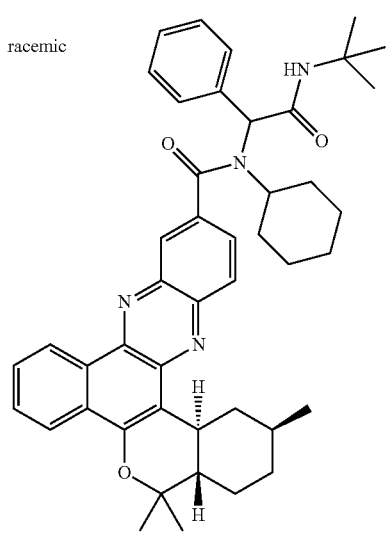 [SMILES: C[C@H]1CC[C@H]2[C@H](C1)c1c(c3ccccc3c3nc4cc(C(=O)N(C5CCCCC5)C(C(=O)NC(C)(C)C)c5ccccc5)ccc4nc13)OC2(C)C] |

TABLE 1-continued
| Compound n° | Structure |
|---|---|
| 39' racemic | 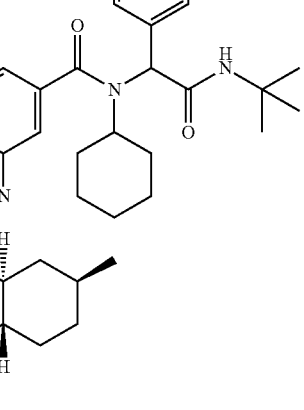 |
| 40 racemic | 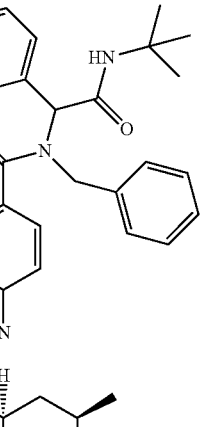 |
| 40' racemic | 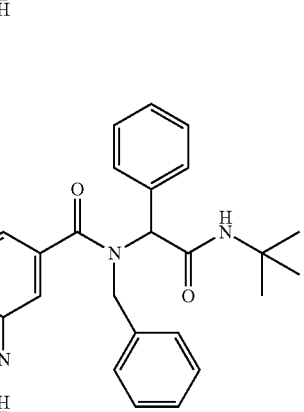 |

TABLE 1-continued
| Compound n° | Structure |
|---|---|
| 41 | racemic 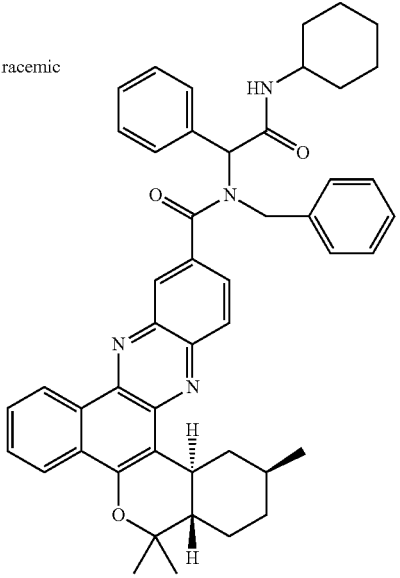 [SMILES: C[C@H]1CC[C@H]2[C@H](C1)c1c(c3ccccc3c3nc4cc(C(=O)N(Cc5ccccc5)C(C(=O)NC5CCCCC5)c5ccccc5)ccc4nc13)OC2(C)C] |
| 41' | 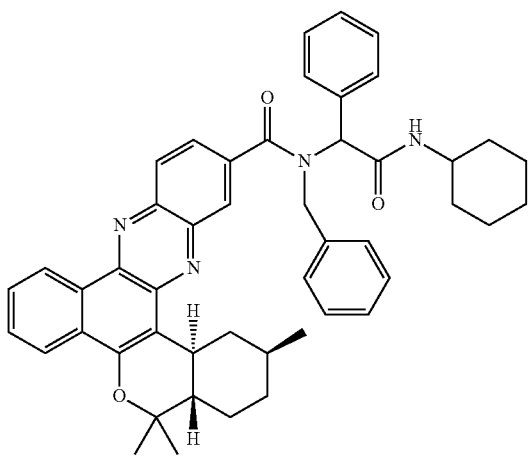 racemic |
| 42 | 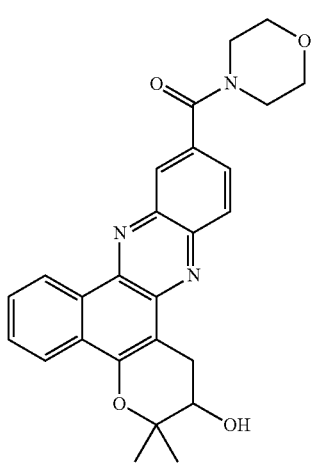 |

TABLE 1-continued
| Compound n° | Structure |
|---|---|
| 42' | 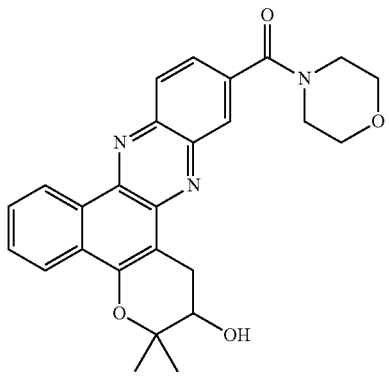 [SMILES: CC1(C)Oc2c(c3nc4cc(C(=O)N5CCOCC5)ccc4nc3c3ccccc23)CC1O] |
| 43 | 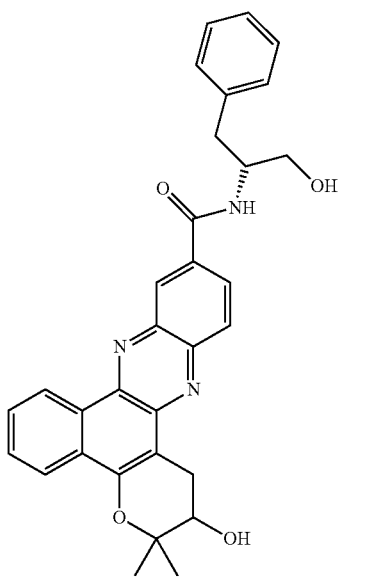 |
| 43' | 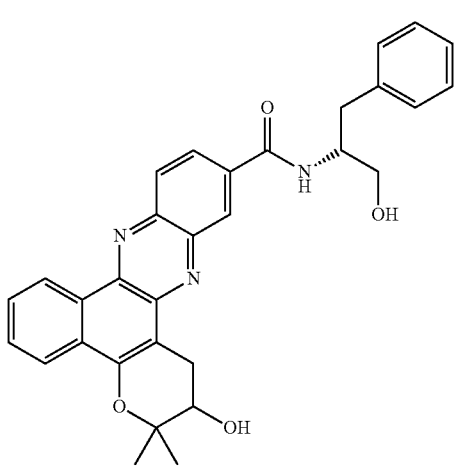 |

TABLE 1-continued

| Compound n° | Structure |
|---|---|
| 44 | 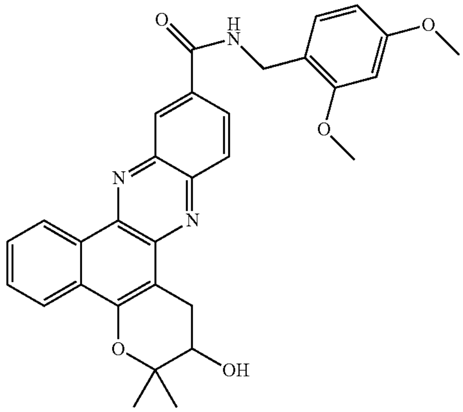 [SMILES: COc1ccc(CNC(=O)c2ccc3nc4c5c(c6ccccc6c4nc3c2)OC(C)(C)C(O)C5)c(OC)c1] |
| 44' | 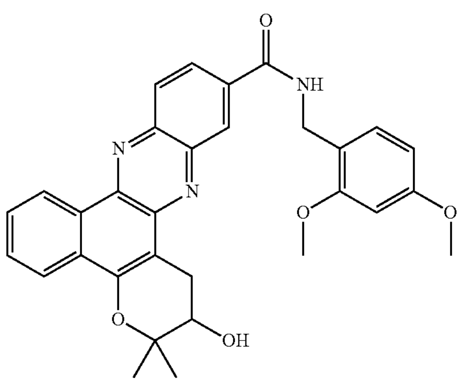 [SMILES: COc1ccc(CNC(=O)c2ccc3nc4c(nc3c2)c2c(c3ccccc34)OC(C)(C)C(O)C2)c(OC)c1] |
| 45 racemic | |

TABLE 1-continued

| Compound n° | Structure |
|---|---|
| 45' | racemic |
| 46 | racemic |
| 46' | racemic |

TABLE 1-continued
| Compound n° | Structure |
|---|---|
| 47 | racemic 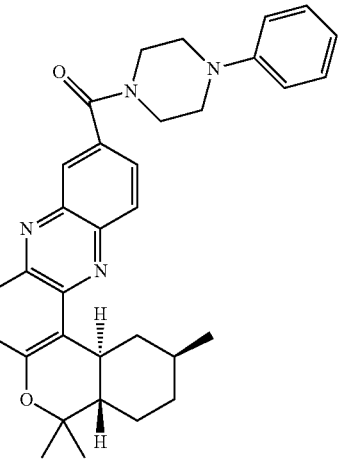 |
| 47' | racemic 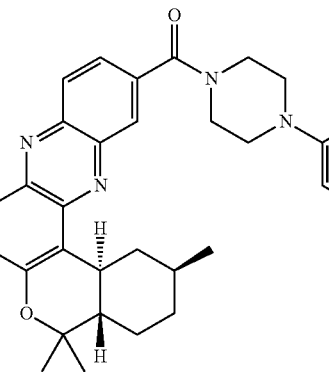 |
| 48 | racemic 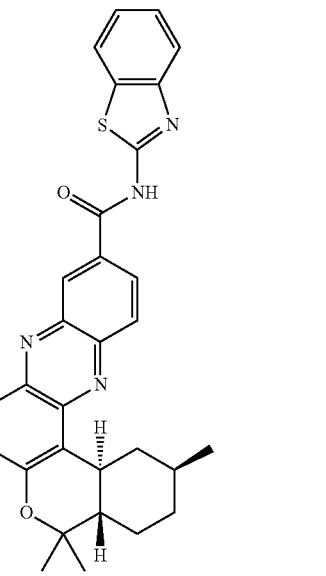 |

TABLE 1-continued

| Compound n° | Structure |
|---|---|
| 48' | racemic |
| 49 | racemic |
| 49' | racemic |

TABLE 1-continued
| Compound n° | Structure |
|---|---|
| 50 | racemic 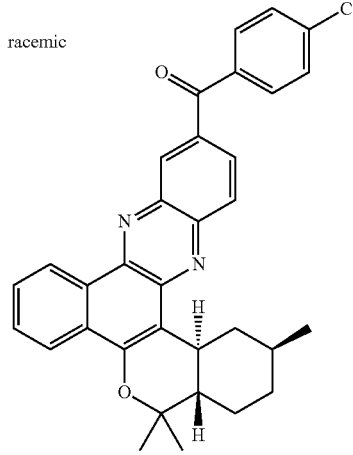 |
| 50' | racemic 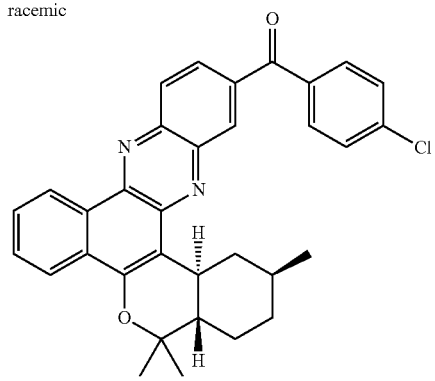 [SMILES: C[C@H]1CC[C@H]2[C@H](C1)c1c(c3ccccc3c3nc4ccc(C(=O)c5ccc(Cl)cc5)cc4nc13)OC2(C)C] |
| 51 | racemic 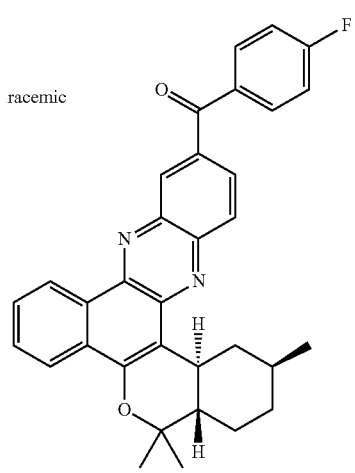 [SMILES: C[C@H]1CC[C@H]2[C@H](C1)c1c(c3ccccc3c3nc4cc(C(=O)c5ccc(F)cc5)ccc4nc13)OC2(C)C] |

TABLE 1-continued

| Compound n° | Structure |
|---|---|
| 51' | racemic |
| 52 | racemic |
| 52' | racemic |

TABLE 1-continued
| Compound n° | Structure |
|---|---|
| 53 | 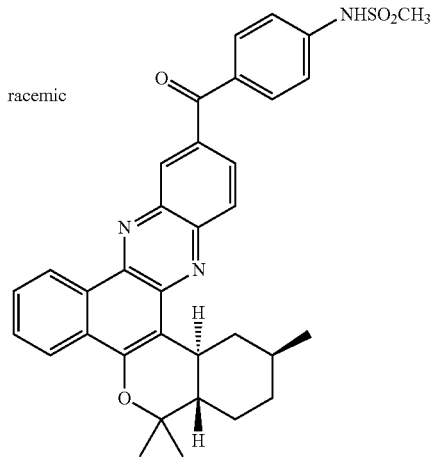 racemic |
| 53' | 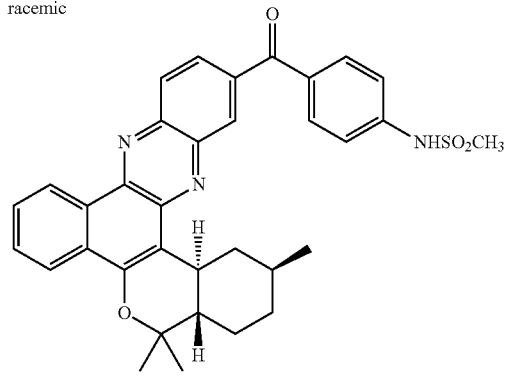 racemic |
| (R)-53 | 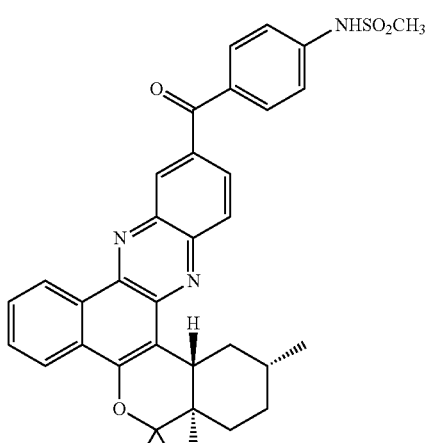 chiral |

TABLE 1-continued

| Compound n° | Structure |
|---|---|
| (R)-53' | chiral |
| (S)-53 | chiral |
| (S)-53' | chiral |

US 9,181,265 B2
TABLE 1-continued
| Compound n° | Structure |
|---|---|
| 54 racemic | 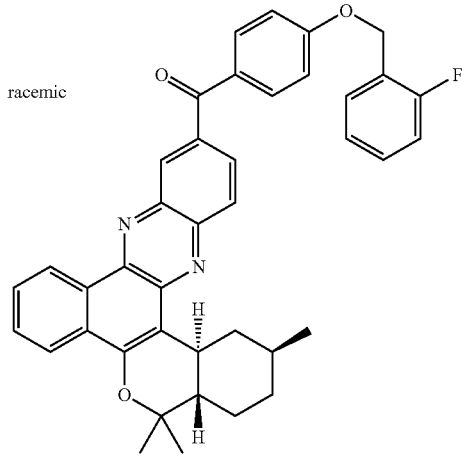 [SMILES: C[C@H]1CC[C@H]2[C@H](C1)c1c(c3ccccc3c3nc4cc(C(=O)c5ccc(OCc6ccccc6F)cc5)ccc4nc13)OC2(C)C] |
| 54' racemic | 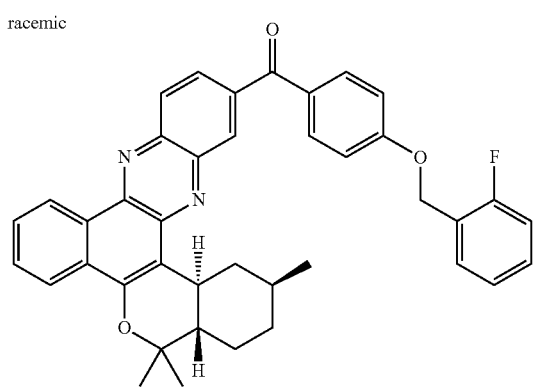 [SMILES: C[C@H]1CC[C@H]2[C@H](C1)c1c(c3ccccc3c3nc4ccc(C(=O)c5ccc(OCc6ccccc6F)cc5)cc4nc13)OC2(C)C] |
| 55 racemic | 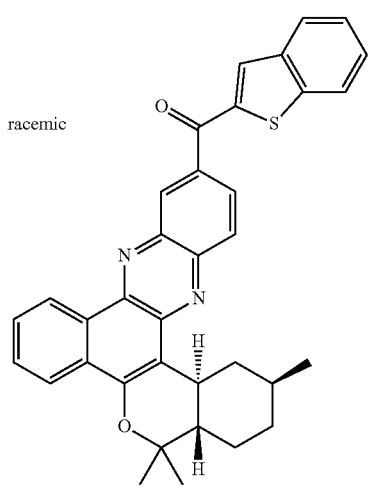 [SMILES: C[C@H]1CC[C@H]2[C@H](C1)c1c(c3ccccc3c3nc4cc(C(=O)c5cc6ccccc6s5)ccc4nc13)OC2(C)C] |

TABLE 1-continued
| Compound n° | Structure |
|---|---|
| 55' racemic | 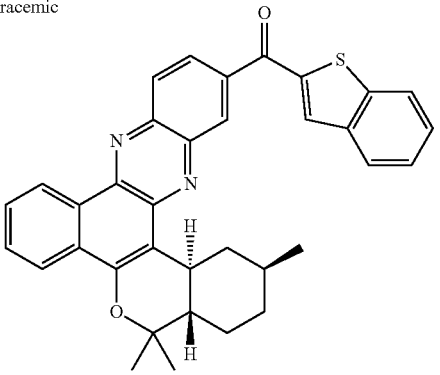 [SMILES: C[C@H]1CC[C@H]2[C@H](C1)c1c(c3ccccc3c3nc4ccc(C(=O)c5cc6ccccc6s5)cc4nc13)OC2(C)C] |
| 56 racemic | 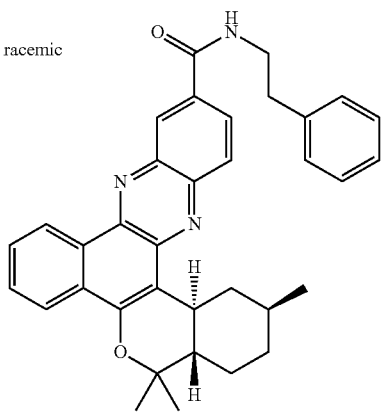 [SMILES: C[C@H]1CC[C@H]2[C@H](C1)c1c(c3ccccc3c3nc4cc(C(=O)NCCc5ccccc5)ccc4nc13)OC2(C)C] |
| 56' racemic | 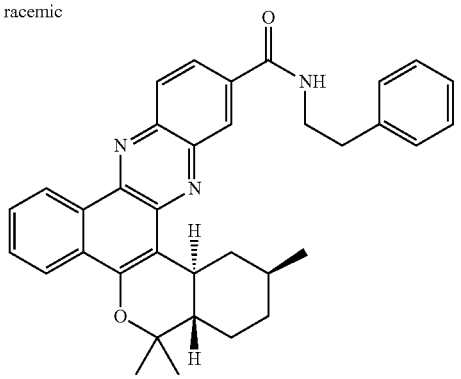 [SMILES: C[C@H]1CC[C@H]2[C@H](C1)c1c(c3ccccc3c3nc4ccc(C(=O)NCCc5ccccc5)cc4nc13)OC2(C)C] |
| (R)-56 | 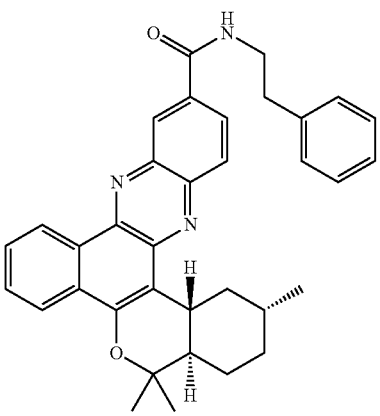 [SMILES: C[C@@H]1CC[C@@H]2[C@@H](C1)c1c(c3ccccc3c3nc4cc(C(=O)NCCc5ccccc5)ccc4nc13)OC2(C)C] |

TABLE 1-continued

| Compound n° | Structure |
|---|---|
| (R)-56' | 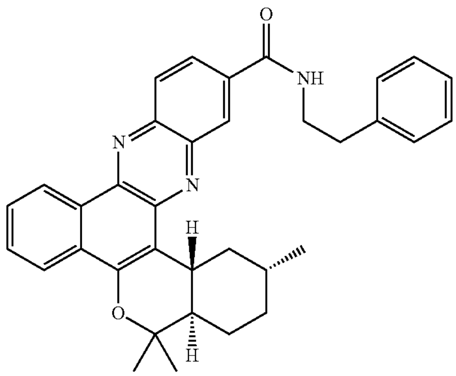 [SMILES: C[C@@H]1CC[C@@H]2[C@@H](C1)c1c(c3ccccc3c3nc4ccc(C(=O)NCCc5ccccc5)cc4nc13)OC2(C)C] |
| (S)-56 | 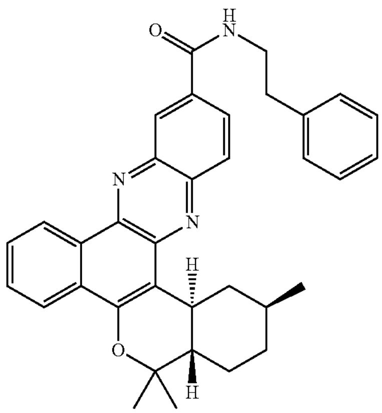 [SMILES: C[C@H]1CC[C@H]2[C@H](C1)c1c(c3ccccc3c3nc4cc(C(=O)NCCc5ccccc5)ccc4nc13)OC2(C)C] |
| (S)-56' | 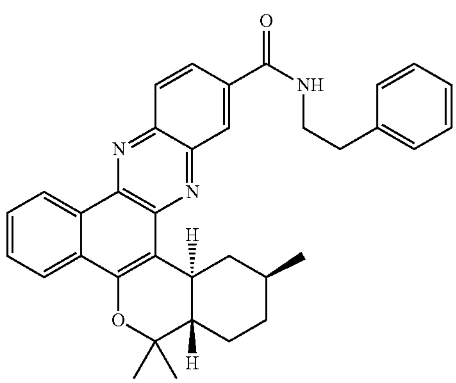 [SMILES: C[C@H]1CC[C@H]2[C@H](C1)c1c(c3ccccc3c3nc4ccc(C(=O)NCCc5ccccc5)cc4nc13)OC2(C)C] |

The compounds of the invention can be prepared using a series of chemical reactions well known to those skilled in the art, altogether making up the process for preparing said compounds which are exemplified further. The processes described further are only viewed as examples and by no means are meant to limit the scope of the present invention.

The compounds of the invention can be prepared by condensation of an ortho-benzoquinone and an aromatic 1,2-diamine resulting in a mixture of regioisomers of formula I using methods known in the art. Detailed descriptions of suitable methods can be found in the examples section.

Applications

The compounds of the invention are potent anti-angiogenic agents, and/or anti-cancer agents, particularly anti-tumor agents, in particular under hypoxic conditions, and thus inhibit endothelial cell growth as well as cancer cell growth. The compounds of the invention show selectivity S under hypoxic conditions, wherein S is defined as the ratio between the $IC_{50}$ of a compound under normoxic conditions and the $IC_{50}$ of the same compound under hypoxic conditions:

$$S = \frac{IC_{50}(normoxic)}{IC_{50}(hypoxic)}.$$

Therefore, the invention also provides the use of the compounds of the invention or pharmaceutically acceptable salts or solvates thereof as anti-angiogenic agent and/or cytotoxic agents under hypoxic conditions. They are therefore useful in the treatment of cancer since they selectively inhibit angiogenesis and/or inhibit, block, reduce, decrease cancer cell proliferation and/or division, and/or stimulate cancer cell death. They are also useful in the treatment of any disease characterized by abnormal angiogenesis in humans or animals, referred herein as angiogenic disorders.

The invention therefore also provides a method of treating mammalian cancer including solid tumors as well as sarcomas and hematologic cancers, and angiogenic disorders. The compounds of the invention and their pharmaceutically acceptable salts and solvates can be used to inhibit, block, reduce, decrease, endothelial cell proliferation and/or endothelial cell division. The compounds of the invention and their pharmaceutically acceptable salts and solvates can also be used to inhibit, block, reduce, decrease cancer cell proliferation and/or division, and/or stimulate cancer cell death. Hence, the method comprises administering to a mammal in need thereof, including a human, a pharmaceutically effective amount of a compound of this invention, or a pharmaceutically acceptable salt or solvate thereof.

Examples of solid tumors include, but are not limited to, cancers of the breast, respiratory tract, brain, reproductive organs, digestive tract, urinary tract, eye, liver, skin, head and neck, thyroid, parathyroid and their distant metastases.

Examples of breast cancer include, but are not limited to invasive ductal carcinoma, invasive lobular carcinoma, ductal carcinoma in situ, and lobular carcinoma in situ.

Examples of cancers of the respiratory tract include, but are not limited to small-cell and non-small-cell lung carcinoma, as well as bronchial adenoma and pleuropulmonary blastoma.

Examples of brain cancers include, but are not limited to brain stem and hypophtalmic glioma, cerebellar and cerebral astrocytoma, medulloblastoma, ependymoma, as well as neuroectodermal and pineal tumor.

Examples of tumors of the male reproductive organs include, but are not limited to prostate and testicular cancer. Tumors of the female reproductive organs include, but are not limited to endometrial, cervical, ovarian, vaginal, and vulvar cancer, as well as sarcoma of the uterus.

Examples of tumors of the digestive tract include, but are not limited to anal, colon, colorectal, esophageal, gallbladder, gastric, pancreatic, rectal, small-intestine, and salivary gland cancers. Tumors of the urinary tract include, but are not limited to bladder, penile, kidney, renal pelvis, ureter, urethral and human papillary renal cancers.

Examples of eye cancers include, but are not limited to intraocular melanoma and retinoblastoma.

Examples of liver cancers include, but are not limited to hepatocellular carcinoma (liver cell carcinomas with or without fibrolamellar variant), cholangiocarcinoma (intrahepatic bile duct carcinoma), and mixed hepatocellular cholangiocarcinoma.

Examples of skin cancers include, but are not limited to squamous cell carcinoma, Kaposi's sarcoma, malignant melanoma, Merkel cell skin cancer, and non-melanoma skin cancer.

Examples of head-and-neck cancers include, but are not limited to laryngeal, hypopharyngeal, nasopharyngeal, oropharyngeal cancer, lip and oral cavity cancer and squamous cell.

Sarcomas include, but are not limited to sarcoma of the soft tissue, osteosarcoma, malignant fibrous histiocytoma, lymphosarcoma, and rhabdomyosarcoma.

Hematologic cancers include leukemia, lymphoma, and myeloma.

Examples of leukemias include, but are not limited to acute myeloid leukemia, acutelymphoblastic leukemia, chronic lymphocytic leukemia, chronic myelogenous leukemia, and hairy cell leukemia.

Examples of lymphomas include, but are not limited to AIDS-related lymphoma, non-Hodgkin's lymphoma, cutaneous T-cell lymphoma, Burkitt lymphoma, Hodgkin's disease, and lymphoma of the central nervous system.

As set out above, the compounds of the invention or pharmaceutically acceptable salts or solvates thereof can also be used to treat any disease characterized by abnormal angiogenesis in humans or animals, referred herein to as angiogenic disorders. Such disorders include, but are not limited to, blood vessel diseases such as atherosclerosis, vein or artery occlusion, arteriovenous malformations; ocular neovascular diseases such as diabetic retinopathy and other eyes conditions, such as macular degeneration (Lopez et al. Invest. Ophtalmol. Vis. Sci. 1996, 37, 855), corneal graft rejection, neovascular glaucoma, retinopathy of prematurity (Aiello et al. New Engl. J. Med. 1994, 331, 1480; Peer et al. Lab. Invest. 1995, 72, 638); skin diseases such as psoriasis; abnormal wound healing; hypertrophic scars and keloids and endometriosis.

The compounds of the invention or pharmaceutically acceptable salts or solvates thereof can also be used to treat inflammatory, immune and infectious diseases characterized by proliferation of vascular endothelial cells, including, but not limited to, rheumatoid arthritis, osteoarthritis, ulcerative colitis, Crohn's disease, sarcoidosis, inflammatory or immune mediated bowel disease, systemic lupus, bacterial infections such as Bartonellosis and parasitic infections.

The compounds of the invention or pharmaceutically acceptable salts or solvates thereof can also be used as a birth control agent by preventing vascularisation required for blastocyst implantation and for development of placenta, the blastcyst and the embryo.

The above mentioned cancers and angiogenic disorders, inflammatory, immune and infectious diseases have been well characterized in humans, but also exist with a similar etiology in other mammals, and can be treated by administering pharmaceutical compositions of the present invention.

In a particular embodiment, the cancer is a solid tumor. It may particularly be selected from the group consisting of cervical cancer, breast cancer, prostate cancer, glioma, and colorectal cancer.

In another embodiment, the angiogenic disorder is diabetic retinopathy, ischemic retinal vein occlusion, and retinopathy of prematurity, age related macular degeneration and neovascular glaucoma.

The invention also provides for a pharmaceutical composition comprising a compound according to the invention or a pharmaceutically acceptable salt or solvate thereof and at least one pharmaceutically acceptable carrier, diluent, excipient and or adjuvant The invention further provides the use of a compound according to the invention or a pharmaceutically acceptable salt or solvate thereof as a medicament. In a particular embodiment, the medicament is used for treating mammalian cancer including the cancer types specified hereinabove in a patient. Preferably, the patient is a human.

In another embodiment the medicament is used for treating angiogenic disorders including those specified hereinabove in a patient. Preferably, the patient is a human.

In another embodiment the medicament is used for treating inflammatory, immune and infections diseases including those specified hereinabove in a patient. Preferably the patient is a human.

In still another embodiment, the medicament is used for birth control as specified hereinabove in a female patient. Preferably the patient is a woman.

According to one embodiment, the compounds of the invention, their pharmaceutical acceptable salts or solvates may be administered as part of a combination therapy. Thus, are included within the scope of the present invention embodiments comprising coadministration of, and compositions and medicaments which contain, in addition to a compound of the present invention, a pharmaceutically acceptable salt or solvate thereof as active ingredient, additional therapeutic agents and/or active ingredients. Such multiple drug regimens, often referred to as combination therapy, may be used in the treatment Hence, the compounds of this invention as well as their pharmaceutical acceptable salts or solvates can be administered as the sole pharmaceutical agent or in combination with one or more other pharmaceutical agents where the combination causes no unacceptable adverse effects. For example, the compounds of this invention can be combined with other anti-cancer agents, including those already on the market and those under clinical trial, as well as with admixtures and combinations thereof. The combination of the compounds of the present invention with other pharmaceutical agents used in cancer therapy and/or with radiotherapy appears particularly beneficial due to the fact that tumor areas which are hypoxic do not respond well to conventional treatments. The compounds of this invention, however, are especially active in these regions of the tumor.

The additional pharmaceutical agent can be chosen from the group consisting of aldesleukin, alendronic acid, alfaferone, alitretinoin, allopurinol, aloprim, aloxi, altretamine, aminoglutethimide, amifostine, amrubicin, amsacrine, anastrozole, anzmet, aranesp, arglabin, arsenic trioxide, aromasin, 5-azacytidine, azathioprine, BCG or tice BCG, bestatin, betamethasone acetate, betamethasone sodium phosphate, bexarotene, bleomycin sulfate, broxuridine, bortezomib, busulfan, calcitonin, campath, capecitabine, carboplatin, casodex, cefesone, celmoleukin, cerubidine, chlorambucil, cisplatin, cladribine, cladribine, clodronic acid, cyclophosphamide, cytarabine, dacarbazine, dactinomycin, DaunoXome, decadron, decadron phosphate, delestrogen, denileukin diftitox, depo-medrol, deslorelin, dexrazoxane, diethylstilbestrol, diflucan, docetaxel, doxifluridine, doxorubicin, dronabinol, DW-166HC, eligard, elitek, ellence, emend, epirubicin, epoetin alfa, epogen, eptaplatin, ergamisol, estrace, estradiol, estramustine phosphate sodium, ethinyl estradiol, ethyol, etidronic acid, etopophos, etoposide, fadrozole, farston, filgrastim, finasteride, fligrastim, floxuridine, fluconazole, fludarabine, 5-fluorodeoxyuridine monophosphate, 5-fluorouracil (5-FU)1 fluoxymesterone, flutamide, formestane, fosteabine, fotemustine, fulvestrant, gammagard, gemcitabine, gemtuzumab, gleevec, gliadel, goserelin, granisetron HCl1 histrelin, hycamtin, hydrocortone, eyrthrohydroxynonyladenine, hydroxyurea, ibritumomab tiuxetan, idarubicin, ifosfamide, interferon alpha, interferon-alpha 2, interferon alfa-2[alpha], interferon alfa-2B, interferon alfanl, interferon alfa-n3, interferon beta, interferon gamma-1 [alpha], interleukin-2, intron A1 iressa, irinotecan, kytril, lentinan sulphate, letrozole, leucovorin, leuprolide, leuprolide acetate, levamisole, levofolinic acid calcium salt, levothroid, levoxyl, lomustine, Ionidamine, marinol, mechlorethamine, mecobalamin, medroxyprogesterone acetate, megestrol acetate, melphalan, menest, 6-mercaptopurine, Mesna, methotrexate, metvix, miltefosine, minocycline, mitomycin C, mitotane, mitoxantrone, Modrenal, Myocet, nedaplatin, neulasta, neumega, neupogen, nilutamide, nolvadex, NSC-631570, OCT-43, octreotide, ondansetron HCl, orapred, oxaliplatin, paclitaxel, pediapred, pegaspargase, Pegasys, pentostatin, picibanil, pilocarpine HCl, pirarubicin, plicamycin, porfimer sodium, prednimustine, prednisolone, prednisone, premarin, procarbazine, procrit, raltitrexed, rebif, rhenium-186 etidronate, rituximab, roferon-A, romurtide, salagen, sandostatin, sargramostim, semustine, sizofiran, sobuzoxane, solu-medrol, sparfosic acid, stem-cell therapy, streptozocin, strontium-89 chloride, synthroid, tamoxifen, tamsulosin, tasonermin, tastolactone, taxotere, teceleukin, temozolomide, teniposide, testosterone propionate, testred, thioguanine, thiotepa, thyrotropin, tiludronic acid, topotecan, toremifene, tositumomab, trastuzumab, treosulfan, tretinoin, trexall, trimethylmelamine, trimetrexate, triptorelin acetate, triptorelin pamoate, UFT, uridine, valrubicin, vesnarinone, vinblastine, vincristine, vindesine, vinorelbine, virulizin, zinecard, zinostatin stimalamer, zofran, ABI-007, acolbifene, actimmune, affinitak, aminopterin, arzoxifene, asoprisnil, atamestane, atrasentan, BAY 43-9006 (sorafenib), avastin, CCI-779, CDC-501, celebrex, cetuximab, crisnatoi, cyproterone acetate, decitabine, DN-101, doxorubicin-MTC, dSLIM, dutasteride, edotecarin, eflomithine, exatecan, fenretinide, histamine dihydrochloride, histrelin hydrogel implant, holmium-166 DOTMP, ibandronic acid, interferon gamma, intron-PEG, ixabepilone, keyhole limpet hemocyanin, L-651582, lanreotide, lasofoxifene, libra, Ionafarnib, miproxifene, minodronate, MS-209, liposomal MTP-PE, MX-6, nafarelin, nemorubicin, neovastat, nolatrexed, oblimersen, onco-TCS, osidem, paclitaxel polyglutamate, pamidronate disodium, PN-401, QS-21, quazepam, R-1549, raloxifene, ranpirnase, 13-cis-retinoic acid, satraplatin, seocalcitol, T-138067, tarceva, taxoprexin, thymosin alpha 1, tiazofurine, tipifarnib, tirapazamine, TLK-286, toremifene, TransMID-107R, valspodar, vapreotide, vatalanib, verteporfin, vinflunine, Z-100, zoledronic acid or combinations thereof. Optional anti-hyperproliferative agents which can be added to the composition include but are not limited to compounds listed on the cancer chemotherapy drug regimens in the 11th Edition of the Merck Index, (1996), which is hereby incorporated by reference, such as asparaginase, bleomycin, carboplatin, carmustine, chlorambucil, cisplatin, colaspase, cyclophosphamide, cytarabine, dacarbazine, dactinomycin, daunorubicin, doxorubicin (adriamycine), epirubicin, etoposide, 5-fluorouracil, hexamethylmelamine, hydroxyurea, ifosfamide, irinotecan, leucovorin, lomustine, mechlorethamine, 6-mercaptopurine, mesna, methotrexate, mitomycin C, mitoxantrone, prednisolone, prednisone, procarbazine, raloxifen, streptozocin, tamoxifen, thioguanine, topotecan, vinblastine, vincristine, and vindesine.

Other anti-hyperproliferative agents suitable for use with the composition of the invention include but are not limited to those compounds acknowledged to be used in the treatment of neoplastic diseases in Goodman and Gilman's The Pharmacological Basis of Therapeutics (Ninth Edition), editor Molinoff et al., publ. by McGraw-Hill, pages 1225-1287, (1996), which is hereby incorporated by reference, such as aminoglutethimide, L-asparaginase, azathioprine, 5-azacytidine cladribine, busulfan, diethylstilbestrol, 2',2'-difluorodeoxycytidine, docetaxel, erythrohydroxynonyl adenine, ethinyl estradiol, 5-fluorodeoxyuridine, 5-fluorodeoxyuridine monophosphate, fludarabine phosphate, fluoxymesterone, flutamide, hydroxyprogesterone caproate, idarubicin, interferon, medroxyprogesterone acetate, megestrol acetate, melphalan, mitotane, paclitaxel, pentostatin, N-phosphonoacetyl-L-aspartate (PALA), plicamycin, semustine, teniposide, testosterone propionate, thiotepa, trimethylmelamine, uridine, and vinorelbine.

Other anti-hyperproliferative agents suitable for use with the composition of the invention include but are not limited to other anti-cancer agents such as epothilone and its derivatives, irinotecan, raloxifen and topotecan.

Combinations with:
1) other targeted therapies directed against angiogenesis like avastin, sorafenib, DAST, sunitinib, axitinib or AZD 2171, which are presently under development; or
2) inhibitors of proteasomes and mTOR, anti-hormones or steroid metabolic enzyme inhibitors are especially favorable for patients due to the beneficial side effect profile of targeted therapies.

Generally, the use of cytotoxic and/or cytostatic agents in combination with a compound or composition of the present invention may serve to:
(1) yield better efficacy in reducing the growth of a tumor or even eliminate the tumor as compared to administration of either agent alone,
(2) provide for the administration of lesser amounts of the administered chemo-therapeutic agents,
(3) provide for a chemotherapeutic treatment that is well tolerated in the patient with fewer deleterious pharmacological complications than observed with single agent chemotherapies and certain other combined therapies,
(4) provide for treating a broader spectrum of different cancer types in mammals, especially humans,
(5) provide for a higher response rate among treated patients,
(6) provide for a longer survival time among treated patients compared to standard chemotherapy treatments,
(7) provide a longer time for tumor progression, and/or
(8) yield efficacy and tolerability results at least as good as those of the agents used alone, compared to known instances where other cancer agent combinations produce antagonistic effects.

In the above-described embodiment combinations of the present invention, a compound of the invention, a pharmaceutically acceptable salt or solvate thereof and other therapeutic active agents may be administered in terms of dosage forms either separately or in conjunction with each other, and in terms of their time of administration, either serially or simultaneously. Thus, the administration of one component agent may be prior to, concurrent with, or subsequent to the administration of the other component agent(s).

The invention also provides pharmaceutical compositions comprising a compound of the invention or a pharmaceutically acceptable salt or solvate thereof and at least one pharmaceutically acceptable carrier, diluent, excipient and/or adjuvant. As indicated above, the invention also covers pharmaceutical compositions which contain, in addition to a compound of the present invention, a pharmaceutically acceptable salt or solvate thereof as active ingredient, additional therapeutic agents and/or active ingredients.

Generally, for pharmaceutical use, the compounds of the inventions may be formulated as a pharmaceutical preparation comprising at least one compound of the invention and at least one pharmaceutically acceptable carrier, diluent, excipient and/or adjuvant, and optionally one or more further pharmaceutically active compounds.

By means of non-limiting examples, such a formulation may be in a form suitable for oral administration, for parenteral administration (such as by intravenous, intramuscular or subcutaneous injection or intravenous infusion), for topical administration (including ocular), for administration by inhalation, by a skin patch, by an implant, by a suppository, etc. Such suitable administration forms—which may be solid, semi-solid or liquid, depending on the manner of administration—as well as methods and carriers, diluents and excipients for use in the preparation thereof, will be clear to the skilled person; reference is made to the latest edition of Remington's Pharmaceutical Sciences.

Some preferred, but non-limiting examples of such preparations include tablets, pills, powders, lozenges, sachets, cachets, elixirs, suspensions, emulsions, solutions, syrups, aerosols, ointments, cremes, lotions, soft and hard gelatin capsules, suppositories, drops, sterile injectable solutions and sterile packaged powders (which are usually reconstituted prior to use) for administration as a bolus and/or for continuous administration, which may be formulated with carriers, excipients, and diluents that are suitable per se for such formulations, such as lactose, dextrose, sucrose, sorbitol, mannitol, starches, gum acacia, calcium phosphate, alginates, tragacanth, gelatin, calcium silicate, microcrystalline cellulose, polyvinylpyrrolidone, polyethylene glycol, cellulose, (sterile) water, methylcellulose, methyl- and propylhydroxybenzoates, talc, magnesium stearate, edible oils, vegetable oils and mineral oils or suitable mixtures thereof. The formulations can optionally contain other substances that are commonly used in pharmaceutical formulations, such as lubricating agents, wetting agents, emulsifying and suspending agents, dispersing agents, desintegrants, bulking agents, fillers, preserving agents, sweetening agents, flavoring agents, flow regulators, release agents, etc. The compositions may also be formulated so as to provide rapid, sustained or delayed release of the active compound(s) contained therein.

The pharmaceutical preparations of the invention are preferably in a unit dosage form, and may be suitably packaged, for example in a box, blister, vial, bottle, sachet, ampoule or in any other suitable single-dose or multi-dose holder or container (which may be properly labeled); optionally with one or more leaflets containing product information and/or instructions for use. Generally, such unit dosages will contain between 0.05 and 1000 mg, and usually between 1 and 500 mg, of the at least one compound of the invention, e.g. about 10, 25, 50, 100, 200, 300 or 400 mg per unit dosage.

Usually, depending on the condition to be prevented or treated and the route of administration, the active compound of the invention will usually be administered between 0.1 to 1000 mg per kilogram, more often between 0.1 and 500 mg, such as between 1 and 250 mg, for example about 5, 10, 25, 50, 100 or 250 mg, per kilogram body weight of the patient per day, which may be administered as a single daily dose, divided over one or more daily doses, or essentially continuously, e.g. using a drip infusion.

DEFINITIONS

The definitions and explanations below are for the terms as used throughout the entire application, including both the specification and the claims.

When describing the compounds of the invention, the terms used are to be construed in accordance with the following definitions, unless indicated otherwise.

Where groups may be substituted, such groups may be substituted with one or more substituents, and preferably with one, two or three substituents. Substituents may be selected from but not limited to, for example, the group comprising halogen, hydroxyl, oxo, nitro, amido, carboxy, amino, cyano haloalkoxy, and haloalkyl.

As used herein the terms such as "alkyl, aryl, or cycloalkyl, each being optionally substituted with . . . " or "alkyl, aryl, or cycloalkyl, optionally substituted with . . . " encompasses "alkyl optionally substituted with . . . ", "aryl optionally substituted with . . . " and "cycloalkyl optionally substituted with . . . ".

The term "halo" or "halogen" means fluoro, chloro, bromo, or iodo. Preferred halo groups are fluoro, chloro and bromo.

The term "alkyl" by itself or as part of another substituent refers to a hydrocarbyl radical of Formula $C_nH_{2n+1}$ wherein n is a number greater than or equal to 1. Generally, alkyl groups of this invention comprise from 1 to 6 carbon atoms, preferably from 1 to 4 carbon atoms, more preferably from 1 to 3 carbon atoms, still more preferably 1 to 2 carbon atoms. Alkyl groups may be linear or branched and may be substituted as indicated herein. $C_{x-y}$-alkyl and Cx-Cy-alkyl refer to alkyl groups which comprise from x to y carbon atoms.

Suitable alkyl groups include methyl, ethyl, n-propyl, i-propyl, n-butyl, i-butyl, s-butyl and t-butyl, pentyl and its isomers (e.g. n-pentyl, iso-pentyl), and hexyl and its isomers (e.g. n-hexyl, iso-hexyl). Preferred alkyl groups include methyl, ethyl, n-propyl, i-propyl, n-butyl, i-butyl, s-butyl and t-butyl.

When the suffix "ene" ("alkylene") is used in conjunction with an alkyl group, this is intended to mean the alkyl group as defined herein having two single bonds as points of attachment to other groups. The term "alkylene" includes methylene, ethylene, methylmethylene, propylene, ethylethylene, and 1,2-dimethylethylene.

The term "alkenyl" as used herein refers to an unsaturated hydrocarbyl group, which may be linear or branched, comprising one or more carbon-carbon double bonds. Suitable alkenyl groups comprise between 2 and 6 carbon atoms, preferably between 2 and 4 carbon atoms, still more preferably between 2 and 3 carbon atoms. Examples of alkenyl groups are ethenyl, 2-propenyl, 2-butenyl, 3-butenyl, 2-pentenyl and its isomers, 2-hexenyl and its isomers, 2,4-pentadienyl and the like.

The term "alkynyl" or "alkinyl" as used herein refers to a class of monovalent unsaturated hydrocarbyl groups, wherein the unsaturation arises from the presence of one or more carbon-carbon triple bonds. Alkynyl groups typically, and preferably, have the same number of carbon atoms as described above in relation to alkenyl groups. Non limiting examples of alkynyl groups are ethynyl, 2-propynyl, 2-butynyl, 3-butynyl, 2-pentynyl and its isomers, 2-hexynyl and its isomers—and the like. The terms "alkenylene" and "alkynylene" respectively mean an alkenyl group or an alkynyl group as defined above having two single bonds as points of attachment to other groups.

The terms "aralkynyl", "arylalkynyl" refer to an alkynyl group where one carbon is attached to an aryl ring. Non limiting examples of aralkynyl comprise phenylethynyl. When an "aralkynyl", or "arylalkynyl" group is substituted, the substituent(s) is/are attached either on the alkynyl group when valence allows or on the aryl ring.

The term "haloalkyl" alone or in combination, refers to an alkyl radical having the meaning as defined above wherein one or more hydrogens are replaced with a halogen as defined above. Non-limiting examples of such haloalkyl radicals include chloromethyl, 1-bromoethyl, fluoromethyl, difluoromethyl, trifluoromethyl, 1,1,1-trifluoroethyl and the like.

The term "cycloalkyl" as used herein is a cyclic alkyl group, that is to say, a monovalent, non-aromatic, fully saturated or partially unsaturated hydrocarbyl group having 1 or 2 cyclic structures. Cycloalkyl includes monocyclic or bicyclic hydrocarbyl groups. Cycloalkyl groups may comprise 3 or more carbon atoms in the ring and generally, according to this invention comprise from 3 to 10, more preferably from 3 to 8 carbon atoms still more preferably from 3 to 6 carbon atoms.

Examples of cycloalkyl groups include but are not limited to cyclopropyl, cyclobutyl, cyclopentyl, cyclohexyl, with cyclopropyl and cyclohexyl being particularly preferred.

When the suffix "ene" is used in conjunction with a cyclic group, this is intended to mean the cyclic group as defined herein having two single bonds as points of attachment to other groups.

Therefore, "cycloalkylene" herein refers to a saturated homocyclic hydrocarbyl biradical of Formula $C_nH_{2n-2}$. Suitable cycloalkylene groups are $C_{3-6}$ cycloalkylene group, preferably a $C_{3-5}$ cycloalkylene (i.e. 1,2-cyclopropylene, 1,1-cyclopropylene, 1,1-cyclobutylene, 1,2-cyclobutylene, 1,3-cyclobutylene, 1,3-cyclopentylene, 1,2-cyclopentylene or 1,1-cyclopentylene), more preferably a $C_{3-4}$ cycloalkylene (i.e. 1,3-cyclopropylene, 1,1-cyclopropylene, 1,1-cyclobutylene, 1,2-cyclobutylene).

Where at least one carbon atom in a cycloalkyl group is replaced with a heteroatom, the resultant ring is referred to herein as "heterocycloalkyl" or "heterocyclyl".

The terms "heterocyclyl", "heterocycloalkyl" or "heterocyclo" as used herein by itself or as part of another group refer to non-aromatic, fully saturated or partially unsaturated cyclic groups (for example, 3 to 7 member monocyclic, 7 to 11 member bicyclic, or containing a total of 3 to 10 ring atoms) which have at least one heteroatom in at least one carbon atom-containing ring. Each ring of the heterocyclic group containing a heteroatom may have 1, 2, 3 or 4 heteroatoms selected from nitrogen, oxygen and/or sulfur atoms, where the nitrogen and sulfur heteroatoms may optionally be oxidized and the nitrogen heteroatoms may optionally be quaternized. Any of the carbon atoms of the heterocyclic group may be substituted by oxo (for example piperidone, pyrrolidinone). The heterocyclic group may be attached at any heteroatom or carbon atom of the ring or ring system, where valence allows. The rings of multi-ring heterocycles may be fused, bridged and/or joined through one or more spiro atoms. Non limiting exemplary heterocyclic groups include oxetanyl, piperidinyl, azetidinyl, 2-imidazolinyl, pyrazolidinyl imidazolidinyl, isoxazolinyl, oxazolidinyl, isoxazolidinyl, thiazolidinyl, isothiazolidinyl, piperidinyl, 3H-indolyl, indolinyl, isoindolinyl, 2-oxopiperazinyl, piperazinyl, homopiperazinyl, 2-pyrazolinyl, 3-pyrazolinyl, tetrahydro-2H-pyranyl, 2H-pyranyl, 4H-pyranyl, 3,4-dihydro-2H-pyranyl, 3-dioxolanyl, 1,4-dioxanyl, 2,5-dioximidazolidinyl, 2-oxopiperidinyl, 2-oxopyrrolodinyl, indolinyl, tetrahydropyranyl, tetrahydrofuranyl, tetrahydroquinolinyl, tetrahydroisoquinolin-1-yl, tetrahydroisoquinolin-2-yl, tetrahydroisoquinolin-3-yl, tetrahydroisoquinolin-4-yl, thiomorpholin-4-yl, thiomorpholin-4-ylsulfoxide, thiomorpholin-4-ylsulfone, 1,3-dioxolanyl, 1,4-oxathianyl, 1H-pyrrolizinyl, tetrahydro-1,1-dioxothiophenyl, N-formylpiperazinyl, and morpholin-4-yl.

The ring atoms of heterocyclyl moieties are numbered based on scheme below

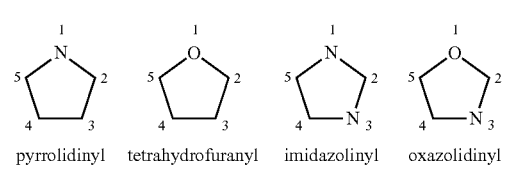

-continued

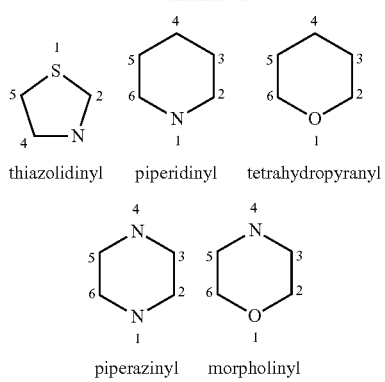

The term "aryl" as used herein refers to a polyunsaturated, aromatic hydrocarbyl group having a single ring (i.e. phenyl) or multiple aromatic rings fused together (e.g. naphtyl) or linked covalently, typically containing 5 to 12 atoms; preferably 6 to 10, wherein at least one ring is aromatic. The aromatic ring may optionally include one to two additional rings (either cycloalkyl, heterocyclyl or heteroaryl) fused thereto. Aryl is also intended to include the partially hydrogenated derivatives of the carbocyclic systems enumerated herein. Non-limiting examples of aryl comprise phenyl, biphenylyl, biphenylenyl, 5- or 6-tetralinyl, naphthalen-1- or -2-yl, 4-, 5-, 6 or 7-indenyl, 1- 2-, 3-, 4- or 5-acenaphtylenyl, 3-, 4- or 5-acenaphtenyl, 1- or 2-pentalenyl, 4- or 5-indanyl, 5-, 6-, 7- or 8-tetrahydronaphthyl, 1,2,3,4-tetrahydronaphthyl, 1,4-dihydronaphthyl, 1-, 2-, 3-, 4- or 5-pyrenyl.

The term "arylene" as used herein is intended to include divalent carbocyclic aromatic ring systems such as phenylene, biphenylylene, naphthylene, indenylene, pentalenylene, azulenylene and the like. Arylene is also intended to include the partially hydrogenated derivatives of the carbocyclic systems enumerated above. Non-limiting examples of such partially hydrogenated derivatives are 1,2,3,4-tetrahydronaphthylene, 1,4-dihydronaphthylene and the like.

The term "arylalkyl" or "aralkyl" refers to a linear or branched alkyl group where one carbon is attached to an aryl ring. Non limiting examples of aralkyl comprise benzyl, phenethyl, naphtalen-1-yl or naphtalen-2-yl methyl. When an aralkyl group is substituted, the substituent(s) is/are attached either on the alkyl group or on the aryl ring. A "x-membered aralkyl" refers to a linear or branched alkyl group where one carbon is attached to a x-membered aryl ring.

Where at least one carbon atom in an aryl group is replaced with a heteroatom, the resultant ring is referred to herein as a heteroaryl ring.

The term "heteroaryl" as used herein by itself or as part of another group refers but is not limited to 5 to 12 carbon-atom aromatic rings or ring systems containing 1 to 2 rings which are fused together or linked covalently, typically containing 5 to 6 atoms; at least one of which is aromatic, in which one or more carbon atoms in one or more of these rings is replaced by oxygen, nitrogen and/or sulfur atoms where the nitrogen and sulfur heteroatoms may optionally be oxidized and the nitrogen heteroatoms may optionally be quaternized. Such rings may be fused to an aryl, cycloalkyl, heteroaryl or heterocyclyl ring. Non-limiting examples of such heteroaryl, include: furanyl, thiophenyl, pyrazolyl, imidazolyl, oxazolyl, isoxazolyl, thiazolyl, isothiazolyl, triazolyl, oxadiazolyl, thiadiazolyl, tetrazolyl, oxatriazolyl, thiatriazolyl, pyridinyl, pyrimidyl, pyrazinyl, pyridazinyl, oxazinyl, dioxinyl, thiazinyl, triazinyl, imidazo[2,1-b][1,3]thiazolyl, thieno[3,2-b] furanyl, thieno[3,2-b]thiophenyl, thieno[2,3-d][1,3]thiazolyl, thieno[2,3-d]imidazolyl, tetrazolo[1,5-a]pyridinyl, indolyl, indolizinyl, isoindolyl, benzofuranyl, isobenzofuranyl, benzothiophenyl, isobenzothiophenyl, indazolyl, benzimidazolyl, 1,3-benzoxazolyl, 1,2-benzisoxazolyl, 2,1-benzisoxazolyl, 1,3-benzothiazolyl, 1,2-benzoisothiazolyl, 2,1-benzoisothiazolyl, benzotriazolyl, 1,2,3-benzoxadiazolyl, 2,1,3-benzoxadiazolyl, 1,2,3-benzothiadiazolyl, 2,1,3-benzothiadiazolyl, thienopyridinyl, purinyl, imidazo[1,2-a]pyridinyl, 6-oxo-pyridazin-1(6H)-yl, 2-oxopyridin-1(2H)-yl, 6-oxo-pyridazin-1(6H)-yl, 2-oxopyridin-1(2H)-yl, 1,3-benzodioxolyl, quinolinyl, isoquinolinyl, cinnolinyl, quinazolinyl, quinoxalinyl.

The term "heteroarylene" as used herein means divalent cyclic heteroaromatic ring systems including pyridinylene and the like.

The ring atoms of heteroaryl or heteroarylene moieties are numbered on scheme below:

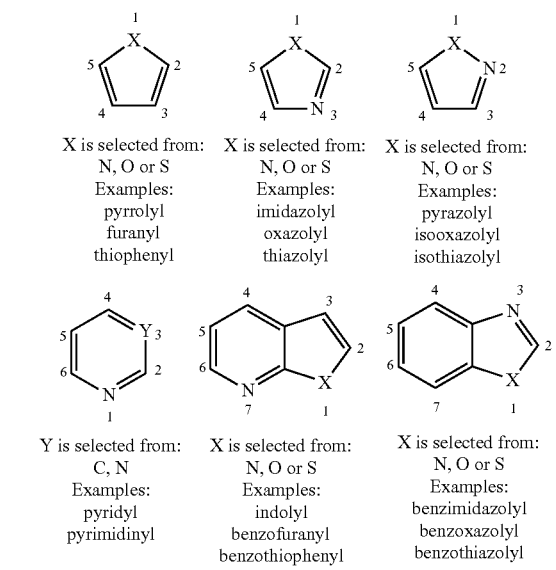

The term "alkylamino" as used herein means an amino group substituted with one or two alkyl groups. This includes monoalkylamino and dialkylamino groups.

The compounds of Formula I and subformulae thereof may contain at least one asymmetric center and may thus exist as different stereoisomeric forms. Accordingly, the present invention includes as long as not specified otherwise, all possible stereoisomers and includes not only racemic compounds but the individual enantiomers and their non racemic mixtures as well. When a compound is desired as a single enantiomer, such may be obtained by stereospecific synthesis, by resolution of the final product or any convenient intermediate, or by chiral chromatographic methods as each are known in the art. Resolution of the final product, an intermediate, or a starting material may be effected by any suitable method known in the art. See, for example, Stereochemistry of Organic Compounds by E. L. Eliel, S. H. Wilen, and L. N. Mander (Wiley-Interscience, 1994), incorporated by reference with regard to stereochemistry.

The bonds from an asymmetric carbon in compounds of the present invention may be depicted herein using a solid line (———), a zigzag line (∿∿∿), a solid wedge (◤◢) or a dotted wedge (⋯⋯). The use of a solid line to depict bonds from an asymmetric carbon atom is meant to indicate that all possible stereoisomers are meant to be included, unless it is clear from the context that a specific stereoisomer is intended. The use of either a solid or dotted wedge to depict bonds from an asymmetric carbon atom is meant to indicate that only the stereoisomer shown is meant to be included.

The compounds of the invention may also contain more than one asymmetric carbon atom. In those compounds, the use of a solid line to depict bonds from asymmetric carbon atoms is meant to indicate that all possible stereoisomers are meant to be included, unless it is clear from the context that a specific stereoisomer is intended. The solid and dotted wedges are also used to indicate relative stereochemistry. As a non limiting example,

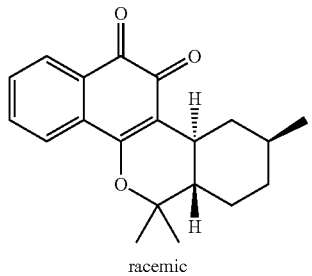

racemic means a racemic mixture of

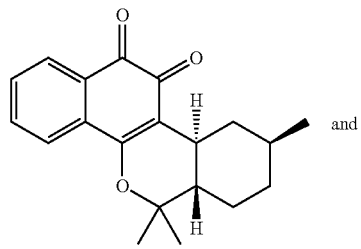

chiral

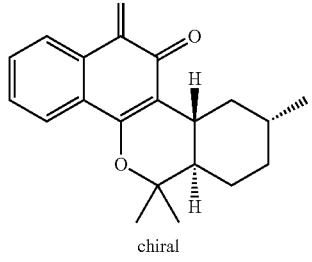

chiral

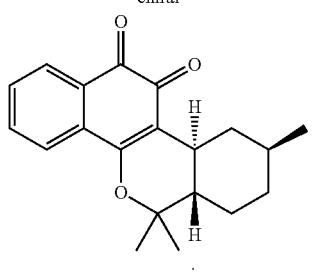

non racemic means a non racemic mixture of

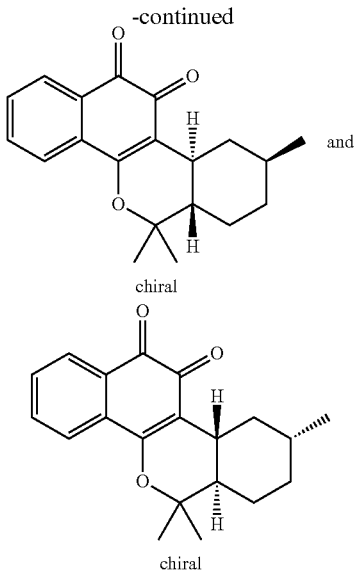

The compounds of the invention may be in the form of pharmaceutically acceptable salts. Pharmaceutically acceptable salts of the compounds of formula I include the acid addition and base salts thereof. Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts. Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine, 2-(diethylamino)ethanol, ethanolamine, morpholine, 4-(2-hydroxyethyl)morpholine and zinc salts. Hemisalts of acids and bases may also be formed, for example, hemisulphate and hemicalcium salts. Preferred, pharmaceutically acceptable salts include hydrochloride/chloride, hydrobromide/bromide, bisulphate/sulphate, nitrate, citrate, and acetate.

When the compounds of the invention contain an acidic group as well as a basic group, the compounds of the invention may also form internal salts, and such compounds are within the scope of the invention. When the compounds of the invention contain a hydrogen-donating heteroatom (e.g. NH), the invention also covers salts and/or isomers formed by transfer of said hydrogen atom to a basic group or atom within the molecule.

Pharmaceutically acceptable salts of compounds of Formula I may be prepared by one or more of these methods:

(i) by reacting the compound of Formula I with the desired acid;

(ii) by reacting the compound of Formula I with the desired base;

(iii) by removing an acid- or base-labile protecting group from a suitable precursor of the compound of Formula I or by ring-opening a suitable cyclic precursor, for example, a lactone or lactam, using the desired acid; or (iv) by converting one salt of the compound of Formula I to another by reaction with an appropriate acid or by means of a suitable ion exchange column.

All these reactions are typically carried out in solution. The salt, may precipitate from solution and be collected by filtration or may be recovered by evaporation of the solvent. The degree of ionization in the salt may vary from completely ionized to almost non-ionized.

The term "solvate" is used herein to describe a molecular complex comprising the compound of the invention and one or more pharmaceutically acceptable solvent molecules, for example, ethanol. The term 'hydrate' is employed when said solvent is water.

All references to compounds of formula I include references to salts, solvates, multi-component complexes and liquid crystals thereof.

The compounds of the invention include compounds of formula I as hereinbefore defined, including all polymorphs and crystal habits thereof, prodrugs and isomers thereof (including optical, geometric and tautomeric isomers) and isotopically-labeled compounds of formula I.

In addition, although generally, with respect to the salts of the compounds of the invention, pharmaceutically acceptable salts are preferred, it should be noted that the invention in its broadest sense also included non-pharmaceutically acceptable salts, which may for example be used in the isolation and/or purification of the compounds of the invention. For example, salts formed with optically active acids or bases may be used to form diastereoisomeric salts that can facilitate the separation of optically active isomers of the compounds of Formula I above.

The invention also generally covers all pharmaceutically acceptable prodrugs of the compounds of Formula I.

The term "prodrug" as used herein means the pharmacologically acceptable derivatives of compounds of formula I such as esters whose in vivo biotransformation product is the active drug. Prodrugs are characterized by increased bioavailability and are readily metabolized into the active compounds in vivo.

Within the meaning of the invention any atom of the compounds of the invention may present as any of its isotopes. In particular, any hydrogen atom may be tritium and any F, I or Br radical may be Particular embodiments of this aspect of the invention are those in which the radioisotope is selected from $^{18}F$, $^{123}I$, $^{125}I$, $^{131}I$, $^{75}Br$, $^{76}Br$, $^{77}Br$ or $^{82}Br$. A most particular embodiment of this aspect of the invention is that in which the radioisotope is $^{123}I$, $^{125}I$, $^{131}I$.

The term "cancer" includes solid tumors as well as hematologic cancers.

The term anti-cancer agent as used herein refers to any compound that reduces proliferation and/or division, and/or promotes death of cells participating in cancer progression including cancer cells.

The term anti-tumor agent as used herein refers to any compound that reduces tumor cell proliferation and/or division, and/or promotes tumor cell death.

The term anti-angiogenic agent as used herein refers to any compound that reduces endothelial cell proliferation and/or division.

The term "patient" refers to a warm-blooded animal, more preferably a human, who/which is awaiting or receiving medical care or is or will be the object of a medical procedure.

The term "human" refers to subject of both genders and at any stage of development (i.e. neonate, infant, juvenile, adolescent, adult).

The terms "treat", "treating" and "treatment, as used herein, are meant to include alleviating or abrogating a condition or disease and/or its attendant symptoms.

The term "therapeutically effective amount" (or more simply an "effective amount") as used herein means the amount of active agent or active ingredient (e.g. GPR43 modulator) which is sufficient to achieve the desired therapeutic or prophylactic effect in the individual to which it is administered.

The term "administration", or a variant thereof (e.g., "administering"), means providing the active agent or active ingredient (e.g. a GPR43 modulator), alone or as part of a pharmaceutically acceptable composition, to the patient in whom/which the condition, symptom, or disease is to be treated or prevented.

By "pharmaceutically acceptable" is meant that the ingredients of a pharmaceutical composition are compatible with each other and not deleterious to the patient thereof.

The term "hypoxic conditions" as used herein means an oxygen content of 1% v/v or less in the environment.

The present invention will be better understood with reference to the following examples. These examples are intended to representative of specific embodiments of the invention, and are not intended as limiting the scope of the invention.

CHEMISTRY EXAMPLES

Abbreviations and Acronyms

A comprehensive list of the abbreviations used by organic chemists of ordinary skill in the art appears in The ACS Style Guide (third edition) or the Guidelines for Authors for the Journal of Organic Chemistry. The abbreviations contained in said lists, and all abbreviations utilized by organic chemists of ordinary skill in the art are hereby incorporated by reference. For purposes of this invention, the chemical elements are identified in accordance with the Periodic Table of the Elements, CAS version, Handbook of Chemistry and Physics, 67th Ed., 1986-87.

More specifically, when the following abbreviations are used throughout this disclosure, they have the following meanings;
Bs: broad singlet,
d: doublet,
td: triplet of doublet
m: multiplet,
q: quartet
DCI-MS: direct chemical ionisation mass spectroscopy,
dd: doublet of doublet,
NMR: nuclear magnetic resonance,
s: singlet,
t: triplet,
NHS: N-hydroxysuccinimide,
EDCI:
EtOAc: ethylacetate,
PE: petroleum ether,
DCM: dichloromethane,
AcOH: acetic acid,
mol: mole(s),
mmol: millimole(s),
equiv.: equivalent(s),
ml: milliliter(s),
min.: minute(s),
h: hour(s),
EDCI: 1-ethyl-3-(3-dimethylaminopropyl) carbodiimide,
THF: tetrahydrofuran.

The percentage yields reported in the following examples are based on the starting component that was used in the lowest molar amount. Air and moisture sensitive liquids and solutions were transferred via syringe or cannula, and introduced into reaction vessels through rubber septa. Commercial grade reagents and solvents were used without further purification. All temperatures are reported uncorrected in degrees Celsius (° C.). The structures of compounds of this invention were confirmed using one or more of the following procedures.

NMR spectra were acquired for each compound and were consistent with the structures shown.

Routine one-dimensional NMR spectroscopy was performed on either 300 MHz and 500 MHz Bruker spectrometers. The samples were dissolved in deuterated solvents. Chemical shifts δ were recorded on the ppm (party per million) scale and were referenced to the appropriate solvent signals, such as 7.26 ppm for CDCI$_3$ for 1H spectra.

Mass analyses were performed on a FinniganMat TSQ7000 or a Thermo Scientific LTQ orbitrap XL mass spectrometer.

Solvents, reagents and starting materials were purchased from well known chemical suppliers Solvents, reagents and starting materials were purchased from well known chemical suppliers such as for example Sigma Aldrich, Acros Organics, TCI Europe.

Example 1

Compounds 1 and 1'

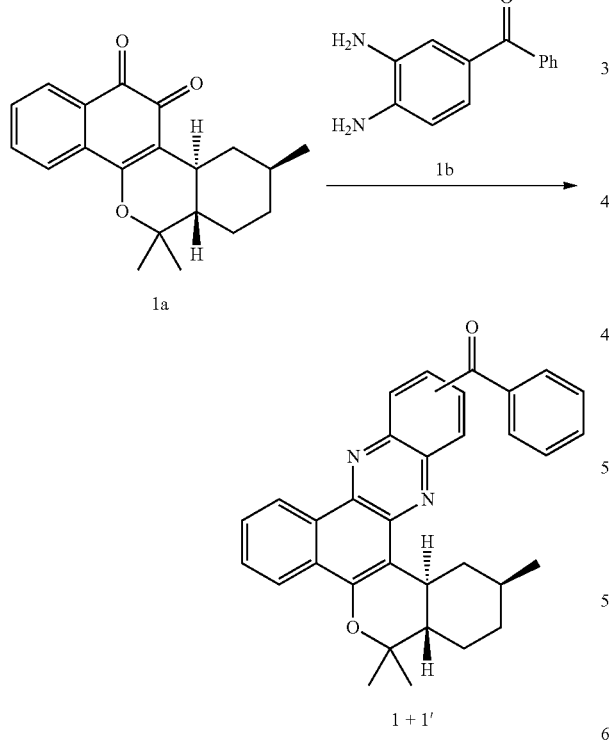

A solution of quinone 1a (prepared as racemic (unless otherwise stated) according to: *J. Med. Chem.* 2008, 51, 6761-6772) (62 mg, 0.2 mmol), diamine 1b (88 mg, 0.42 mmol, 2.1 equiv.) and sodium acetate (102 mg, 1.25 mmol, 6.3 equiv.) in 2.4 ml of acetic acid was stirred at 100° C. for 3 h. The reaction mixture was cooled and extracted with dichloromethane. After standard work-up, the crude reaction mixture was purified by flash-chromatography on silica gel (PE/EtOAc: 8/2). The product was isolated as a mixture of regioisomers 1 and 1' in a 72% yield (yellow solid).

[MH$^+$]: 441.21

Example 2

Compounds 2 and 2'

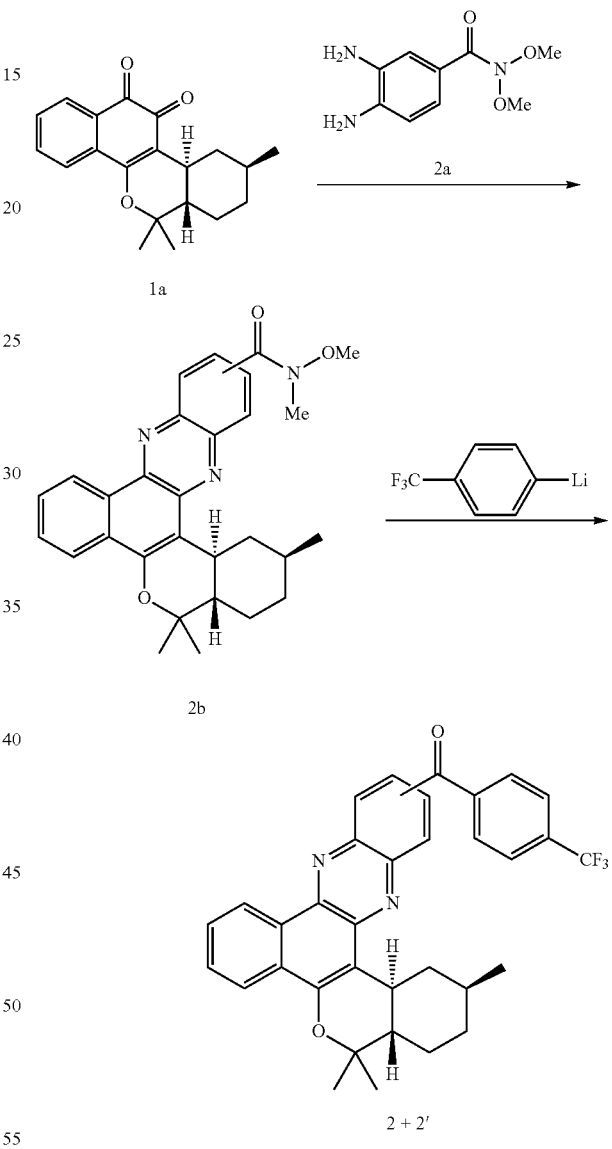

Synthesis of Weinreb Amide 2b:

Diamine 2a was prepared from 3,4-dinitrobenzoic acid according to the literature procedure (*J. Org. Chem.*, 2006, 71, 125-134) (1. SOCl$_2$, 80° C., 3 h. 2. CH$_3$ONHCH$_3$.HCl, Pyridine, CH$_2$Cl$_2$, 0° C.-25° C., 3.5 h. 3. H$_2$, 5% Pd/C, MeOH, 25° C., 3.5 h).

A solution of quinone 1a (116 mg, 0.37 mmol), diamine 2a (153 mg, 0.78 mmol, 2.1 equiv.) and sodium acetate (210 mg, 2.35 mmol, 6.3 equiv.) in 5 ml acetic acid was stirred at 100° C. for 2 h. The reaction mixture was cooled and extracted with dichloromethane. After standard work-up, the crude reaction mixture was purified by flash-chromatography on silica gel (PE/EtOAc: 9/3 to 8/22 to 7/3). The product 2b was isolated as a mixture of regioisomers in a 83% yield (orange-yellow solid).

Synthesis of Compounds 2 and 2':

To a cooled (−78° C.) solution of p-bromo trifluoromethylbenzene (215 mg, 0.96 mmol, 3 equiv.) in 4 ml of freshly distilled THF was added 1.25 ml of 1.6 M tert-butyl lithium (1.98 mmol, 6.2 equiv.) dropwise. The solution was stirred for 15 min. and the flask was transferred in an ice bath. Solid amide 2b (150 mg, 0.32 mmol, 1 equiv.) was added in one portion under argon flux and the solution was stirred for two hours at this temperature. The reaction mixture was quenched with 1M HCl and extracted with dichloromethane. After standard work up, the crude reaction mixture was purified by flash chromatography on silica gel (PE/Et$_2$O: 9/1). The desired compound was isolated as a mixture of regioisomers in a 35% yield. One regioisomer could be separated by crystallisation in PE/CH$_2$Cl$_2$. The mother liquors were concentrated and crystallized in PE to afford a sample of the second regioisomer.

[MH$^+$]: 555.54 added 1.25 ml of 1.6 M tert-butyl lithium (1.98 mmol, 6.2 equiv.) dropwise. The solution was stirred for 15 min. and the flask was transferred to an ice bath. Solid amide 2b (150 mg, 0.32 mmol, 1 equiv.) was added in one portion under argon flux and the solution was stirred for one hour at this temperature. The reaction mixture was quenched with 1 M HCl and extracted with dichloromethane. After standard work up, the crude reaction mixture was purified by flash chromatography on silica gel (PE/Et$_2$O: 8/2). A mixture of regioisomers 3 and 3' was isolated in a 41% yield (yellow solid).

[MH$^+$]: 488.33

Example 4

Compounds 5 and 5'

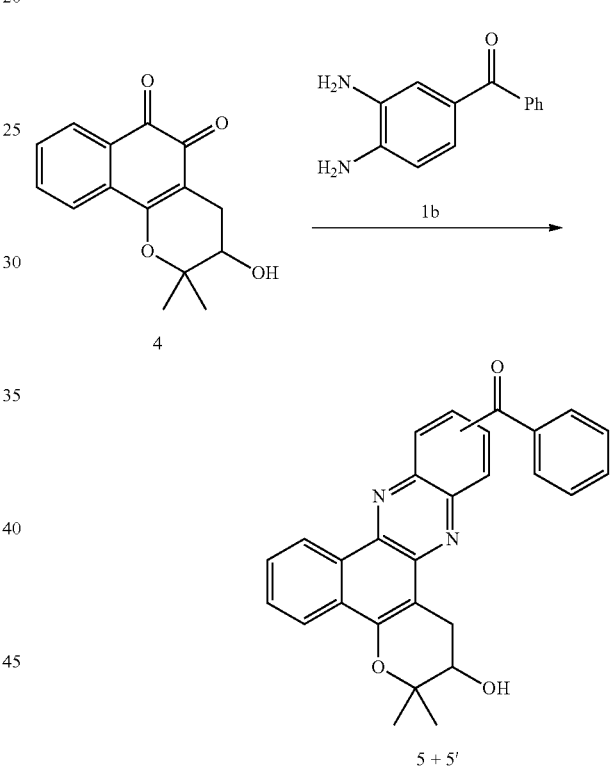

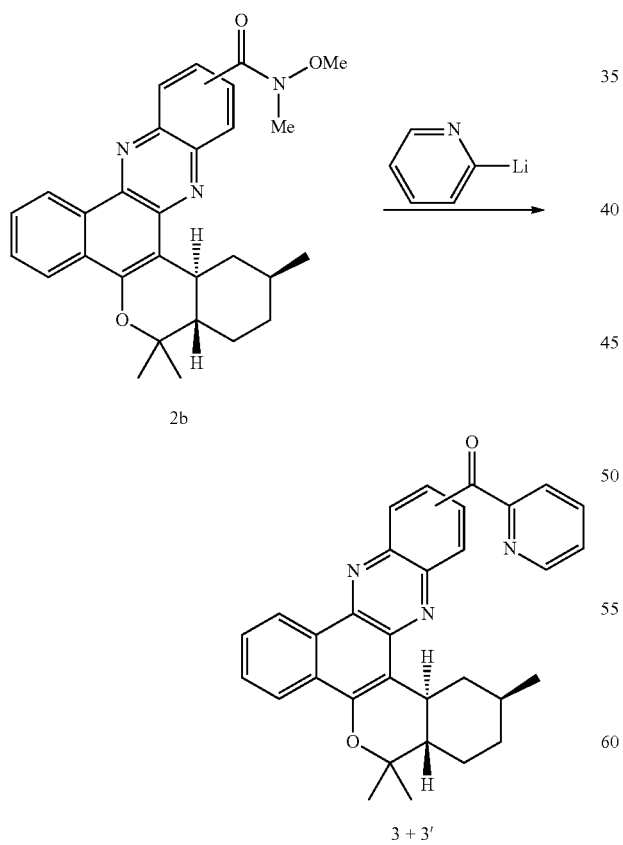

Example 3

Compounds 3 and 3'

To a cooled (−78° C.) solution of 2-bromopyridine (152 mg, 0.96 mmol, 3 equiv.) in 4 ml of freshly distilled THF was A suspension of hydroxy-lapachone 4 (prepared according to: *Tetrahedron Letters* 39 (1998) 8221-8224) (100 mg, 0.38 mmol), diamine 1b (172 mg, 0.81 mmol, 2.1 equiv.) and sodium acetate (197 mg, 2.44 mmol, 6.3 equiv.) in 4.6 ml acetic acid was stirred 100° C. for 4 h. The reaction mixture was cooled and extracted with dichloromethane. After standard work-up, the crude reaction mixture was purified by flash-chromatography on silica gel (PE/EtOAc: 7/3). A mixture of regioisomers 5 and 5' was isolated in a 43% yield (yellow solid).

[MH$^+$]: 435.37

Example 5

Compounds 7 and 7'

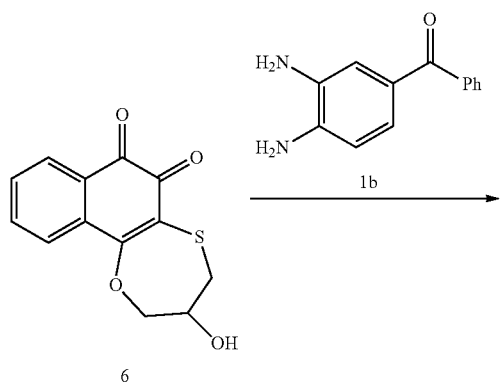

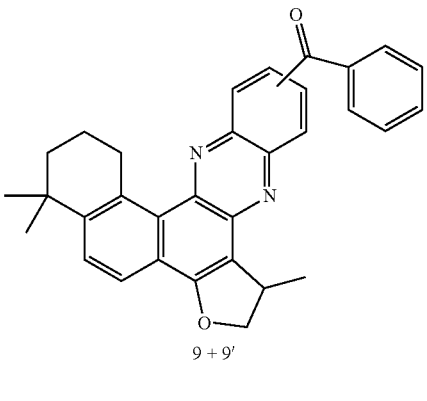

A solution of quinone 6 (prepared according to: WO2009/051752 A1) (50 mg, 0.19 mmol), diamine 1b (85 mg, 0.4 mmol, 2.1 equiv.) and sodium acetate (100 mg, 1.2 mmol, 6.3 equiv.) in 3 ml acetic acid was stirred 100° C. for 2 h. The reaction mixture was cooled and extracted with dichloromethane. After standard work-up, the crude reaction mixture was purified by flash-chromatography on silica gel (PE/EtOAc: 6/4). A mixture of regioisomers 7 and 7' was isolated in a 65% yield (yellow solid).

[MH$^+$]: 439.04

Example 6

Compounds 9 and 9'

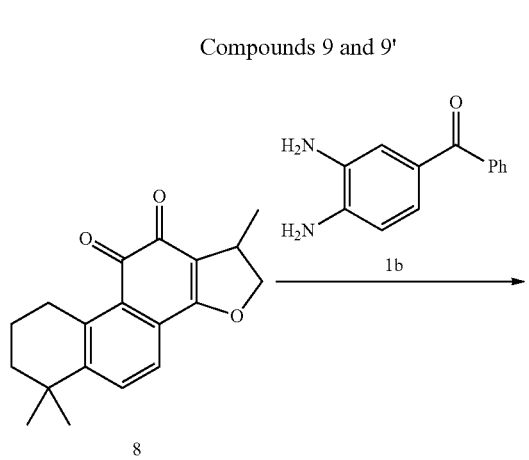

A solution of cryptotanshinone 8 (purchased from Aldrich) (25 mg, 0.08 mmol), diamine 1b (38 mg, 0.17 mmol, 2.1 equiv.) and sodium acetate (43 mg, 0.53 mmol, 6.3 equiv.) in 1 ml acetic acid was stirred 100° C. for 2 h. The reaction mixture was cooled and extracted with dichloromethane. After standard work-up, the crude reaction mixture was purified by flash-chromatography on silica gel (PE/EtOAc: 8/2). The two regioisomers 9 and 9' were separated and obtained as yellow solids in 51% (first eluting isomer) and 35% (second eluting isomer) yields.

[MH$^+$]: 473.22

Example 7

Compounds 11 and 11'

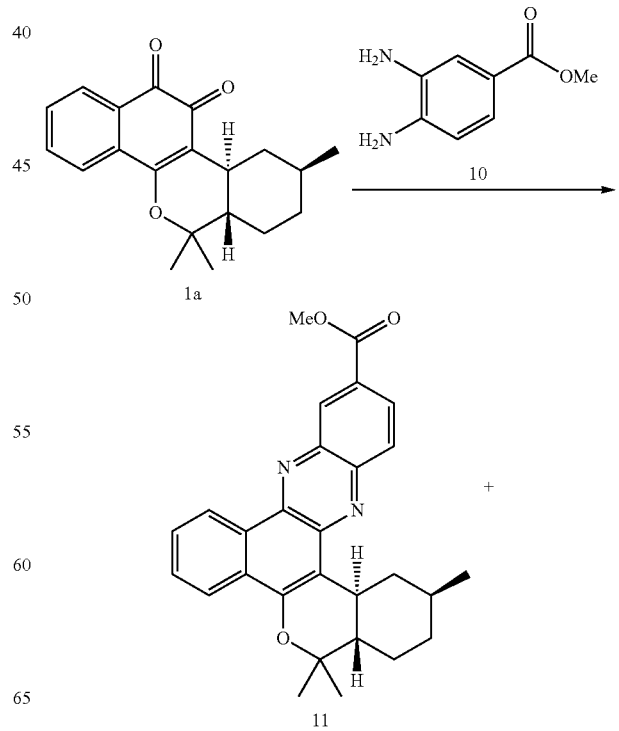

-continued

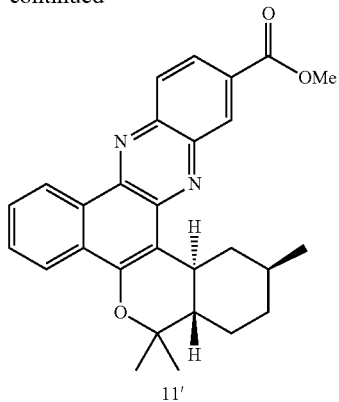

11'

A solution of racemic quinone 1a (500 mg, 1.6 mmol), diamine 10 (365 mg, 3.4 mmol, 2.1 equiv.) and sodium acetate (830 mg, 10 mmol, 6.3 equiv.) in 20 ml acetic acid was stirred 100° C. for 2 h. The reaction mixture was cooled and extracted with dichloromethane. After standard work-up, the crude reaction mixture was purified by flash-chromatography on silica gel (PE/EtOAc: 8/2). A mixture of regioisomers 11 and 11' was isolated in a 80% yield (yellow solid).

The solid was solubilized in a minimum amount of dichloromethane and ethyl acetate was added to the solution. The dichloromethane was eliminated by rotatory evavoration with heating and the solution was left at room temperature to allow crystallisation. The solid was filtered and afforded regiosomer 11. The operation was repeated on the filtrate until the minor regioisomer become the major product as measured by $^1$H NMR. The filtrate was then concentrated and taken up in a minimum amount of dichloromethane. Methanol was added and the two layers solution was left at room temperature to allow the crystallisation of the second regioisomer 11'.

The synthesis was also carried out starting from the pure enantiomers of citronelal (TCI. The mixture of ester arising from (R)-(+)-citronelal will be labelled (R)-(11+11') and the mixture of ester arising from (S)-(−)-citronelal will be labelled (S)-(11+11').

MS for both isomers: [MH$^+$]: 441.21

$^1$H NMR Data for Compound 11:

The structure was attributed by X-ray crystallography. Crystals were obtained by slow diffusion of pentane to a THF solution of compound 11.

11

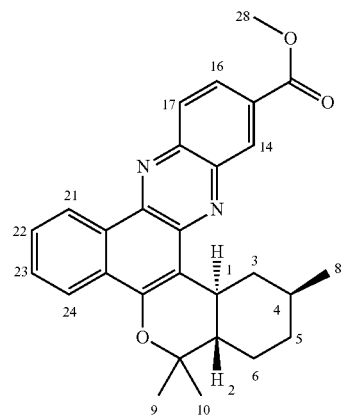

$^1$H NMR (300 MHz, CDCl$_3$) δ 9.31 (m, 1H, H$_{21}$), 8.94 (s, 1H, H$_{17}$), 8.31 (m, 3H, H$_{24}$, H$_{15}$, H$_{14}$), 7.77 (m, 2H, H$_{22}$ and H$_{23}$), 4.05 (s, 3H, H$_{28}$), 3.68 (d, J=12.4 Hz, 1H, H$_{3e}$), 3.13 (td, J=10.9, 2.4 Hz, 1H, H$_1$), 2.00 (s, 1H, H$_4$), 1.97 (m, 2H, H$_{5a}$ et H$_{6a}$), 1.74 (td, J=11.3 Hz, 1.56 Hz, 1H, H$_2$), 1.63 (s, 3H, H$_9$ or H$_{10}$), 1.26 (m, 5H, H$_9$ or H$_{10}$ et H$_{5a}$ et H$_{6a}$), 1.01 (d, J=6.3 Hz, 3H, H$_8$), 0.72 (q, J=11.5 Hz, 1H, H$_{3a}$).

$^1$H NMR Data for Compound 11'

The structure was attributed by X-ray crystallography. Crystals were obtained by slow diffusion of methanol to a dichloromethane solution of 11'.

11'

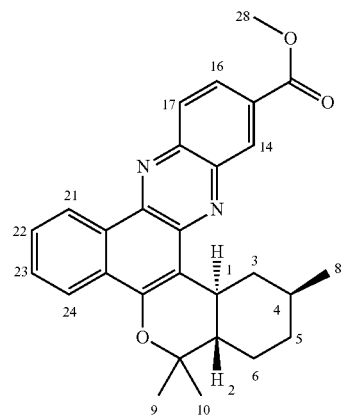

$^1$H NMR (300 MHz, CDCl$_3$) δ 9.31 (m, 1H, H$_{21}$), 9.02 (d, J=1.7 Hz, 0.8H, H$_{14}$), 8.94 (s, 0.2H, H$_{14}$), 8.31 (m, 3H, H$_{24}$, H$_{17}$, H$_{16}$), 7.78 (m, 2H, H$_{22}$ and H$_{23}$), 4.04 (s, 3H, H$_{28}$), 3.69 (m, 1H, H$_{3e}$), 3.13 (td, J=10.9, 2.5 Hz, 1H, H$_1$), 2.00 (s, 1H, H$_4$), 1.99 (m, 2H, H$_{5a}$ and H$_{6a}$), 1.74 (t, J=11.3 Hz, 1H, H$_2$), 1.63 (s, 3H, H$_9$ or H$_{10}$), 1.31 (m, 5H, H$_9$ or H$_{10}$ and H$_{5a}$ and H$_{6a}$), 0.99 (d, J=6.3 Hz, 3H, H$_8$), 0.72 (q, J=0.04 Hz, 1H, H$_{3a}$).

Example 8

Compound 12

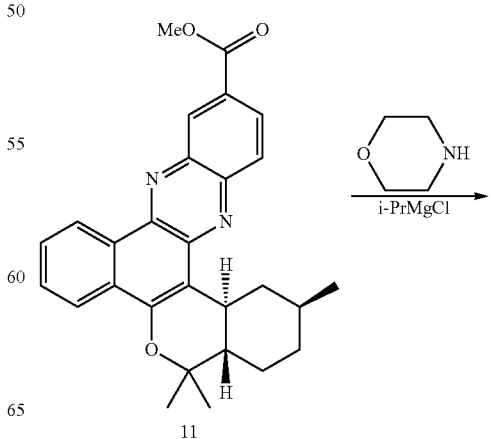

11

114

Example 9

Compound 12'

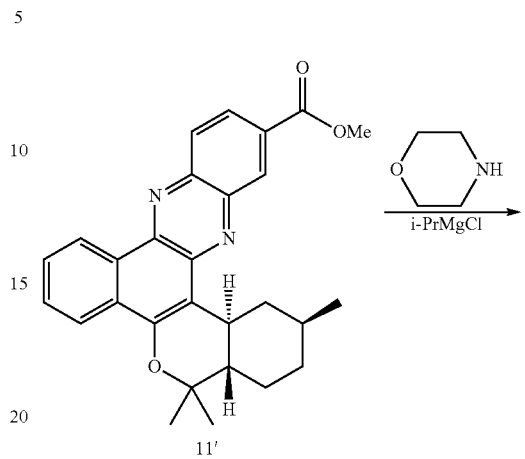

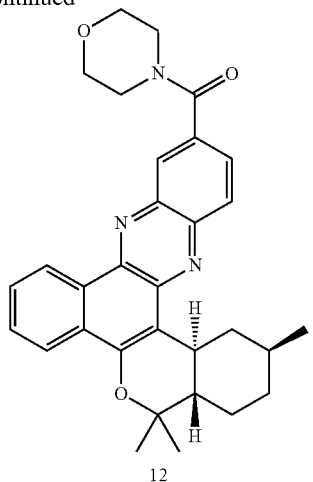

To a cooled (−20° C.) solution of phenazine ester 11 (75 mg, 0.19 mmol, 1 equiv.) in 2.5 mL of freshly distilled THF under argon was added morpholine (27 µL, 0.3, 1.55 equiv) followed by 375 µL of a 1.55 M isopropyl magnesium chloride (0.58 mmol, 3 equiv.). The reaction was stirred at −20° C. for 1 h before quenching with aqueous ammonium chloride solution. Extraction with diethyl ether and standard work up afforded the crude amide which was purified by filtration on a short pad of silica gel (PE/EtOAc: 8/2). The amide 12 was isolated as yellow solid in a 98% yield.

(12)

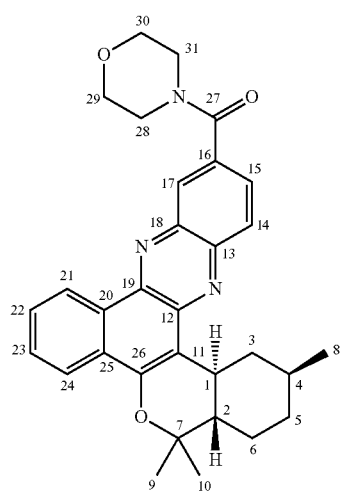

The same procedure as for racemic compound 12 was carried out starting from racemic ester 11' and afforded the amide 12' in a 98% yield.

(12')

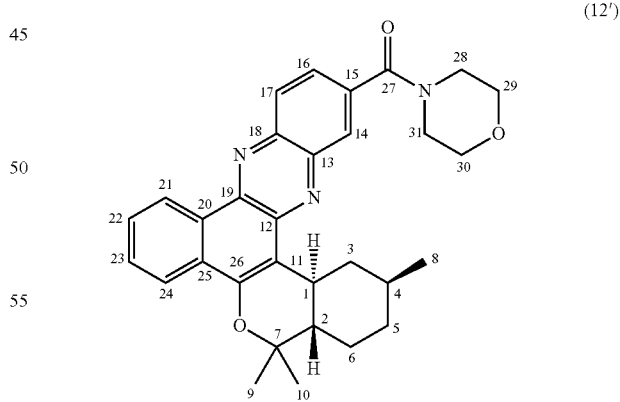

$^1$H NMR (300 MHz, CDCl$_3$) δ 9.29 (m, 1H, H$_{21}$), 8.29 (m, 3H, H$_{ar}$), 7.78 (m, 3H, H$_{ar}$), 3.70 (m, 9H, H$_{3e}$H$_{28}$H$_{29}$H$_{30}$H$_{31}$), 3.12 (m, 1H, H$_1$), 1.99 (s, 1H, H$_4$), 1.96 (s, 2H, H$_{5a}$ and H$_{6a}$), 1.73 (t, J=10.6 Hz, 1H, H$_2$), 1.62 (s, 3H, H$_9$ or H$_{10}$), 1.26 (m, 5H, H$_9$ or H$_{10}$ and H$_{5a}$ and H$_{6a}$), 0.98 (d, J=6.3 Hz, 3H, H$_8$), 0.70 (q, J=11.5 Hz, 1H, H$_{3a}$).

[MH$^+$]: 496.25

$^1$H NMR (300 MHz, CDCl$_3$) δ 9.29 (m, 1H, H$_{21}$), 8.29 (m, 3H, H$_{ar}$), 7.77 (m, 3H, H$_{ar}$), 3.70 (m, 9H, H$_{3e}$H$_{28}$H$_{29}$H$_{30}$H$_{31}$), 3.11 (m, 1H, H$_1$), 1.97 (s, 1H, H$_4$), 1.94 (s, 2H, H$_{5a}$ and H$_{6a}$), 1.71 (t, J=10.6 Hz, 1H, H$_2$), 1.61 (s, 3H, H$_9$ ou H$_{10}$), 1.23 (m, 5H, H$_9$ or H$_{10}$ and H$_{5a}$ and H$_{6a}$), 0.97 (d, J=6.3 Hz, 3H, H$_8$), 0.69 (q, J=11.5 Hz, 1H, H$_{3a}$).

[MH$^+$]: 496.25

115

The synthesis was also carried out starting from the pure enantiomers of citronelal (TCI. The mixture of amides arising from (R)-(+)-citronelal are labelled (R)-(12+12') and the mixture of amides arising from (S)-(-)-citronelal are labelled (S)-(12+12').

Example 10

Compounds 14 and 14'

116

Example 11

Compounds 15 and 15'

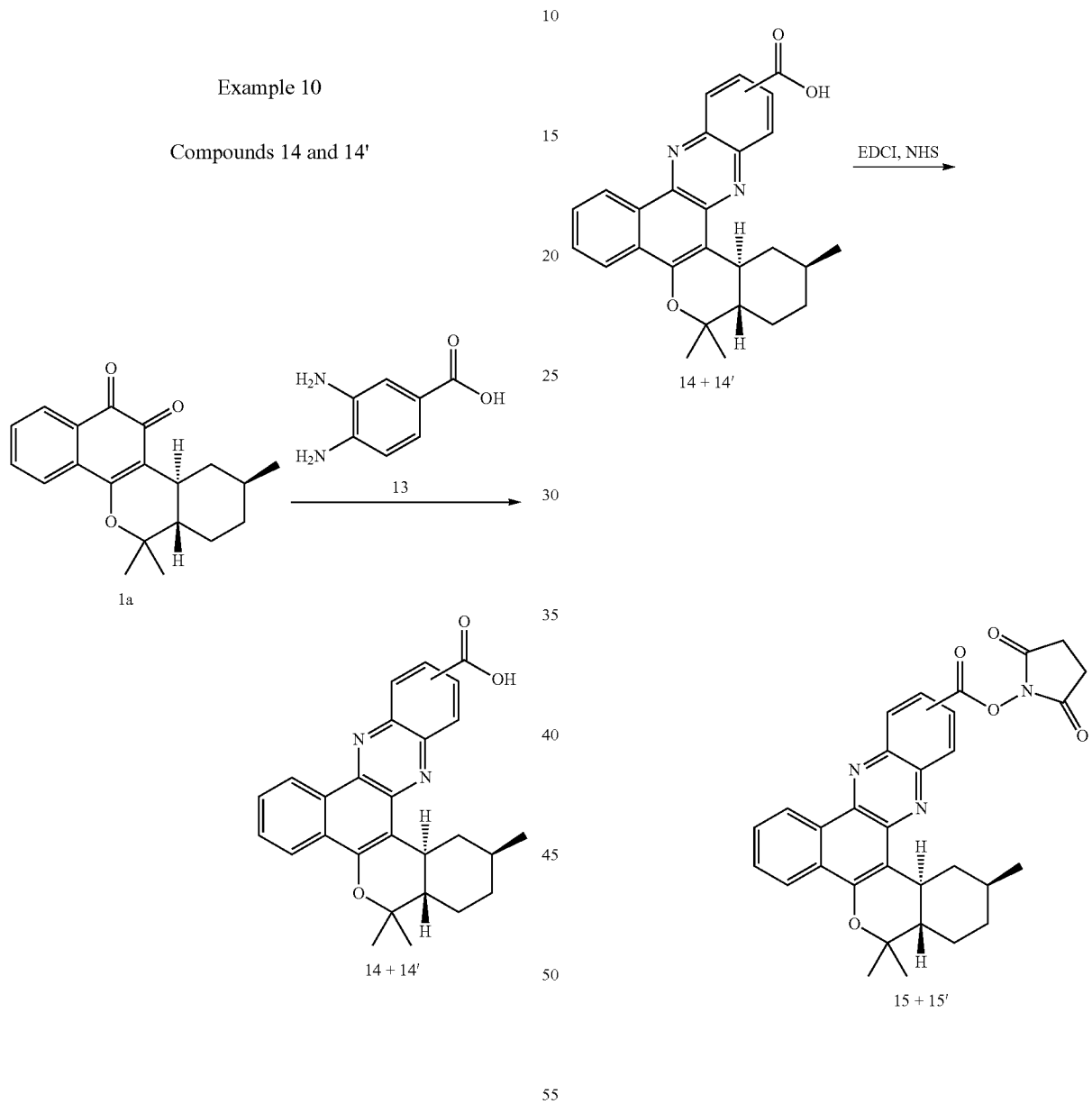

A solution of quinone 1a (100 mg, 0.32 mmol), diamine 13 (104 mg, 0.67 mmol, 2.1 equiv.) and sodium acetate (190 mg, 2.3 mmol, 6.3 equiv.) in 4 ml acetic acid was stirred 100° C. for 2 h. The reaction mixture was cooled and concentrated in vacuo. The crude product was purified by flash-chromatography on silica gel (PE/EtOAc/AcOH: 8/1.5/0.5). The product was isolated as a mixture of regioisomers in a 92% yield (yellow solid).

[MH+]: 427.25

The mixture of acids 14 and 14' (135 mg, 0.32 mmol) was suspended in 12 ml of dichloromethane under stirring. N-hydroxy succinimide (36 mg, 0.32 mmol, 1 equiv.) and EDCI (60 mg, 0.32 mg, 1 equiv) were successively added and the reaction mixture was stirred at room temperature for 36 h. The reaction mixture was washed with aqueous NaHCO$_3$ (5%) and brine. Standard work up afforded the crude product which was purified by flash chromatography on silicagel (EP/EtOAc: 8/2). The NHS esters were isolated as a yellow solid in a 97% yield).

[MH⁺]: 524.09

Example 12

Compounds 16 and 16'

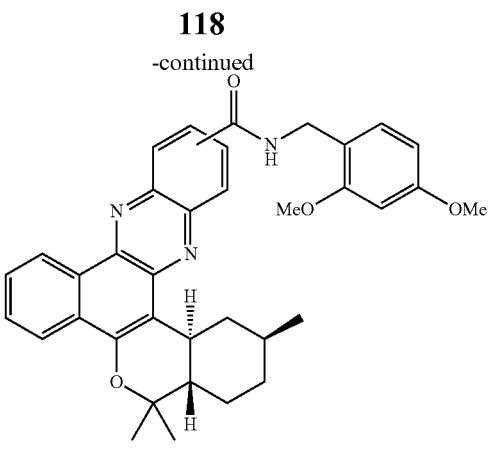

16 + 16'

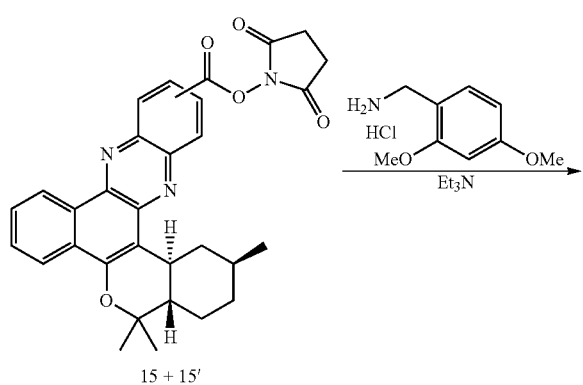

15 + 15'

To a solution of NHS esters 15 and 15' (80 mg, 0.15 mmol) in 3 ml of dichloromethane was added solid 2,4-dimethoxy benzylamine hydrochloride (31 mg, 0.15 mmol, 1 equiv) Under stirring. Triethylamine (20 μL, 0.15 mmol, 1 equiv.) was added and the reaction mixture was stirred at room temperature overnight. After concentration, the crude mixture was purified by flash chromatography on silica gel (PE/EtOAc: 8/2). The mixture of amides 16 and 16' was isolated as a yellow oil in a 80% yield.

[MH⁺]: 576

The synthesis was also carried out starting from the pure enantiomers of citronelal (TCI. The mixture of amides arising from (R)-(+)-citronelal are labelled (R)-(16+16') and the mixture of amides arising from (S)-(−)-citronelal are labelled (S)-(16+16').

Example 13

Compounds 17 and 17'

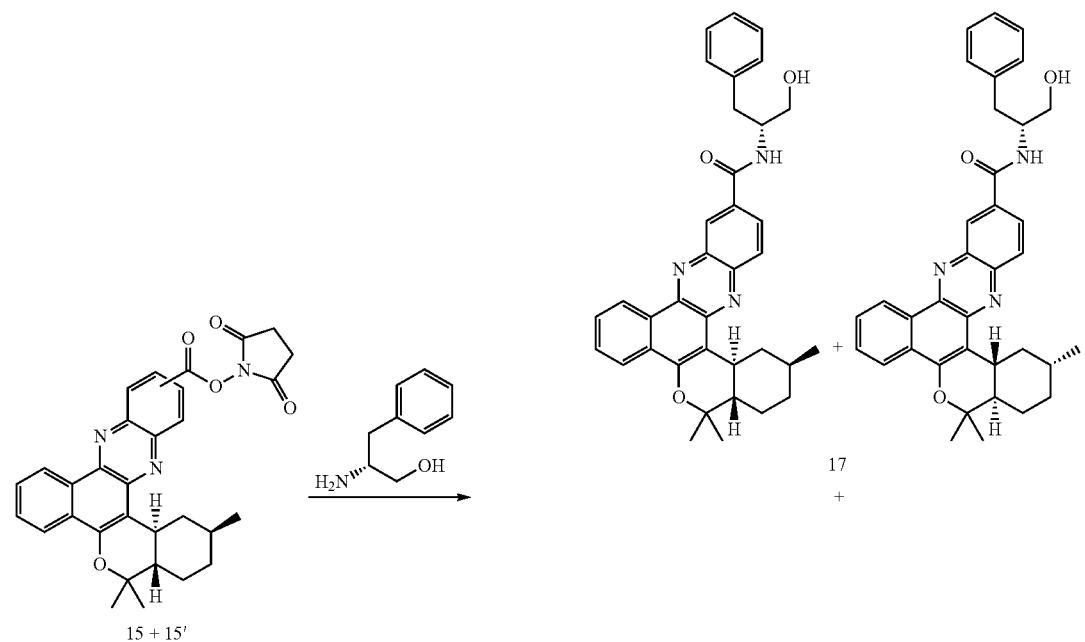

-continued

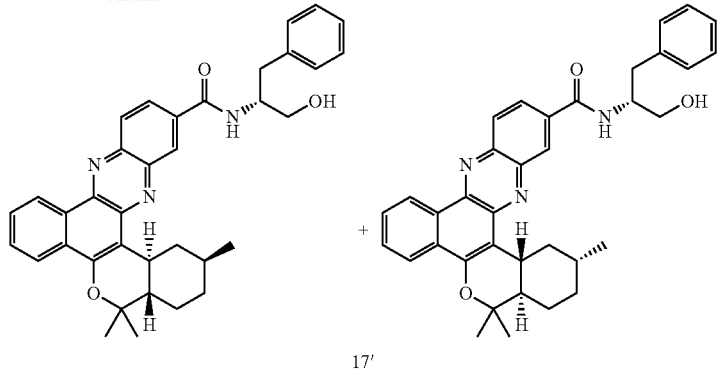

17'

To a solution of NHS esters 15 and 15' (50 mg, 0.095 mmol) in 2 ml of dichloromethane was added phenyl alaninol (32 mg, 0.21 mmol, 2.2 equiv) added and the reaction mixture was stirred at room temperature overnight. After concentration, the crude amide was purified by flash chromatography on silica gel (PE/EtOAc: 6/4). The mixture of amides 17 and 17' was isolated as a yellow solid in a 83% yield.

[MH$^+$]: 560.28

General Procedure for the Synthesis of the Pure Regioisomers: Compounds 16, 16', 17 and 17'

Example 14

Compound 16

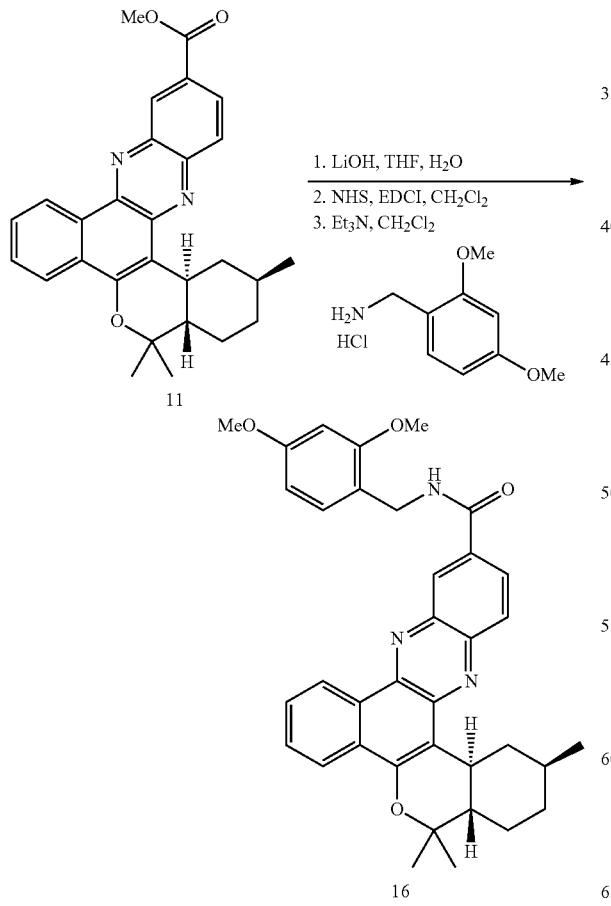

Ester 11 (120 mg, 0.31 mmol, 1 equiv.) and LiOH (702 mg, 16.7 mmol, 54 equiv.) are solubilised in 18 ml of THF and 8 ml of water. The reaction mixture is refluxed overnight and the THF was evaporated in vacuo. The aqueous phase was made acidic with 1M HCl and the acid was extracted with dichloromethane/THF. After standard work up, the crude acid was used in the activation step following the procedure described earlier to yield the pure NHS ester 15. Condensation with 2,4-dimethoxy benzylamine hydrochloride and triethylamine in dichloromethane gave the pure amide 16.

Data for Compound 16:

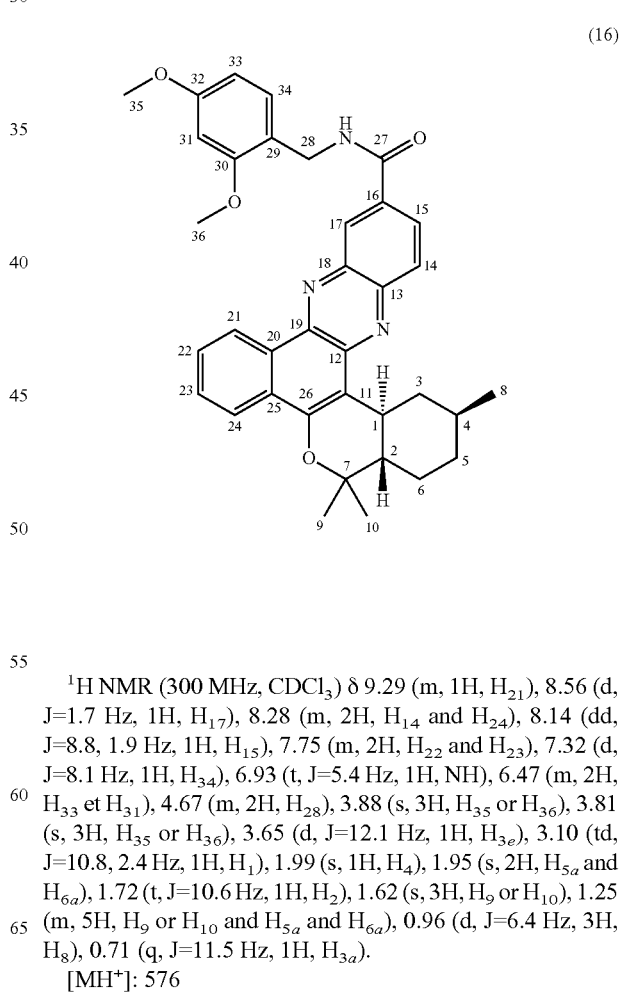

(16)

$^1$H NMR (300 MHz, CDCl$_3$) δ 9.29 (m, 1H, H$_{21}$), 8.56 (d, J=1.7 Hz, 1H, H$_{17}$), 8.28 (m, 2H, H$_{14}$ and H$_{24}$), 8.14 (dd, J=8.8, 1.9 Hz, 1H, H$_{15}$), 7.75 (m, 2H, H$_{22}$ and H$_{23}$), 7.32 (d, J=8.1 Hz, 1H, H$_{34}$), 6.93 (t, J=5.4 Hz, 1H, NH), 6.47 (m, 2H, H$_{33}$ et H$_{31}$), 4.67 (m, 2H, H$_{28}$), 3.88 (s, 3H, H$_{35}$ or H$_{36}$), 3.81 (s, 3H, H$_{35}$ or H$_{36}$), 3.65 (d, J=12.1 Hz, 1H, H$_{3e}$), 3.10 (td, J=10.8, 2.4 Hz, 1H, H$_1$), 1.99 (s, 1H, H$_4$), 1.95 (s, 2H, H$_{5a}$ and H$_{6a}$), 1.72 (t, J=10.6 Hz, 1H, H$_2$), 1.62 (s, 3H, H$_9$ or H$_{10}$), 1.25 (m, 5H, H$_9$ or H$_{10}$ and H$_{5a}$ and H$_{6a}$), 0.96 (d, J=6.4 Hz, 3H, H$_8$), 0.71 (q, J=11.5 Hz, 1H, H$_{3a}$).

[MH$^+$]: 576

Example 15

Compound 16'

An analogous procedure starting from ester 11' gave the pure amide isomer 16'

Data for Compound 16':

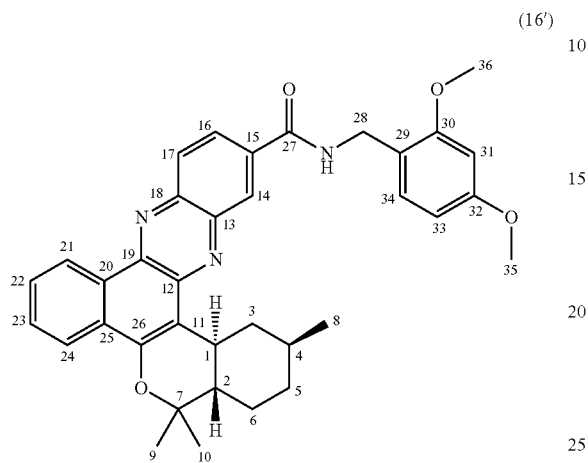

(16')

$^1$H NMR (300 MHz, CDCl$_3$) δ 9.29 (m, 1H, H$_{21}$), 8.56 (s, 1H, H$_{14}$), 8.24 (m, 3H, H$_{16}$, H$_{17}$ and H$_{24}$), 7.76 (m, 2H, H$_{22}$ et H$_{23}$), 7.34 (d, J=8.1 Hz, 1H, H$_{34}$), 6.89 (t, J=5.4 Hz, 1H, NH), 6.49 (m, 2H, H$_{33}$ and H$_{31}$), 4.67 (d, J=2.77 Hz, 2H, H$_{27}$), 3.91 (s, 3H, H$_{35}$ or H$_{36}$), 3.82 (s, 3H, H$_{35}$ ou H$_{36}$), 3.66 (t, J=12.1 Hz, 1H, H$_{3e}$), 3.12 (td, J=10.8, 2.4 Hz, 1H, H$_1$), 1.99 (s, 1H, H$_4$), 1.95 (s, 2H, H$_{5a}$ and H$_{6a}$), 1.72 (t, J=10.6 Hz, 1H, 1H, H$_2$), 1.62 (s, 3H, H$_9$ or H$_{10}$), 1.27 (m, 5H, H$_9$ or H$_{10}$ and H$_{5a}$ and H$_{6a}$), 0.99 (d, J=6.4 Hz, 3H, H$_8$), 0.71 (q, J=11.5 Hz, 1H, H$_{3a}$).

[MH$^+$]: 576

Example 16

Compound 17

An analogous procedure was used to prepare pure regioisomer compounds 17 starting from the corresponding ester 11 and 11' and phenyl alaninol:

Data for Compound 17:

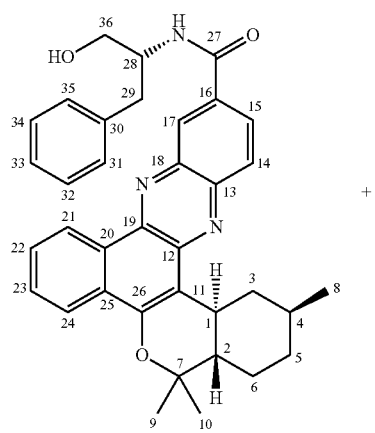

(17)

+

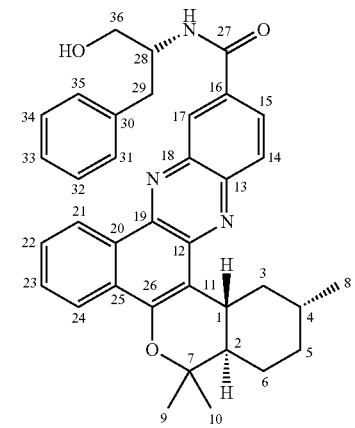

$^1$H NMR (300 MHz, CDCl$_3$) δ 9.24 (m, 1H, H$_{21}$), 8.43 (dd, J=5.9, 1.4 Hz, 1H, H$_{17}$), 8.27 (m, 2H, H$_{14}$, H$_{24}$), 8.04 (m, 1H, H$_{15}$), 7.74 (m, 2H, H$_{22}$ and H$_{23}$), 7.34 (m, 4H, H$_{31}$, H$_{32}$, H$_{34}$ and H$_{35}$), 7.28 (m, 1H, H$_{33}$), 6.72 (d, J=7.5 Hz, 1H, NH), 4.49 (m, 1H, H$_{28}$), 3.82 (m, 2H, C$_{36}$), 3.64 (d, J=12.0 Hz, 1H, H$_{3e}$), 3.12 (m, 3H, H$_{29}$ and H$_1$), 2.89 (s, 1H, OH), 1.98 (m, 3H, H$_4$, H$_{5a}$ et H$_{6a}$), 1.74 (t, J=11.0 Hz, 1H, H$_2$), 1.63 (s, 3H, H$_9$ or H$_{10}$), 1.30 (m, 5H, H$_9$ or H$_{10}$ and H$_{5a}$ and H$_{6a}$), 1.03 (d, J=6.1 Hz, 3H, H$_8$), 0.74 (q, J=11.4 Hz, 1H, H$_{3a}$).

[MH$^+$]: 560.28

Example 17

Compound 17'

An analogous procedure was used to prepare pure regioisomer compounds 17 starting from the corresponding ester 11 and 11' and phenyl alaninol:

Data for Compound 17':

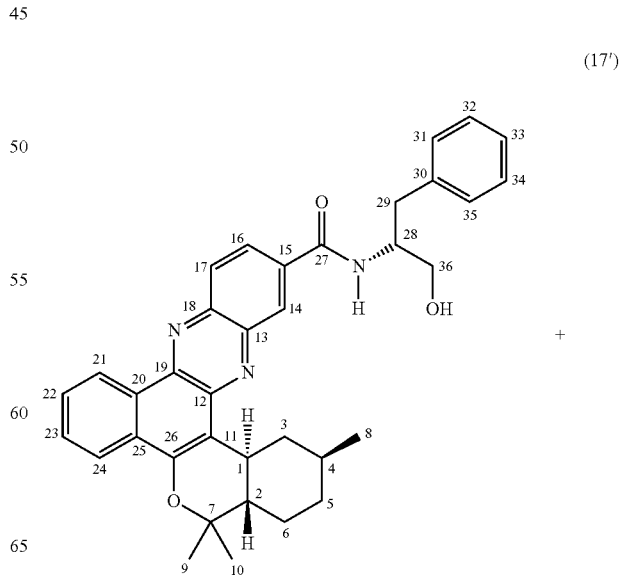

(17')

+

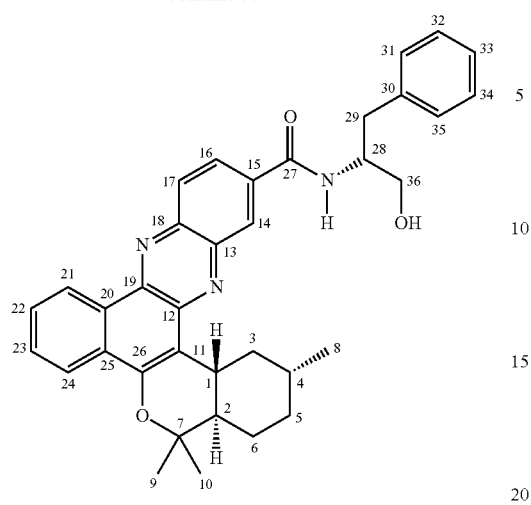

$^1$H NMR (300 MHz, CDCl$_3$) δ 9.16 (m, 1H, H$_{21}$), 8.51 (s, 0.7H, H$_{14}$), 8.43 (d, J=7.3 Hz, 0.3H, H$_{14}$), 8.26 (m, 1H, H$_{24}$), 8.08 (m, 2H, H$_{16}$ and H$_{17}$), 7.71 (m, 2H, H$_{22}$ and H$_{23}$), 7.32 (d, J=4.0 Hz, 4H, H$_{31}$, H$_{32}$, H$_{34}$ and H$_{35}$), 7.25 (m, 1H, H$_{33}$), 6.90 (m, 1H, NH), 4.50 (m, 1H, H$_{28}$), 3.83 (m, 2H, H$_{36}$), 3.64 (d, J=11.6 Hz, 1H, H$_{3e}$), 3.25 (s, 1H, OH), 3.09 (m, 3H, H$_{29}$ et H$_1$), 1.99 (s, 1H, H$_4$), 1.96 (s, 2H, H$_{5a}$ et H$_{6a}$), 1.70 (m, 1H, H$_2$), 1.62 (s, 3H, H$_9$ ou H$_{10}$), 1.3 (m, 5H, H$_9$ or H$_{10}$ et H$_{5a}$ and H$_{6a}$), 1.00 (m, 3H, H$_8$), 0.71 (m, 1H, H$_{3a}$).

[MH$^+$]: 560.28

Example 18

Compounds 18 and 18'

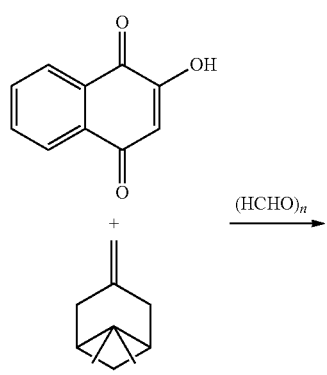

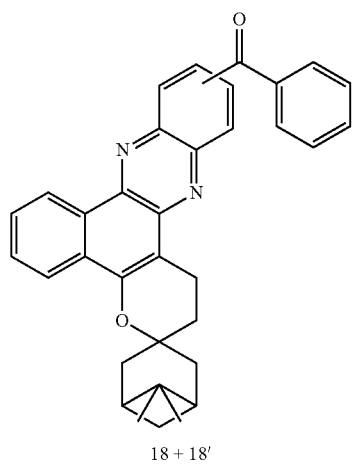

The quinone Q1 was prepared by condensation of hydroxy-naphthoquinone, paraformaldehyde and beta-pinene according to an analogous procedure described in *Biorg. Med. Chem.*, 2008, 16, 1328-1336. Condensation with diamine 1b was carried out with a similar procedure used for the preparation of 1+1' to yield a mixture of compounds 18 and 18'.

[MH$^+$]: 499.27

Example 19

Compounds 19 and 19'

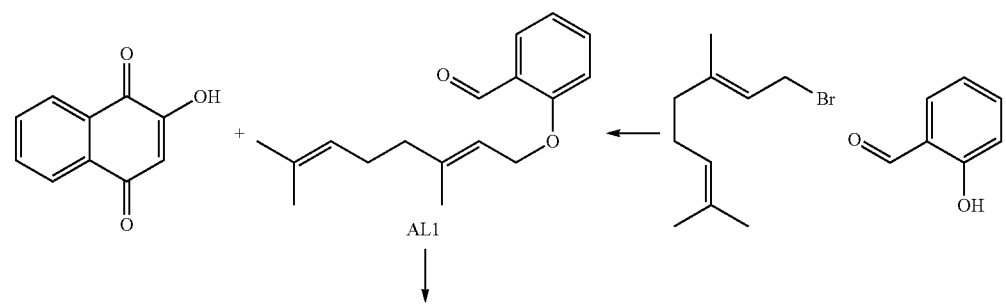

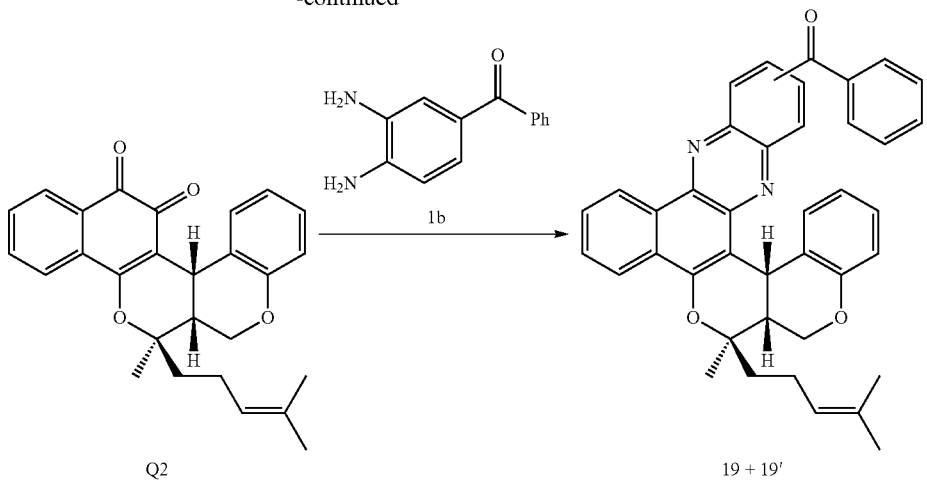

The quinone Q2 was prepared by condensation of hydroxy-naphthoquinone and aldehyde AU according to the general procedure described in *J. Med. Chem.*, 2008, 51, 6761-6772. The starting aldehyde was prepared according to the procedure described in *Tetrahedron*, 2009, 65, 101-108 by condensation of geranyl bromide and salicyladehyde. Condensation with diamine 1b was carried out with a similar procedure used for the preparation of 1+1' to yield a mixture of compounds 19 and 19'.

[MH$^+$]: 591.14

Example 20

Compounds 20 and 20'

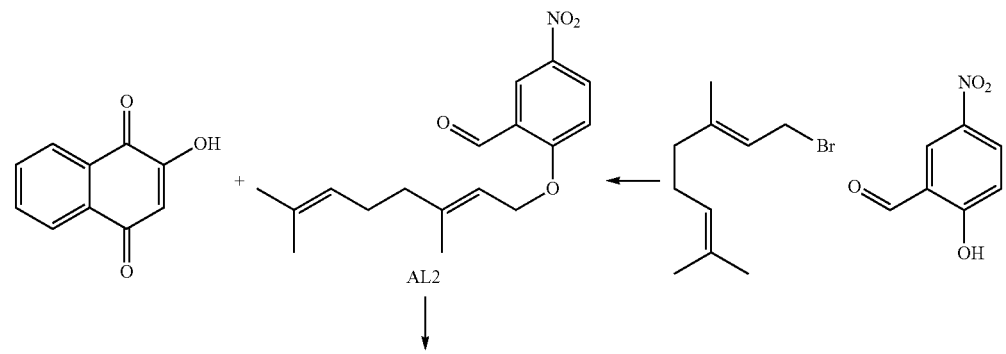

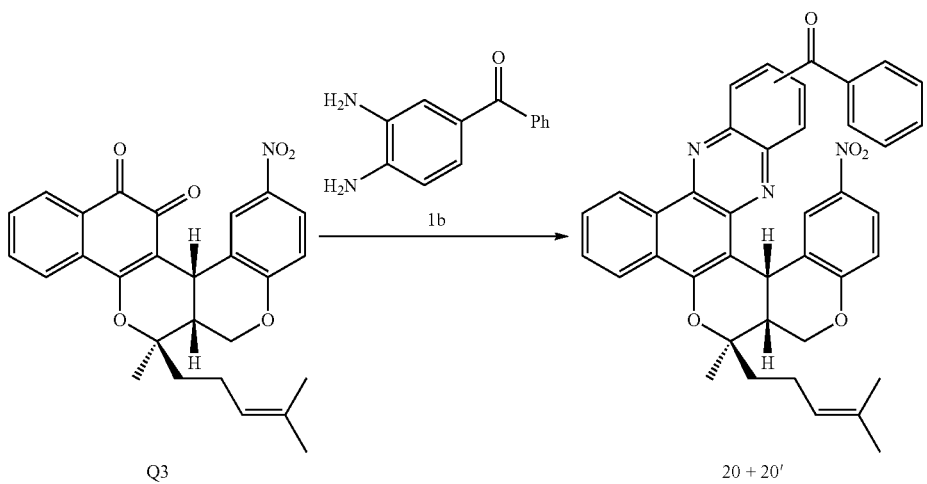

The quinone Q3 was prepared by condensation of hydroxy-naphthoquinone, and aldehyde AL2 according to the general procedure described in *J. Med. Chem.*, 2008, 51, 6761-6772. The starting aldehyde was prepared according to the procedure described in *Tetrahedron*, 2009, 65, 101-108 by condensation of geranyl bromide and 3-nitro-salicyladehyde. Condensation with diamine 1b was carried out with a similar procedure used for the preparation of 1+1' to yield a mixture of compounds 20 and 20'.

[MH⁺]: 635.40

Example 21

Compounds 22 and 22'

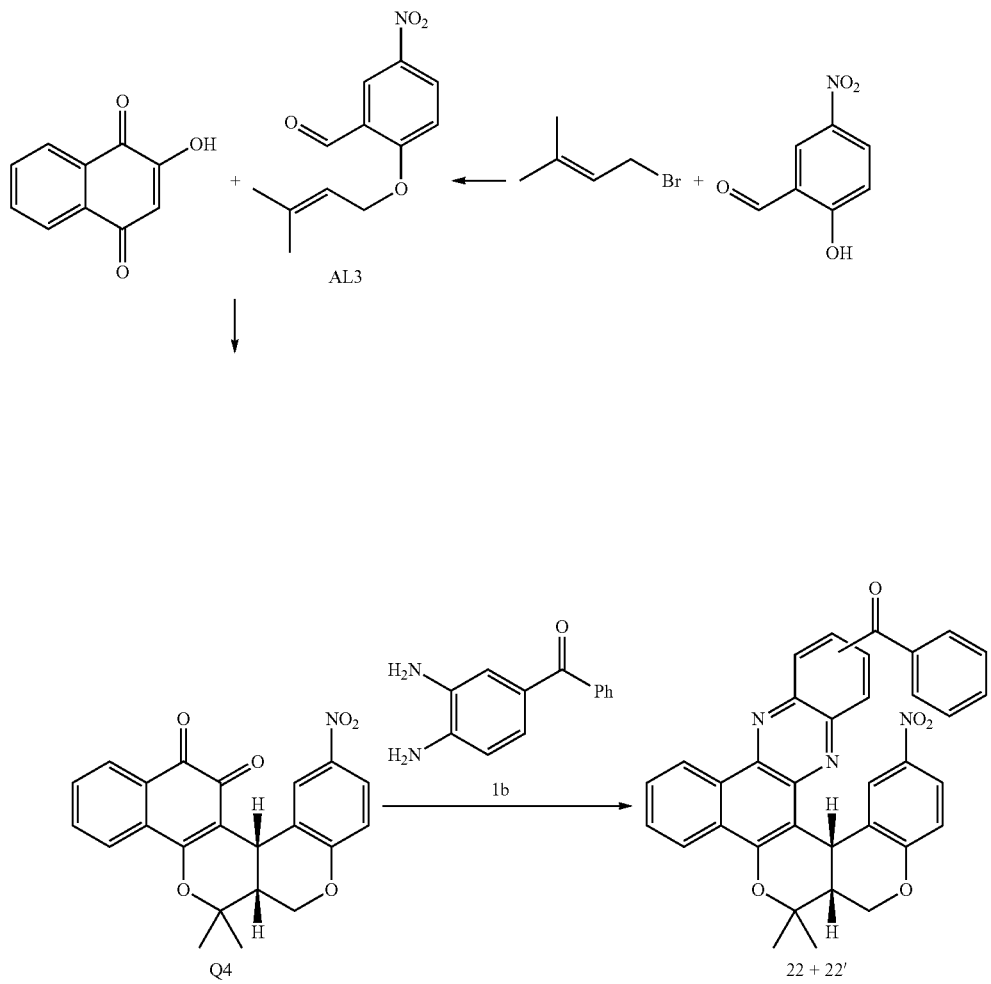

The quinone Q4 was prepared by condensation of hydroxy-naphthoquinone, and aldehyde AL3 according to the general procedure described in *J. Med. Chem.*, 2008, 51, 6761-6772. The starting aldehyde was prepared according to the procedure described in *Tetrahedron*, 2009, 65, 101-108 by condensation of methalyl bromide and 3-nitro-salicyladehyde. Condensation with diamine 1b was carried out with a similar procedure used for the preparation of 1+1' to yield a mixture of compounds 22 and 22'.

[MH⁺]: 568.05

Example 22

Compounds 23 and 23'

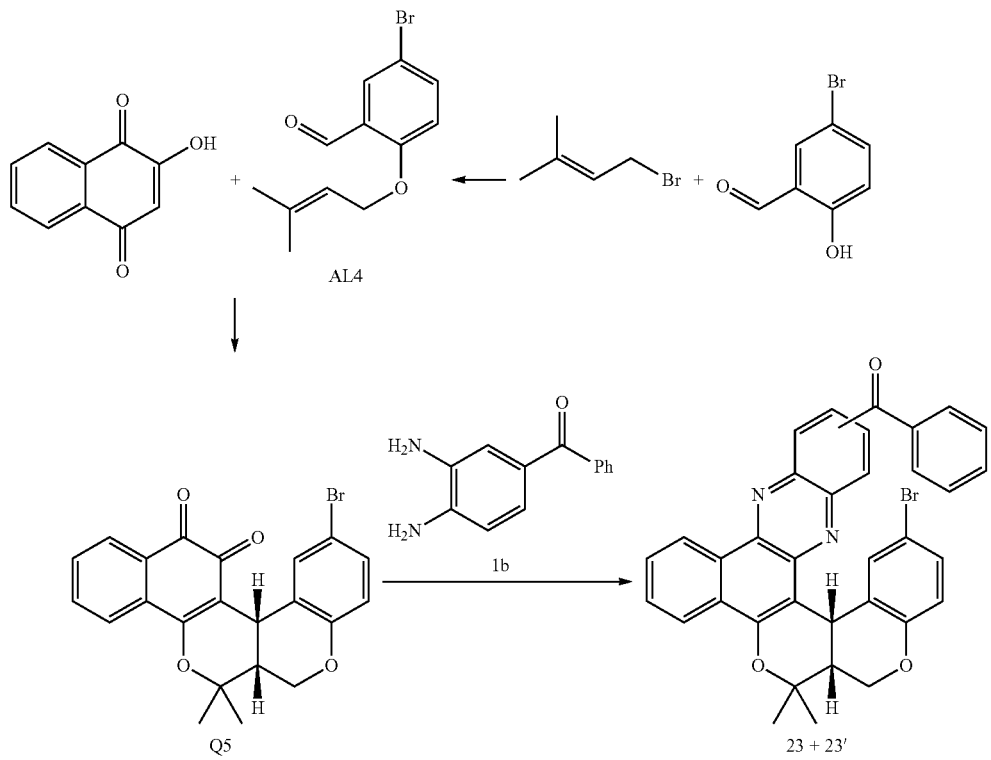

The quinone Q5 was prepared by condensation of hydroxy-naphthoquinone, and aldehyde AL4 according to the general procedure described in *J. Med. Chem.,* 2008, 51, 6761-6772. The starting aldehyde was prepared according to the procedure described in *Tetrahedron,* 2009, 65, 101-108 by condensation of methalyl bromide and 3-bromo-salicylade-hyde. Condensation with diamine 1b was carried out with a similar procedure used for the preparation of 1+1' to yield a mixture of compounds 23 and 23'.

[MH$^+$]: 601.08

Example 23

Compounds 24 and 24'

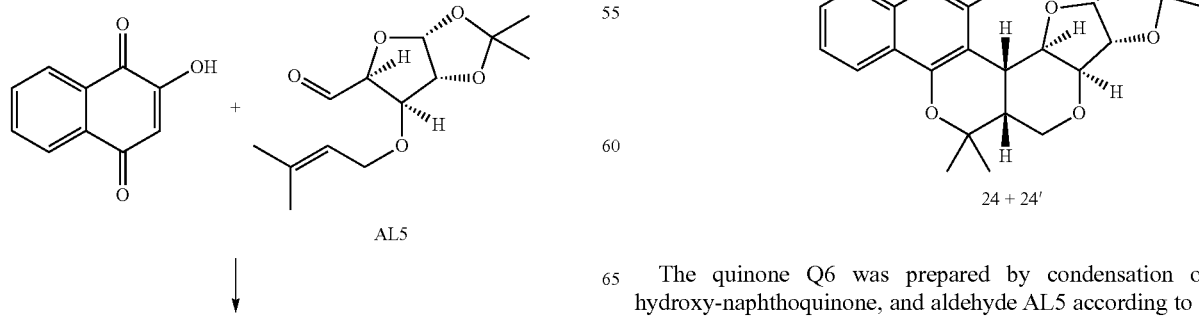

The quinone Q6 was prepared by condensation of hydroxy-naphthoquinone, and aldehyde AL5 according to a similar procedure described in Tetrahedron Lett., 2004, 45, 3493-3497. Condensation with diamine 1b was carried out with a similar procedure used for the preparation of 1+1' to yield a mixture of compounds 24 and 24'.

[MH+]: 589.20

Example 24

Compounds 25 and 25'

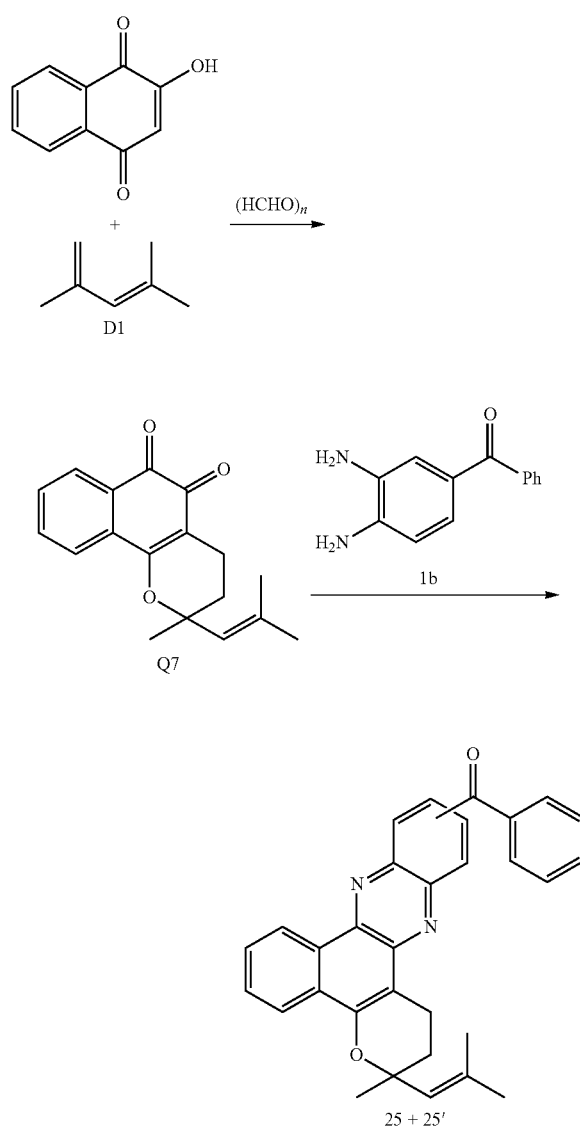

The quinone Q7 was prepared by condensation of hydroxy-naphthoquinone, paraformaldehyde and diene D1 according to an analogous procedure described in *Biorg. Med. Chem.*, 2008, 16, 1328-1336. Condensation with diamine 1b was carried out with a similar procedure used for the preparation of 1+1' to yield a mixture of compounds 25 and 25'.

[MH+]: 459.06

Example 25

Compounds 27 and 27'

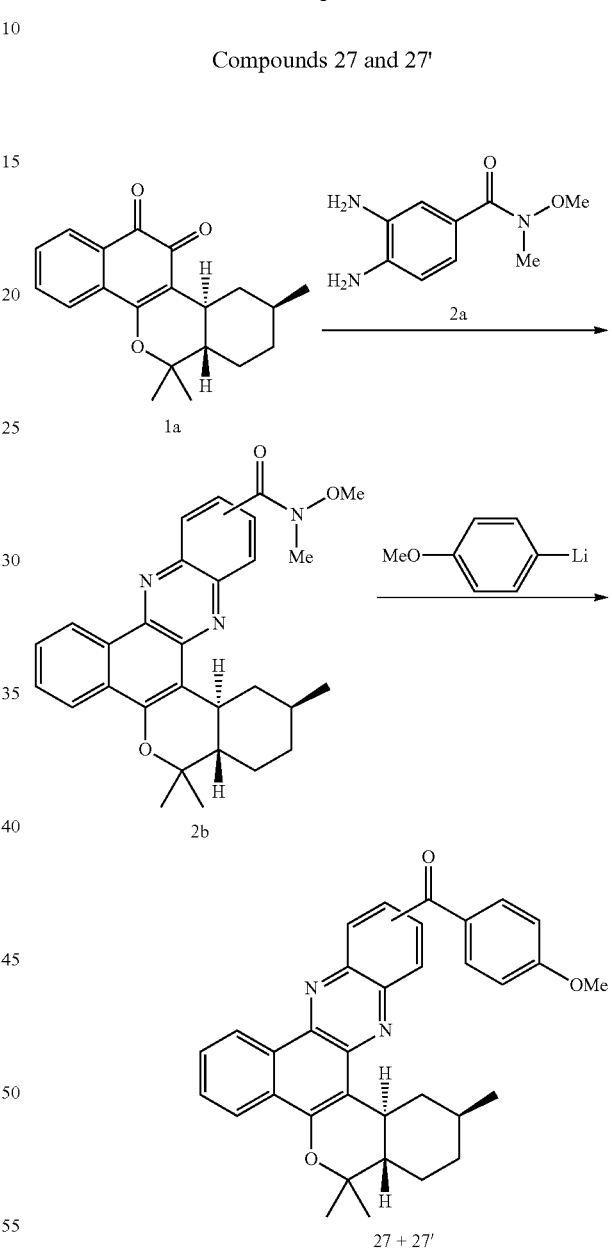

The general procedure used for the preparation of 2+2' was used for the preparation of 27+27' starting from Weinreb's amide 2b and p-methoxy phenyl lithium (prepared by transmetallation of the corresponding bromide with n-butyl lithium in THF).

[MH+]: 517.27

Example 26

Compounds 29 and 29'

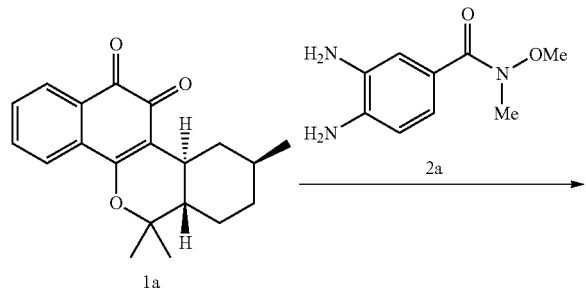

Example 27

Compounds 30 and 30'

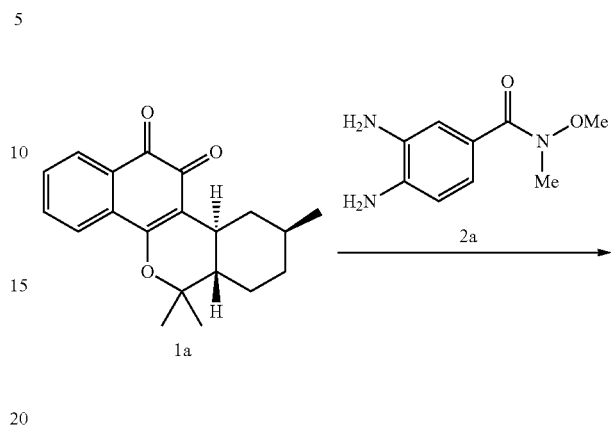

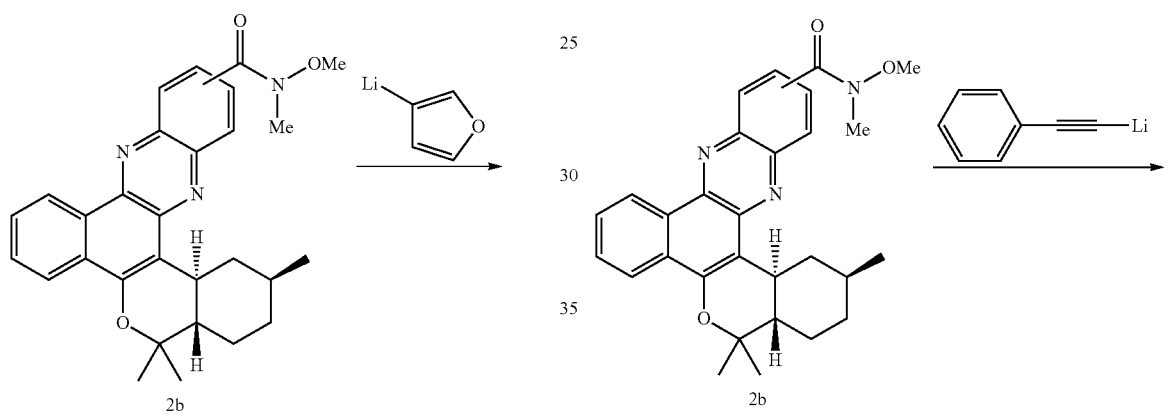

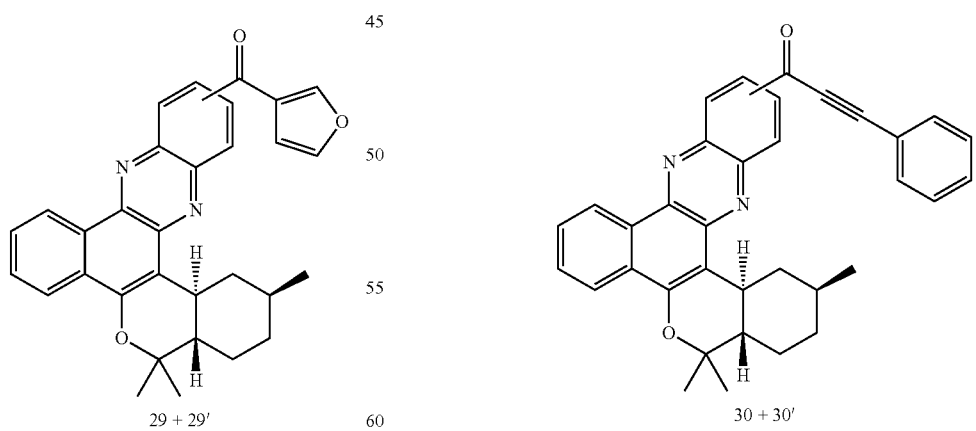

The general procedure used for the preparation of 2+2' was used for the preparation of 29+29' starting from Weinreb's amide 2b and 3-furyl lithium (prepared by transmetallation of the corresponding bromide with n-butyl lithium in THF).

[MH$^+$]: 477.37

The general procedure used for the preparation of 2+2' was used for the preparation of 30+30' starting from Weinreib's amide 2b and lithium phenyl acetylide (prepared by reaction of phenyl acetylene and n-butyl lithium in THF).

[MH$^+$]: 511.19

Example 28

Compounds 32 and 32'

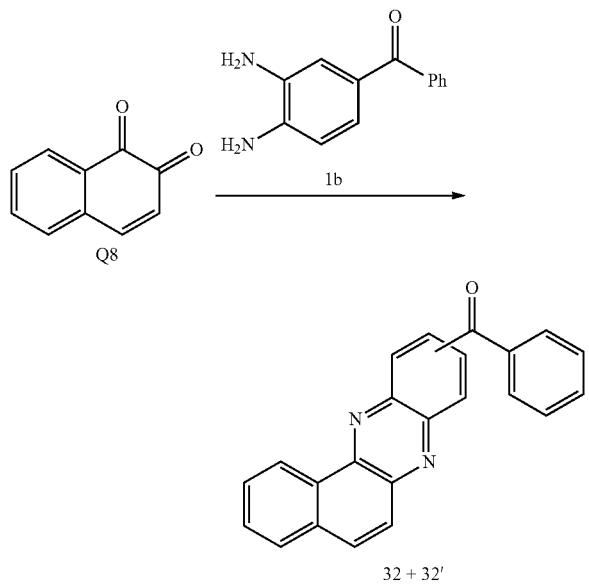

Condensation of commercially available 1,2-naphthquinone Q8 (TCI Europe) with diamine 1b was carried out with a similar procedure used for the preparation of 1+1' to yield a mixture of compounds 32 and 32'.

[MH+]: 335.31

Example 29

Compounds 33 and 33'

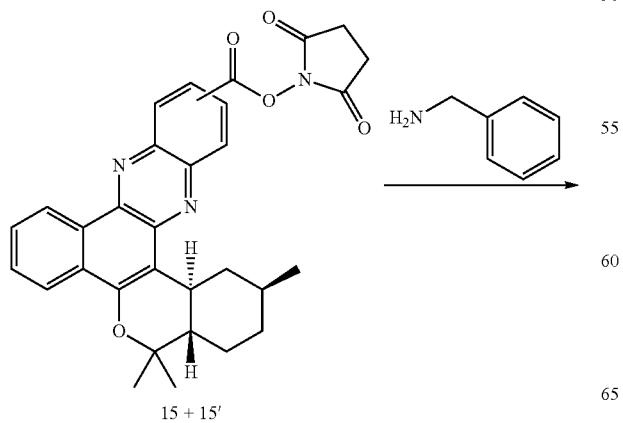

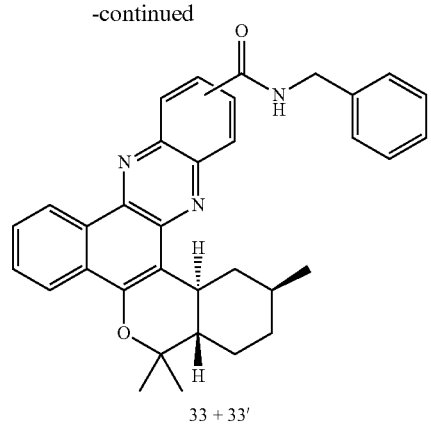

The mixture of regioisomers 33 and 33' was prepared according to the general procedure described for compounds 16 and 16' starting from the NHS esters 15 and 15' and benzylamine.

[MH+]: 516.2

Example 30

Compounds 34 and 34'

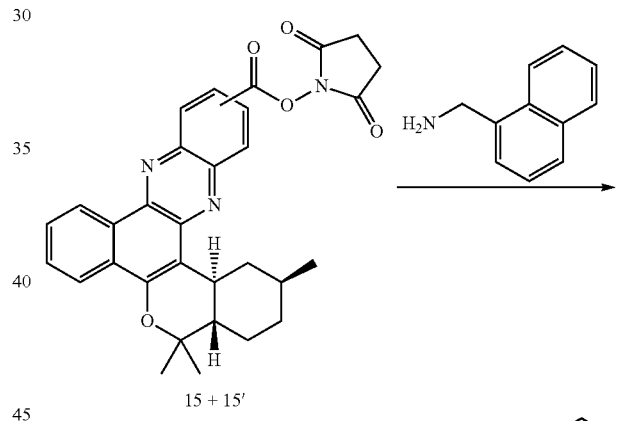

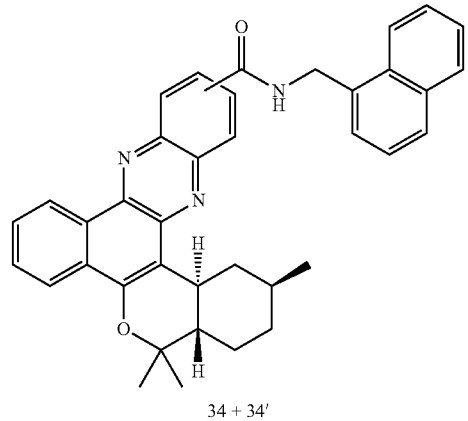

The mixture of regioisomers 34 and 34' was prepared according to the general procedure described for compounds 16 and 16 starting from the NHS esters 15 and 15' and 2-naphtylmethylamine.

[MH+]: 565.7

Example 31

Compounds 35 and 35'

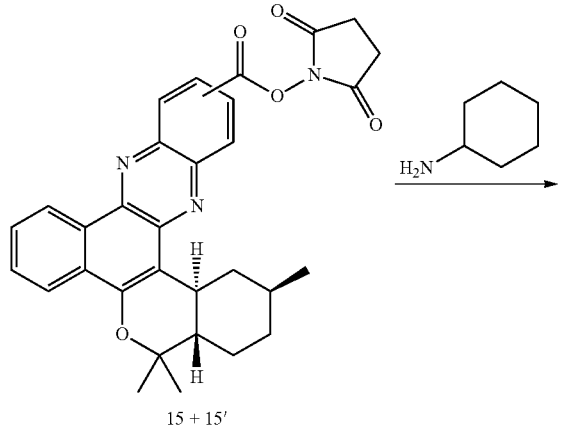

15 + 15'

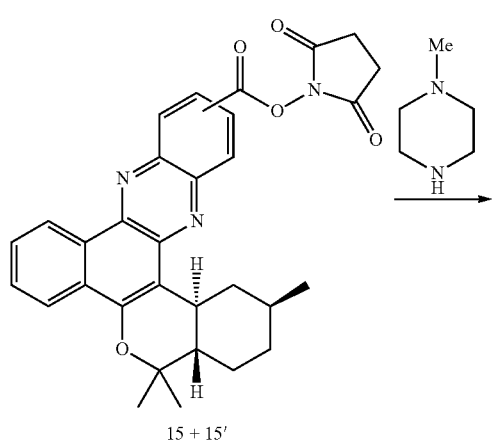

35 + 35'

The mixture of regioisomers 35 and 35' was prepared according to the general procedure described for compounds 16+16 starting from the NHS esters 15+15' and cyclohexylamine.

[MH$^+$]: 507.04

Example 32

Compounds 36 and 36'

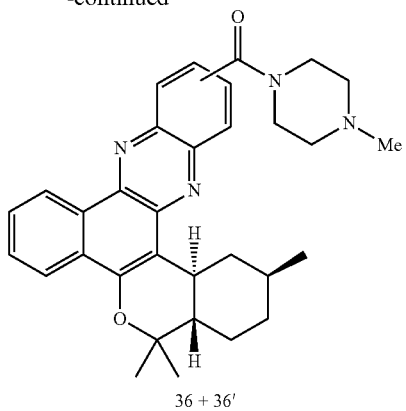

36 + 36'

The mixture of regioisomers 36+36' was prepared according to the general procedure described for compounds 16+16 starting from the NHS esters 15+15' and N-methylpiperazine.

[MH$^+$]: 509.34

Example 33

Compounds 37 and 37'

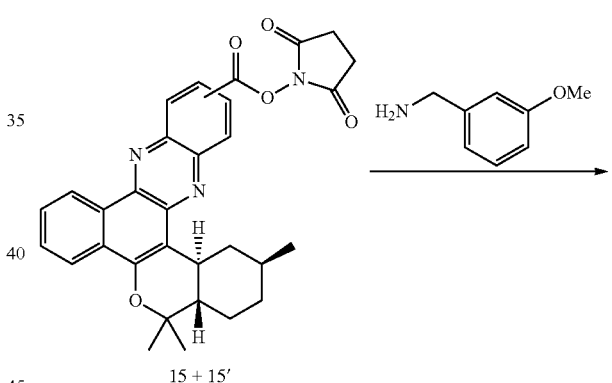

15 + 15'

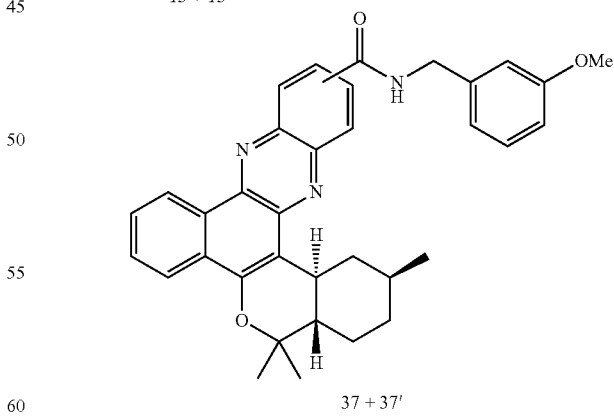

37 + 37'

The mixture of regioisomers 37 and 37' was prepared according to the general procedure described for compounds 16+16 starting from the NHS esters 15+15' and m-methoxybenzylamine.

[MH$^+$]: 546.25

Example 34

Compounds 38 and 38'

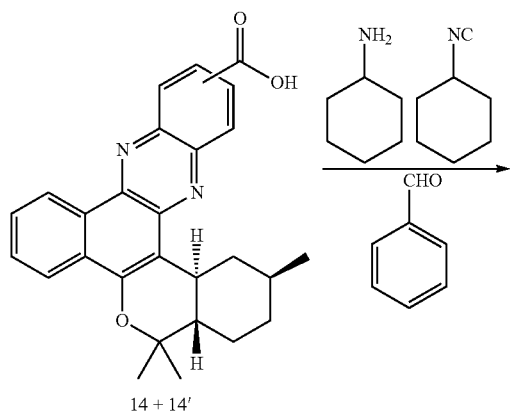

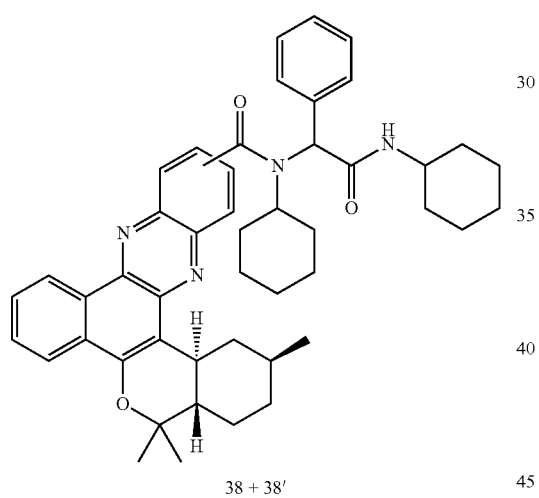

The mixture of regioisomers 38 and 38' was prepared via a 4 components Ugi reaction starting from acids 14+14'. Benzaldehyde and cyclohexylamine (1 mmol each) were stirred in 1 mL methanol for 30 min at room temperature. Cyclohexylisocyanide (1 mmol) and acids 14+14' (1 mmol) were added and the resulting solution was stirred at room temperature for 18 h. After concentration, the crude reaction mixture was purified by flash chromatography on silica gel (PE/EtOAc: 8/2) to deliver the mixture of amides 38 and 38' as a yellow oil.

[MH$^+$]: 723.26

Example 35

Compounds 39 and 39'

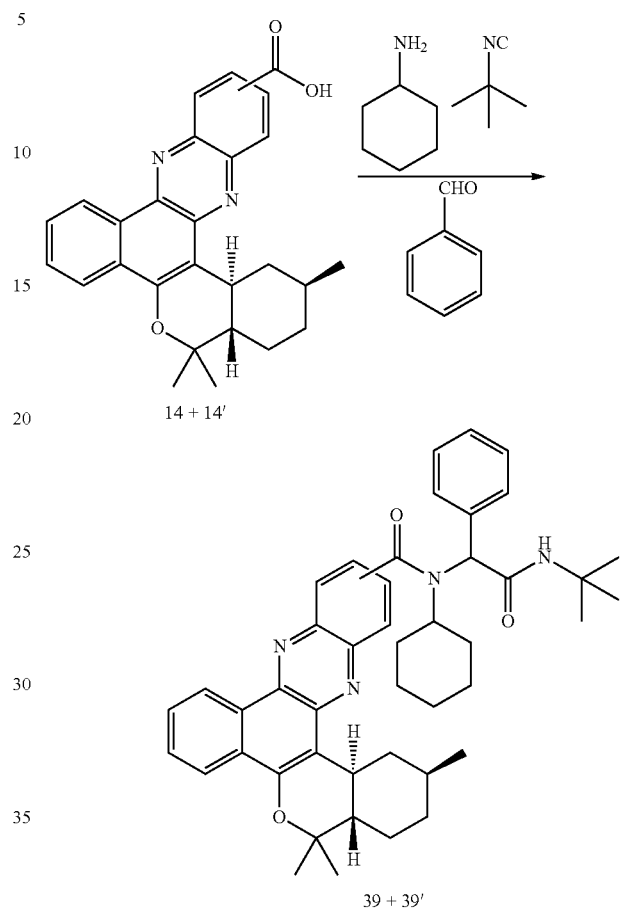

The procedure used for the preparation of 38 and 38' was used starting from the mixture of acids 14+14', cyclohexylamine, benzaldehyde and tert-butyl isocyanide to yield a mixture of compounds 39 and 39'.

[MH$^+$]: 697.34

Example 35

Compounds 40 and 40'

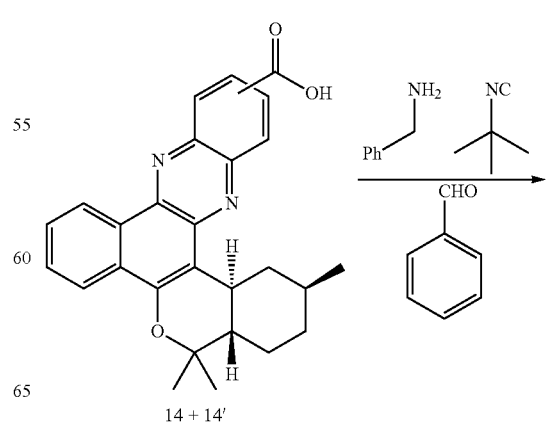

-continued

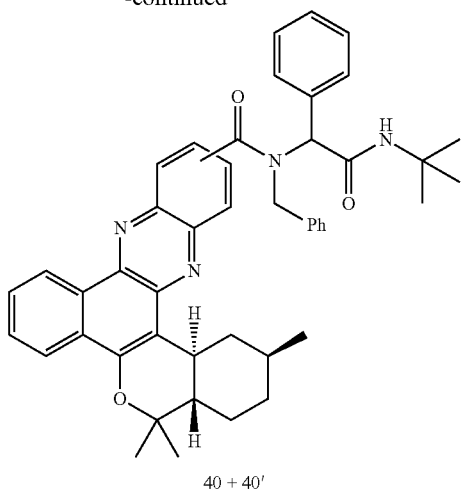

40 + 40'

The procedure used for the preparation of 38 and 38' was used starting from the mixture of acids 14+14', benzylamine, benzaldehyde and tert-butyl isocyanide to yield a mixture of compounds 40 and 40'.
[MH+]: 705.12

Example 36

Compounds 41 and 41'

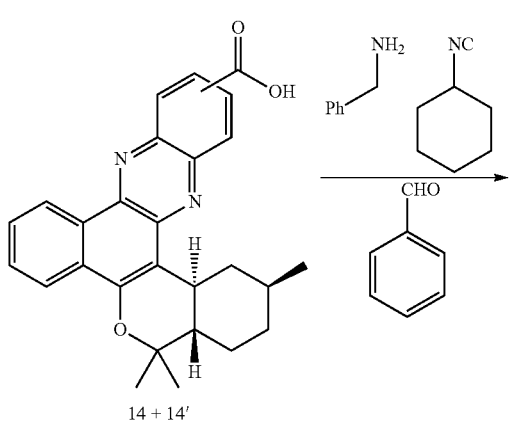

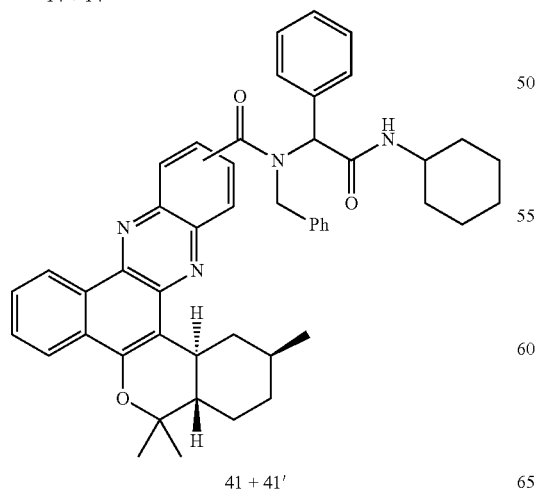

41 + 41'

The procedure used for the preparation of 38 and 38' was used starting from the mixture of acids 14+14', benzylamine, benzaldehyde and cyclohexyl isocyanide to yield a mixture of compounds 41 and 41'.
[MH+]: 731.22

Example 37

Compounds 42 and 42'

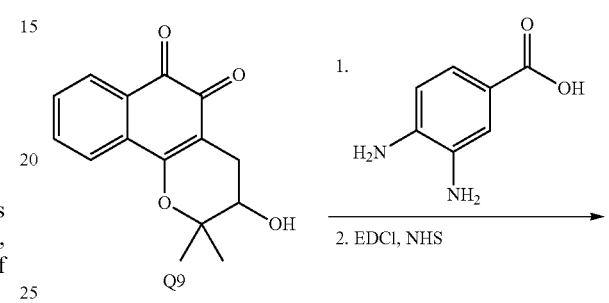

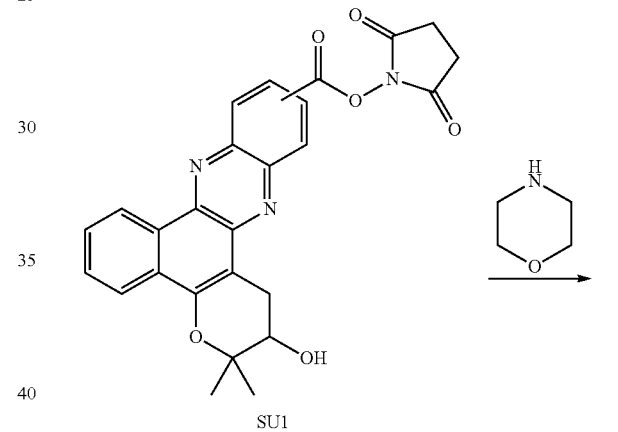

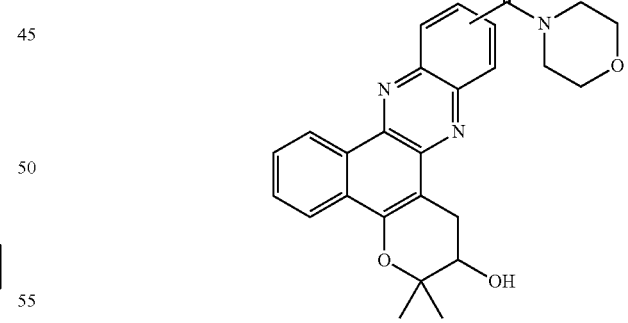

42+42'

The procedure used for the preparation of 42+42' was to start from hydroxylapachone Q9 (prepared according to: *Tetrahedron Letters* 39 (1998) 8221-8224) and follow a similar procedure to the one used for the preparation of 17+17'.
[MH+]: 444.16

Example 38

Compounds 43 and 43'

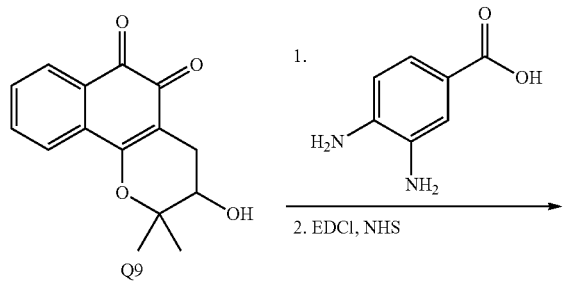

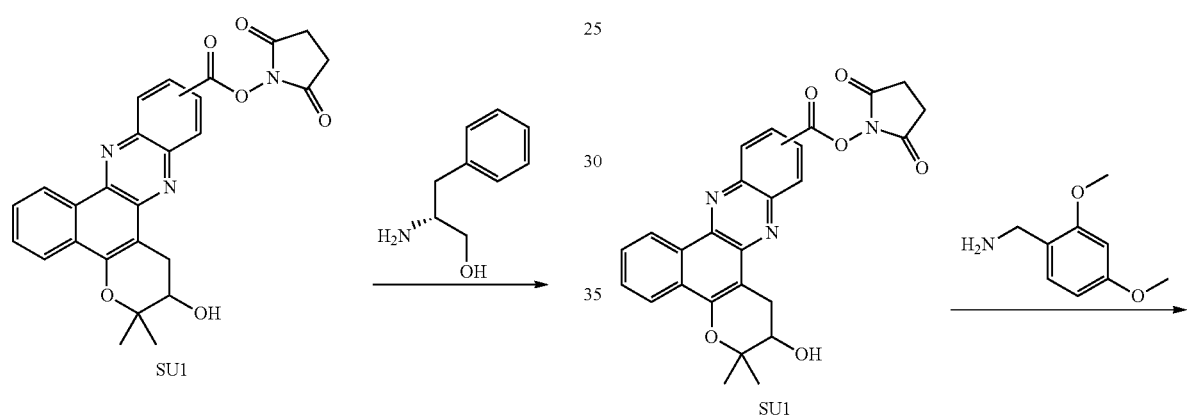

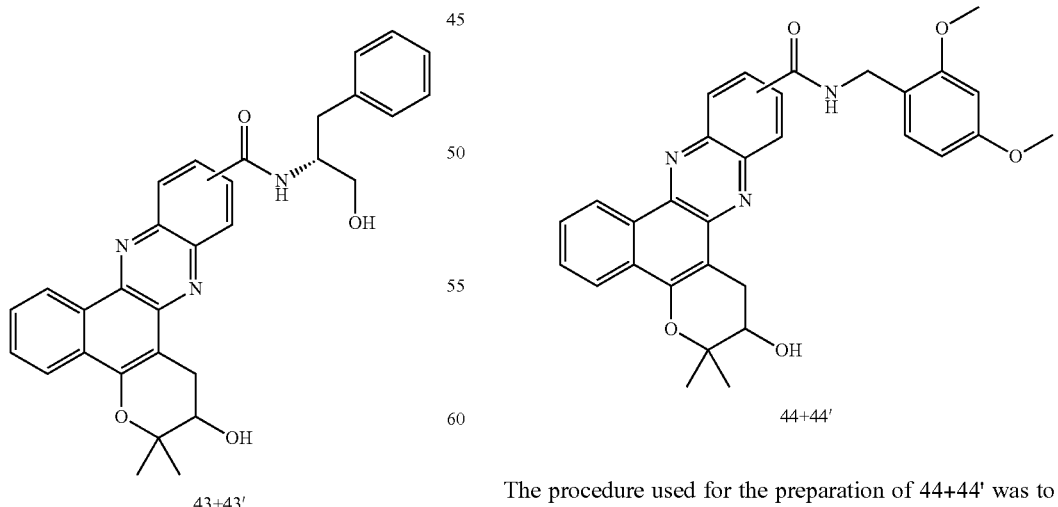

43+43'

The procedure used for the preparation of 43+43' was to start from hydroxylapachone Q9 (prepared according to: *Tetrahedron Letters* 39 (1998) 8221-8224) and follow a similar procedure to the one used for the preparation of 17+17'.

[MH$^+$]: 508.2

Example 39

Compounds 44 and 44'

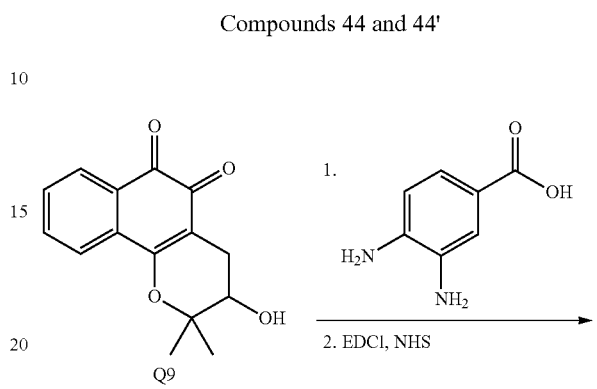

44+44'

The procedure used for the preparation of 44+44' was to start from hydroxylapachone Q9 (prepared according to: *Tetrahedron Letters* 39 (1998) 8221-8224) and to follow a similar procedure to the one used for the preparation of 17+17'.

[MH$^+$]: 523.6

Example 40

Compounds 45 and 45'

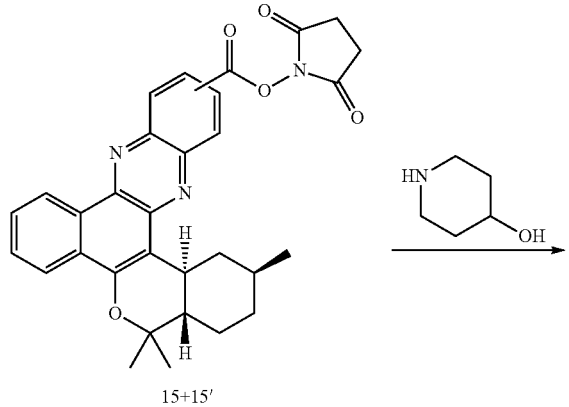

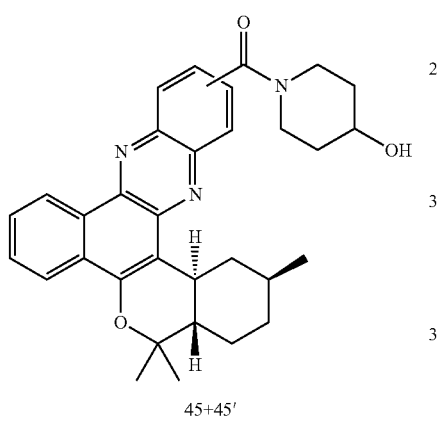

The procedure used for the preparation of 45+45' was done starting from NHS derivative 15+15' and following a similar procedure to the one used for the preparation of 17+17'.

[MH$^+$]: 510.42

Example 41

Compounds 46 and 46'

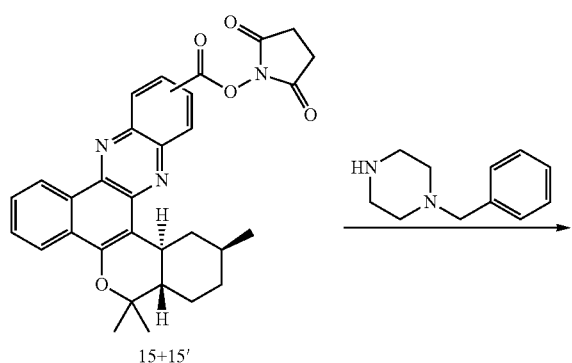

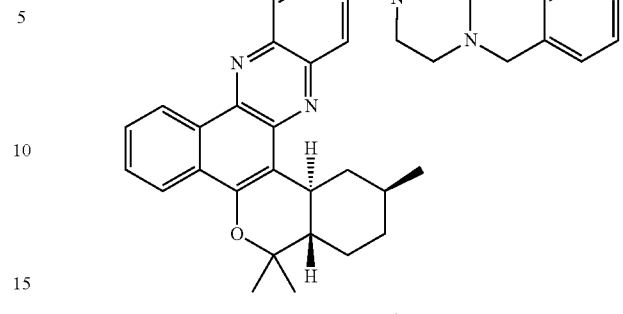

The procedure used for the preparation of 46+46' was done starting from NHS derivative 15+15' and following a similar procedure to the one used for the preparation of 17+17'.

[MH$^+$]: 584.32

Example 42

Compounds 47 and 47'

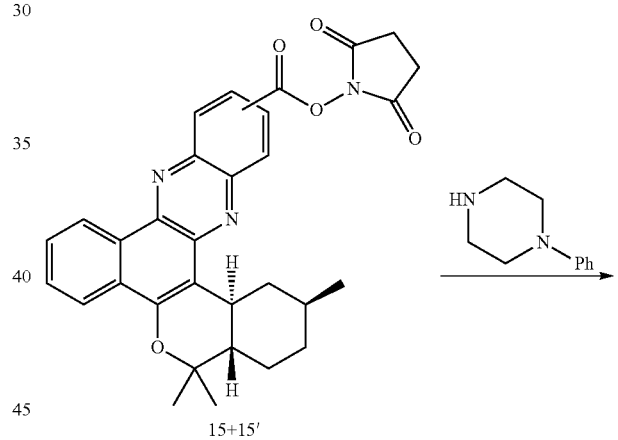

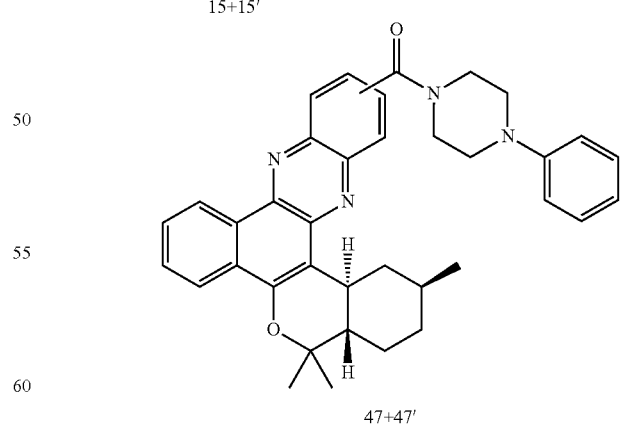

The procedure used for the preparation of 47+47' was done starting from NHS derivative 15+15' and following a similar procedure to the one used for the preparation of 17+17'.

[MH$^+$]: 571.37

Example 42

Compounds 48 and 48'

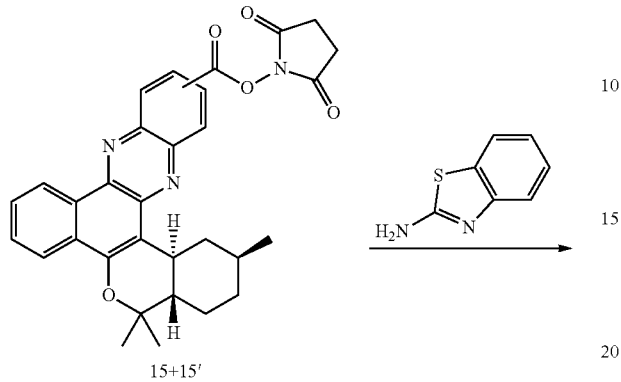

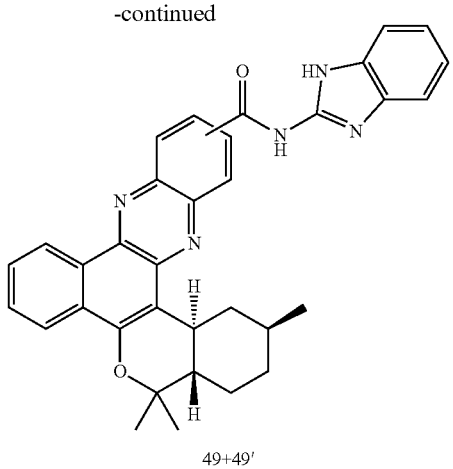

The procedure used for the preparation of 48+48' was done starting from NHS derivative 15+15' and following a similar procedure to the one used for the preparation of 17+17'.

[MH$^+$]: 559.15

Example 43

Compounds 49 and 49'

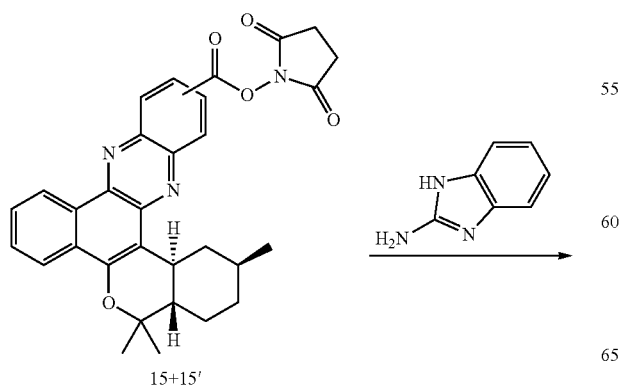

The procedure used for the preparation of 49+49' was done starting from NHS derivative 15+15' and following a similar procedure used for the preparation of 17+17'.

[MH$^+$]: 541.64

Example 44

Compounds 50 and 50'

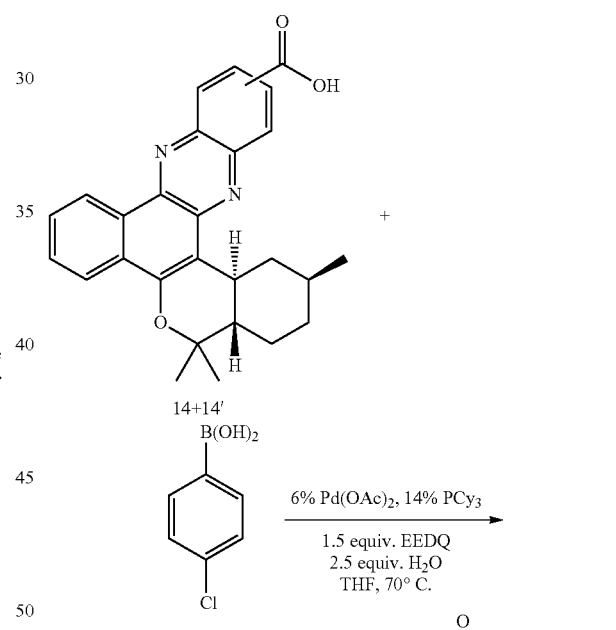

The mixture of acids 14 and 14' (70 mg, 0.16 mmol), palladium acetate (2.3 mg, 0.0096 mmol, 0.06 equi.) and tricyclohexylphosphine (6 mg, 0.023 mmol, 0.14 equiv.) were suspended in 5 mL of freshly distilled THF under argon. Water (7 mL, 0.4 mmol, 2.5 equiv., 2.5 equiv.) and EEDQ (61 mg, 0.25 mmol, 1.5 equiv.) are added after 5 min of stirring at room temperature. After a further 5 min of stirring, p-chlorophenyl boronic acid (Aldrich) (0.25 mmol, 1.5 equiv) is added in one portion under a flux of argon and the reaction mixture is refluxed overnight. After standard work up, the pure ketones 50 and 50' are isolated by flash chromatography on silica gel (PE/EtOAc: 70/30) in a quantitative yield.

[M$^+$]: 521.14

Example 45

Compounds 51 and 51'

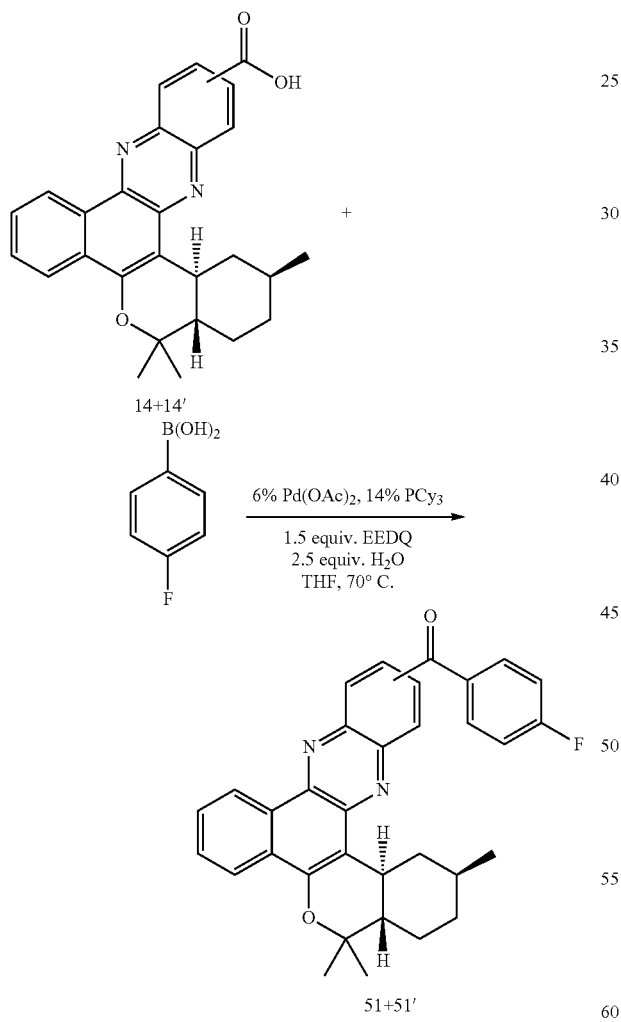

Example 46

Compounds 52 and 52'

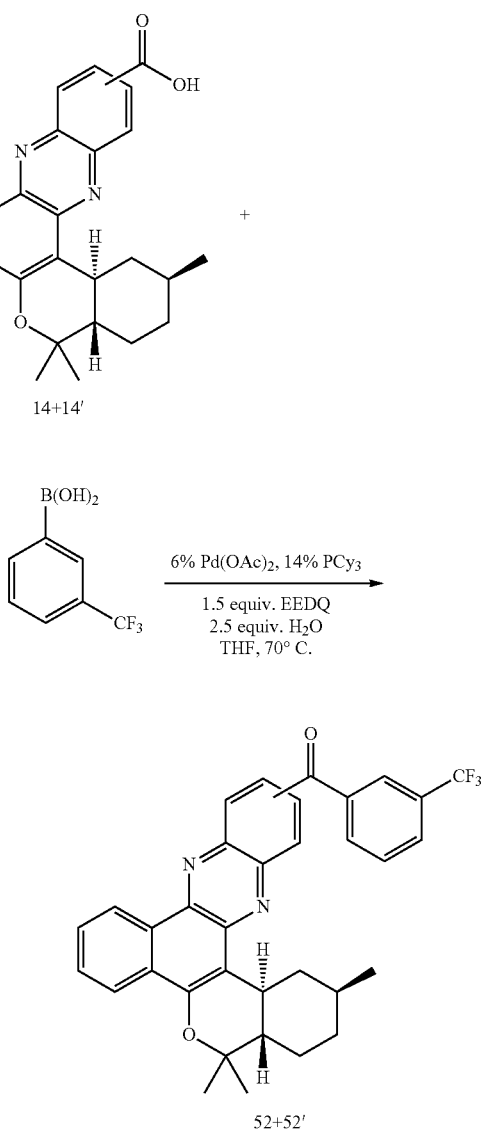

The procedure used for the preparation of 51+51' was done starting from acids 14+14' and p-fluorophenylboronic acid ((Aldrich) and following a similar procedure used for the preparation of 50+50'.

[MH$^+$]: 505.17

The procedure used for the preparation of 52+52' was done starting from acids 14+14' and m-trifluoromethylphenyl boronic acid (Aldrich) and following a similar procedure used for the preparation of 50+50'.

[MH$^+$]: 555.13

Example 47
Compounds 53 and 53'

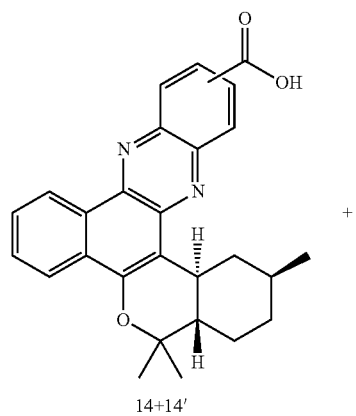

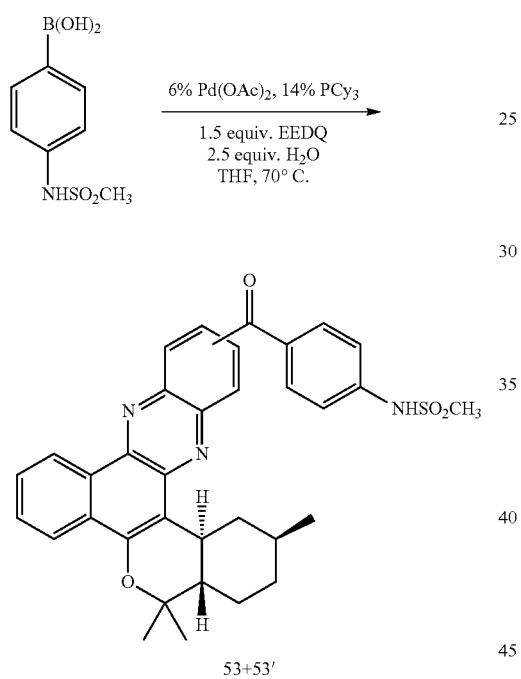

Example 48
Compounds 54 and 54'

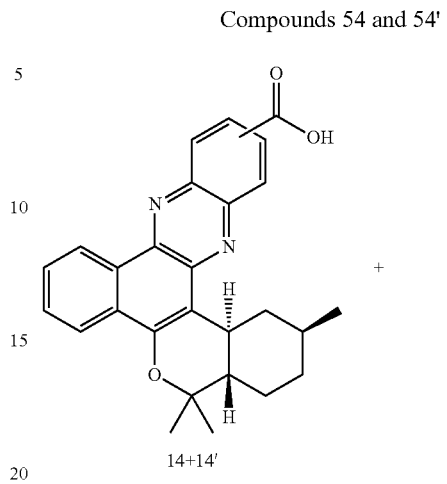

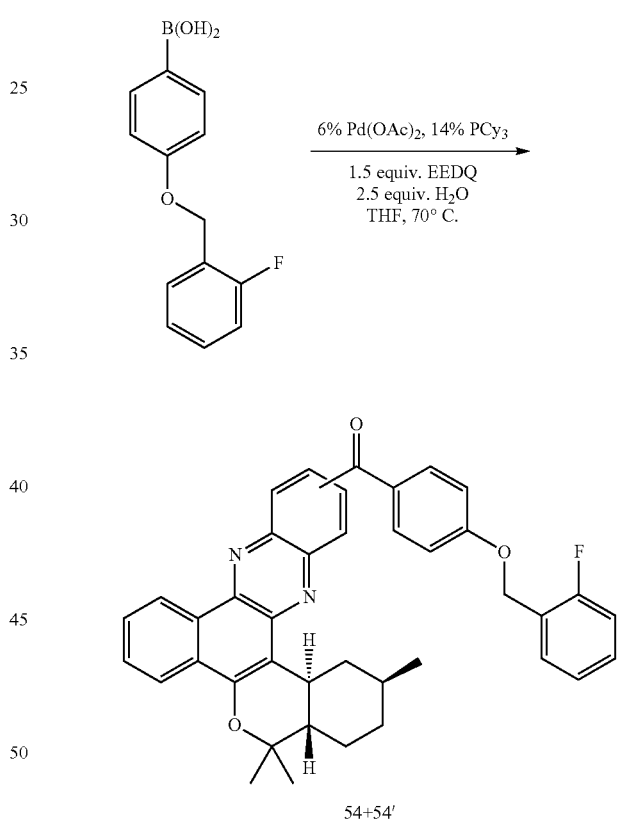

The procedure used for the preparation of 53+53' was done starting from acids 14+14' and p-methanesulfonamidophenylboronic acid (Aldrich) and following a similar procedure used for the preparation of 50+50'.

[MH$^+$]: 580.30

The synthesis was also carried out starting from the pure enantiomers of citronelal (TCI). The mixture of ketones arising from (R)-(+)-citronelal are labelled (R)-(53+53') and the mixture of ketones arising from (S)-(−)-citronelal are labelled (S)-(53+53').

The procedure used for the preparation of 54+54' was done starting from acids 14+14' and p-(o-fluorobenzyloxy)-phenyl boronic acid (Aldrich) and following a similar procedure used for the preparation of 50+50'.

[MH$^+$]: 611.20

Example 49

Compounds 55 and 55'

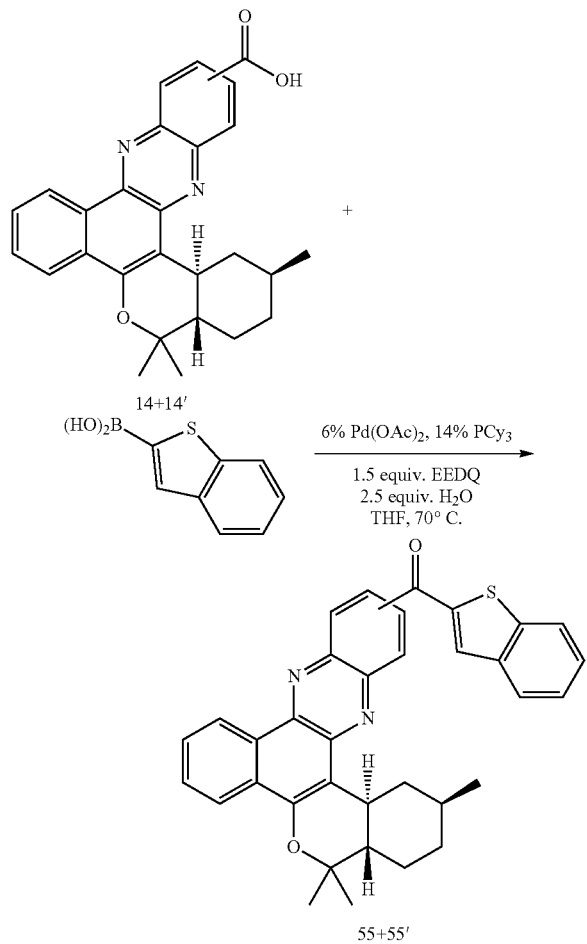

The procedure used for the preparation of 54+54' was done starting from acids 14+14' and 2-benzothiophene boronic acid (Aldrich) and following a similar procedure used for the preparation of 50+50'.

[MH⁺]: 543.29

Example 50

Compounds 56 and 56'

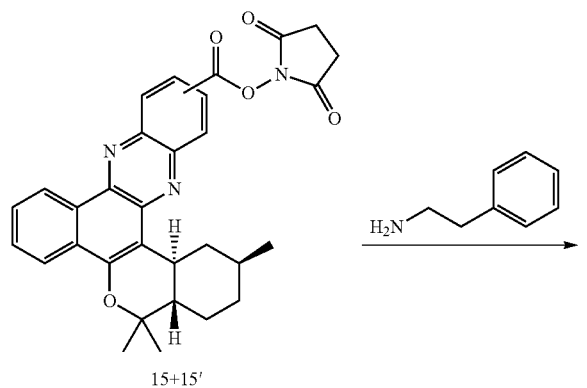

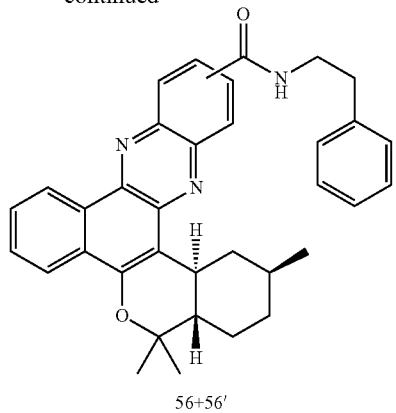

The procedure used for the preparation of 56+56' was done starting from NHS derivative 15+15' and following a similar procedure to the one used for the preparation of 17+17'.

[MH⁺]: 530.41

The synthesis was also carried out starting from the pure enantiomers of citronelal (TCI). The mixture of ester arising from (R)-(+)-citronelal will be labelled (R)-(56+56') and the mixture of ester arising from (S)-(−)-citronelal will be labelled (S)-(56+56').

BIOLOGY EXAMPLES

In Vitro Characterization of the Biological Effects of the Compounds According to the Invention MTT tests were performed in order to rapidly, i.e. within 3 days, measure the effect of compounds of this invention on the overall cell growth. The test measured the number of metabolically active living cells that were able to transform the yellow product 3-(4,5-dimethylthiazol-2-yl)-2,5-diphenyl tetrazolium bromide (herein referred as MTT) into the blue product formazan dye by mitochondrial reduction. The amount of formazan obtained at the end of the experiment, measured by means of a spectrophotometer (Plate Reader Victor X4 Microplate reader (Perkin Elmer), is directly proportional to the number of living cells. Optical density determination thus enabled a quantitative measurement of the effect of the investigated compounds under control conditions (normoxia) as compared to the hypoxic conditions (0.1 or 1% $O_2$) and/or untreated conditions.

Human umbilical vein endothelial cells (HUVEC) and six human cancer cell lines were used in the MTT tests. These cancer cell lines cover five histological cancer types including cervix (SiHa), breast (MCF-7 and MDA-MB231), prostate (PC3), glioma (U373), and colorectal (LoVo) cancers.

To perform the assay, cells were allowed to grow in 96-well microplates with a flat bottom following addition of an amount of 100 µl of cell suspension per well with 4,500 cells/well. Each cell line was seeded in its appropriate culture medium. HUVEC were cultured in a specific endothelial cell growth medium (ECACC, Sigma); SiHa cells in Glutamax-containing DMEM with 4.5 g/l glucose (Invitrogen) supplemented with 10% Foetal Bovine Serum (PAA) and 1% penicillin+streptomycin mix (Invitrogen); MCF-7, MDA-MB-231, PC3, and LoVo cells in Glutamax-containing RPMI supplemented with 10% Foetal Bovine Serum (PAA) and 1% penicillin+streptomycin mix (Invitrogen) and U373 cells in Glutamax-containing DMEM (Invitrogen) with 5% Foetal Bovine Serum (PAA) and 1% penicillin+streptomycin mix (Invitrogen).

The detailed experimental procedure was the following: after a 24-hour period of incubation at 37° C., the culture medium was replaced by 100 µl of fresh medium in which the tested compound was previously dissolved, at the following concentrations: $10^{-8}$ M, $5.10^{-8}$, $10^{-7}$, $5.10^{-7}$, $10^{-6}$, $5.10^{-6}$, $10^{-5}$, $5.10^{-5}$ and $10^{-4}$ µg/ml. Each experiment was performed in sestuplicates (6 times).

Cells were then incubated under normoxia in a Binder incubator (the $O_2$ level corresponding to the concentration in the ambient air), or in a Ruskin hypoxia workstation under either 0.1% $O_2$ (v/v) or 1% $O_2$ (v/v). Under both conditions, the atmosphere was humidified and the $CO_2$ concentration was fixed at 5 vol. %.

After 72 hours of incubation at 37° C. under normoxic or hypoxic conditions, with or without the compound to be tested, the medium was replaced by 100 µl of HBSS (without phenol red) containing MTT at a concentration of 0.5 or 1 mg/ml. The micro-wells were subsequently incubated during 3 hours and a half at 37° C. and centrifuged at 1300 rpm during 10 minutes. Medium was removed and formazan crystals formed were dissolved in 100 µl DMSO. The micro-wells were shaken for 5 minutes and read on a spectrophotometer at wavelengths of 570 nm (maximal formazan absorbance).

For each experimental condition, the mean optical density was calculated, allowing the determination of the percentage of living cells in comparison to the control.

Table 2 shows the $IC_{50}$ (representing the range of concentration of the compound tested that resulted in a 50% inhibition of overall cell growth) for each compound in endothelial cells under normoxic or hypoxic conditions.

TABLE 2

| Compound n[a] | $IC_{50}$ (µM) Normoxia | $IC_{50}$ (µM) Hypoxia 1% | Selectivity[a] | $IC_{50}$ (µM) Normoxia | $IC_{50}$ (µM) Hypoxia 0.1% | Selectivity[a] |
|---|---|---|---|---|---|---|
| 1 + 1' | 95.97 | 9.86 | 10 | 67.82 | 1.64 | 40 |
| 3 + 3' | 83.88 | 0.55 | 151 | 75.88 | 1.23 | 61 |
| 5 + 5' | 0.87 | 0.12 | 8 | 0.74 | 0.09 | 8 |
| 7 + 7' | 9.81 | 0.16 | 61 | 6.39 | 0.91 | 7 |
| 11 | 149.14 | 10.90 | 14 | u.t.d. | 65.83 | >3.4[b] |
| 11' | 175.70 | 11.80 | 15 | 224.73 | 13.62 | 16.5 |
| 12 | 5.65 | 0.40 | 14 | 8.27 | 0.14 | 58 |
| 12' | 4.14 | 0.14 | 29 | 4.24 | 0.04 | 105 |
| (R)-(12 + 12') | 7.14 | 0.59 | 12 | — | — | — |
| (S)-(12 + 12') | 2.66 | 0.18 | 15 | — | — | — |
| 16 + 16' | 119.51 | 5.91 | 20 | 22.15 | 0.09 | 255 |
| (R)-(16 + 16') | 173.7 | 0.76 | 227 | — | — | — |
| (S)-(16 + 16') | 173.7 | 0.83 | 208 | — | — | — |
| 17 + 17' | 5.54 | 0.27 | 21 | 5.54 | 0.01 | 515 |
| 16 | 42.59 | 14.37 | 3 | 128.7 | 0.09 | 1480 |
| 16' | 119.68 | 7.96 | 15 | 16.68 | 0.21 | 80 |
| 17 | 5.18 | 0.63 | 8 | 6.25 | 0.05 | 134 |
| 17' | 5.72 | 0.36 | 16 | 16.97 | 0.07 | 230 |
| 18 + 18' | 82.25 | 10.03 | 8.6 | / | / | / |
| 19 + 19' | 49.09 | 4.23 | 11.06 | / | / | / |
| 20 + 20' | 44.8 | 3.15 | 14.25 | / | / | / |
| 22 + 22' | 52.86 | 0.62 | 85.7 | / | / | / |
| 23 + 23' | 38.2 | 58.19 | 0.66 | / | / | / |
| 24 + 24' | 38.3 | 1.02 | 37.5 | / | / | / |
| 25 + 25' | 62.42 | 6.54 | 10 | / | / | / |
| 27 + 27' | 114.2 | 7.36 | 15.5 | / | / | / |
| 29 + 29' | 57.7 | 3.5 | 18 | / | / | / |
| 30 + 30' | 127.29 | 84.21 | 1.5 | / | / | / |
| 32 + 32' | 12.26 | 4.79 | 2.5 | / | / | / |
| 33 + 33' | 129 | 0.72 | 181 | / | / | / |
| 34 + 34' | 4.07 | 4.68 | 0.9 | / | / | / |
| 35 + 35' | 86 | 8.8 | 9.8 | / | / | / |
| 36 + 36' | 5.11 | 0.59 | 8.7 | / | / | / |
| 37 + 37' | 33 | 0.73 | 45 | / | / | / |
| 38 + 38' | 53.25 | 6.22 | 9 | / | / | / |
| 39 + 39' | u.t.d. | 5.88 | >24 | / | / | / |
| 40 + 40' | 36.18 | 4.26 | 8.5 | / | / | / |
| 41 + 41' | 62.9 | 16.4 | 3.8 | / | / | / |
| 42 + 42' | 6.57 | 0.61 | 10.7 | / | / | / |
| 43 + 43' | 1.93 | 0.06 | 31.6 | / | / | / |
| 44 + 44' | 47.75 | 0.05 | 893 | / | / | / |
| 45 + 45' | 3.92 | 0.1 | 38.5 | / | / | / |
| 46 + 46' | 23.9 | 1.88 | 12.7 | / | / | / |
| 47 + 47' | 99.2 | 64.8 | 1.53 | / | / | / |
| 48 + 48' | 164.7 | 42.9 | 3.8 | / | / | / |
| 49 + 49' | 64.6 | 18.5 | 3.5 | / | / | / |
| 50 + 50' | N.A. | 4.61 | >41 | / | / | / |
| 51 + 51' | N.A. | 1.98 | >100 | / | / | / |
| 52 + 52' | N.A. | 28.85 | >6 | / | / | / |
| 53 + 53' | 6.73 | 0.03 | 260 | | | |
| (R)- | 5.95 | 0.11 | 54 | / | / | / |

TABLE 2-continued

| Compound n° | IC$_{50}$ (μM) Normoxia | IC$_{50}$ (μM) Hypoxia 1% | Selectivity[a] | IC$_{50}$ (μM) Normoxia | IC$_{50}$ (μM) Hypoxia 0.1% | Selectivity[a] |
|---|---|---|---|---|---|---|
| (53 + 53') | | | | | | |
| (S)-(53 + 53') | 7.59 | 0.07 | 107 | / | / | / |
| 54 + 54' | 81.22 | 37.17 | 2 | / | / | / |
| 55 + 55' | N.A. | 14.93 | >12 | / | / | / |
| 56 + 56' | 125.93 | 0.17 | 741 | | | |
| (R)-(56 + 56') | 188.8 | 0.51 | 370 | / | / | / |
| (S)-(56 + 56') | 188.8 | 0.57 | 333 | / | / | / |

[a]Selectivity = IC$_{50}$ (normoxia)/IC$_{50}$ (hypoxia)
[b]When IC$_{50}$ could not be determined in either normoxic or hypoxic conditions because of limited inhibitory activity (u.t.d. = unable to determine), the selectivity was determined as the ratio of the activity at 100 μM [ie, activity at 100 μM (normoxia)/activity at 100 μM (hypoxia)]

Table 3 shows the IC$_{50}$ (representing the range of concentration of the compound tested that resulted in a 50% inhibition of overall cell growth) for each compound in each tumor cell line investigated under normoxic or hypoxic conditions.

TABLE 3

| Compound | IC$_{50}$ (μM) Normoxia | IC$_{50}$ (μM) Hypoxia 1% O2 | Selectivity[a] | IC$_{50}$ (μM) Normoxia | IC$_{50}$ (μM) Hypoxia 1% O2 | Selectivity[a] | IC$_{50}$ (μM) Normoxia | IC$_{50}$ (μM) Hypoxia 1% O2 | Selectivity[a] |
|---|---|---|---|---|---|---|---|---|---|
| | MDA-MB-231 | | | MCF-7 | | | PC3 | | |
| 1 + 1' | 147.97 | 190.09 | 0.78 | 17.47 | u.t.d. | <0.09[b] | u.t.d. | u.t.d. | / |
| 3 + 3' | 45.12 | 54.35 | 0.83 | 117.93 | 109.72 | 1.07 | 157.92 | 15.59 | 10.13 |
| 5 + 5' | 1.50 | 1.04 | 1.44 | 1.93 | 0.46 | 4.20 | 8.29 | 1.70 | 4.86 |
| 7 + 7' | 13.23 | 6.84 | 1.93 | 13.91 | 1.55 | 8.97 | 19.38 | 9.12 | 2.13 |
| 11 | u.t.d. | 157.76 | >1.44[b] | u.t.d. | u.t.d. | / | u.t.d. | u.t.d. | / |
| 11' | u.t.d. | 136.20 | >1.67[b] | u.t.d. | 149.82 | >1.52[b] | u.t.d. | 161.17 | >1.41[b] |
| 12 | 30.27 | 1.27 | 23.81 | 8.07 | 1.45 | 5.56 | 14.73 | 1.31 | 11.23 |
| 12' | 44.39 | 1.31 | 33.85 | 11.30 | 1.45 | 7.78 | 15.33 | 1.41 | 10.86 |
| 16 + 16' | u.t.d. | 137.22 | >1.27[b] | 137.22 | 67.74 | 2.03 | u.t.d. | u.t.d. | / |
| 17 + 17' | 17.69 | 9.83 | 1.80 | 12.15 | 6.43 | 1.89 | 13.40 | 10.54 | 1.27 |
| 16 | u.t.d. | 230.24 | >1.16[b] | u.t.d. | 163.69 | >1.63[b] | u.t.d. | u.t.d. | / |
| 16' | u.t.d. | 125.93 | >1.38[b] | u.t.d. | 91.19 | >1.91[b] | u.t.d. | u.t.d. | / |
| 17 | 13.40 | 11.43 | 1.17 | 12.15 | 11.08 | 1.10 | 10.36 | 11.08 | 0.94 |
| 17' | 59.85 | 11.08 | 5.40 | 17.15 | 12.51 | 1.37 | 15.19 | 11.61 | 1.31 |
| 50 + 50' | u.t.d. | u.t.d. | / | u.t.d. | u.t.d. | / | / | / | / |
| 51 + 51' | u.t.d. | u.t.d. | / | u.t.d. | 75.51 | 1.32 | / | / | / |
| 52 + 52' | u.t.d. | u.t.d. | / | u.t.d. | u.t.d. | / | / | / | / |
| 53 + 53' | 15.18 | 1.45 | 10.47 | 44.51 | 1.16 | 38.37 | / | / | / |
| 54 + 54' | u.t.d. | u.t.d. | / | u.t.d. | u.t.d. | / | / | / | / |
| 55 + 55' | u.t.d. | u.t.d. | / | u.t.d. | u.t.d. | / | / | / | / |
| 56 + 56' | 38.33 | 10.57 | 3.63 | 56.64 | 6.42 | 8.82 | / | / | / |
| | LoVo | | | siHa | | | U373 | | |
| 1 + 1' | 129.47 | 160.30 | 0.81 | 177.76 | 79.12 | 2.25 | 117.14 | 76.04 | 1.54 |
| 3 + 3' | 90.24 | 17.43 | 5.18 | u.t.d. | 8.61 | >23.81[b] | 180.48 | 6.15 | 29.33 |
| 5 + 5' | 1.38 | 1.24 | 1.11 | 10.36 | 1.20 | 8.65 | 1.24 | 0.15 | 8.31 |
| 7 + 7' | 16.19 | 11.40 | 1.42 | 22.12 | 10.95 | 2.02 | 7.98 | 1.37 | 5.83 |
| 11 | 215.65 | 152.09 | 1.42 | u.t.d. | 133.93 | >1.69[b] | u.t.d. | 140.74 | >1.61[b] |
| 11' | 220.19 | 154.36 | 1.43 | u.t.d. | 131.66 | >1.72[b] | u.t.d. | 74.91 | >3.03[b] |
| 12 | 9.69 | 1.31 | 7.38 | 19.77 | 1.13 | 17.50 | 10.59 | 0.14 | 75.00 |
| 12' | 10.59 | 1.21 | 8.75 | 72.64 | 1.17 | 62.07 | 9.08 | 0.61 | 15.00 |
| 16 + 16' | 139.83 | 124.20 | 1.13 | u.t.d. | u.t.d. | / | u.t.d. | 94.67 | >1.83[b] |
| 17 + 17' | 13.94 | 8.04 | 1.73 | 105.41 | 11.26 | 9.37 | 9.38 | 4.11 | 2.28 |
| 16 | 210.27 | u.t.d. | <0.79[b] | u.t.d. | 138.41 | >1.92[b] | u.t.d. | 233.70 | >1.14[b] |
| 16' | 116.38 | 153.73 | 0.76 | u.t.d. | 92.06 | >1.89[b] | u.t.d. | 112.91 | >1.54[b] |
| 17 | 9.83 | 9.47 | 1.04 | 75.04 | 10.54 | 7.12 | 6.97 | 1.23 | 5.65 |
| 17' | 18.76 | 11.43 | 1.64 | 101.84 | 10.72 | 9.50 | 11.61 | 1.34 | 8.67 |

In Vivo Validation of the Biological Effects of Representative Compounds According to the Invention 8-week-old NMRi nu/nu nude mice were subcutaneously injected with 3 millions human colorectal Widr cells in physiological saline solution (NaCl 9 g/L). Three weeks later, DMSO-solubilised compounds 12' and 17+17' (6.25 mg/kg) were intra-peritoneally injected every day for 7 days (5 mice per group). Before each injection, tumour volume was measured using an electronic calliper.

The effects of compounds 12' and 17+17' on human colorectal WiDr tumor growth (vs vehicle=DMSO) are represented in FIG. 1. Data are expressed as % of the tumor volume determined at time 0 and correspond to the mean values (per group of mice) determined at days 1, 2, 4 and 7.

The invention claimed is:
1. A compound of formula (Ia):

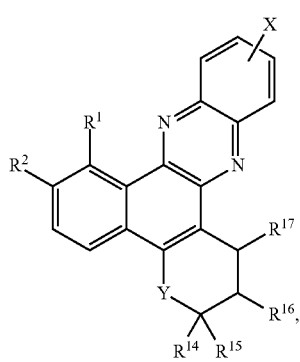

(Ia)

and pharmaceutically acceptable salts thereof, wherein
$R^1$ and $R^2$ are each, independently, H, halogen, hydroxy, C1-C6 alkyl, C2-C6 alkenyl, C1-C6 alkoxy, C1-C6 alkoxycarbonyl, amino, alkylamino, dialkylamino, aryl, arylalkyl, heteroaryl, heterocyclyl, nitro, cyano, carboxy, or amido;
$R^3$ and $R^4$ are each, independently, H, halogen, hydroxy, C1-C6 alkyl, C2-C6 alkenyl, C1-C6 alkoxy, C1-C6 alkoxycarbonyl, amino, alkylamino, aryl, arylalkyl, heteroaryl, heterocyclyl, nitro, cyano, carboxy, or amido;
X is selected from the group consisting of —COOR$^5$, —CONHR$^6$, —CONR$^6$R$^7$, —C(O)R$^8$, and —C(=NOH)R$^9$;
$R^5$ is C1-C6 alkyl, C2-C6 alkenyl, C2-C6 alkynyl, cycloalkyl, heterocyclyl, aryl, aralkyl or heteroaryl, wherein each of said cycloalkyl, heterocyclyl, aryl, aralkyl or heteroaryl groups is optionally substituted with one or more group(s) selected from the group consisting of C1-C4 alkyl, C1-C4 alkoxy and halogen;
$R^6$ is C1-C6 alkyl, C2-C6 alkenyl, C2-C6 alkynyl, cycloalkyl, heterocyclyl, aryl, aralkyl or heteroaryl, wherein each of said cycloalkyl, heterocyclyl, aryl, aralkyl or heteroaryl groups is optionally substituted with one or more group(s) selected from the group consisting of C1-C4 alkyl, C1-C4 alkoxy, halogen and hydroxy(C1-C4 alkyl);
$R^7$ is C1-C6 alkyl, C2-C6 alkenyl, C2-C6 alkynyl, cycloalkyl, heterocyclyl, aryl, aralkyl or heteroaryl, wherein each of said cycloalkyl, heterocyclyl, aryl, aralkyl or heteroaryl groups is optionally substituted with one or more group(s) selected from the group consisting of C1-C4 alkyl, C1-C4 alkoxy, hydroxy, halogen and aryl; or $R^7$ is C1-C6 alkoxy; or $R^7$ is —CHR$^{10}$R$^{11}$, wherein $R^{10}$ is aryl or heteroaryl and $R^{11}$ is —C(O)NHR$^{12}$, wherein $R^{12}$ is C1-C6 alkyl or cycloalkyl; or $R^7$ and $R^6$ are taken together to form together with the nitrogen atom they are attached to a 5- or 6-membered cycloalkyl or a 5- or 6-membered heterocyclyl ring, the latter cycloalkyl or heterocyclyl rings being optionally substituted with one or more group(s) selected from the group consisting of C1-C4 alkyl, hydroxy, aryl and aralkyl;
$R^8$ is C1-C6 alkyl, C2-C6 alkenyl, cycloalkyl, heterocyclyl, aryl, arylalkynyl or heteroaryl, wherein each of said cycloalkyl, heterocyclyl, aryl, arylalkynyl or heteroaryl groups is optionally substituted with one or more group(s) selected from the group consisting of halogen, C1-C6 haloalkyl, C1-C6 alkoxy, aryl-C1-C2 alkoxy optionally substituted by one or more group(s) selected from halogen, and C1-C4 alkylsulfonylamino;
$R^9$ is C1-C6 alkyl, C2-C6 alkenyl, cycloalkyl, heterocyclyl, aryl, arylalkynyl or heteroaryl, wherein each of the cycloalkyl, heterocyclyl, aryl, arylalkynyl or heteroaryl groups is optionally substituted with one or more group(s) selected from the group consisting of C1-C6 haloalkyl and C1-C6 alkoxy;
$R^{14}$ and $R^{15}$ are independently selected from H, C1-C4 alkyl, C2-C6 alkenyl, hydroxy, halo, alkoxy, amino, alkylamino, nitro, cyano, carboxy, or amido; and
$R^{16}$ and $R^{17}$ are independently selected from H, C1-C4 alkyl, C2-C6 alkenyl, or hydroxy.

2. The compound according to claim 1, having the formula (Ia-2)

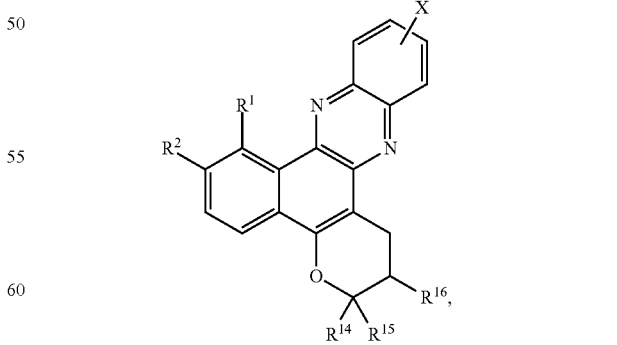

(Ia-2)

and pharmaceutically acceptable salts thereof.

3. The compound according to claim 1, having the formula (Ie-1), formula (Ie-2), formula (Ie-3), formula (Ie-4), formula (Ie-5), or formula (Ie-6):

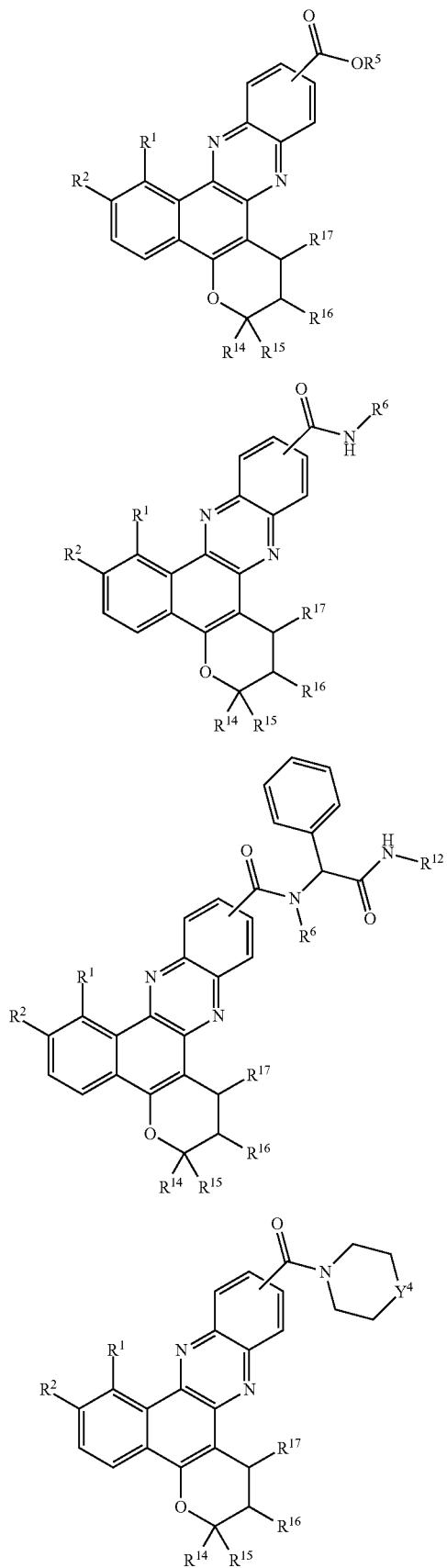
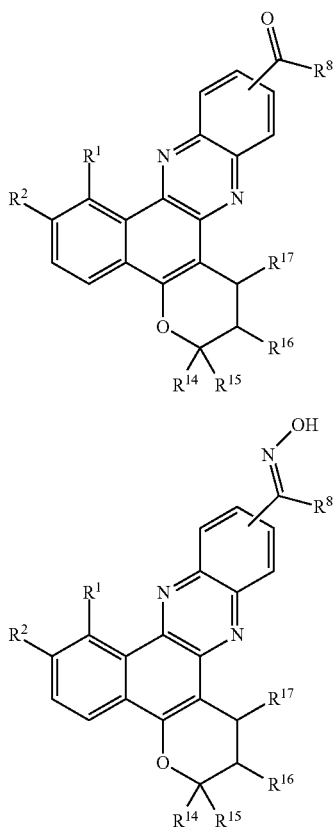
and pharmaceutically acceptable salts thereof,
wherein $Y^4$ is O, S, —CHOH or N—$R^{20}$ and $R^{20}$ is C1-C6 alkyl, 6-membered aryl, or 6-membered aralkyl.
4. The compound according to claim 1 and pharmaceutically acceptable salts thereof, wherein $R^1$, $R^2$, $R^3$, and $R^4$ are each H.
5. The compound according to claim 1 selected from the group consisting of:

163
5'
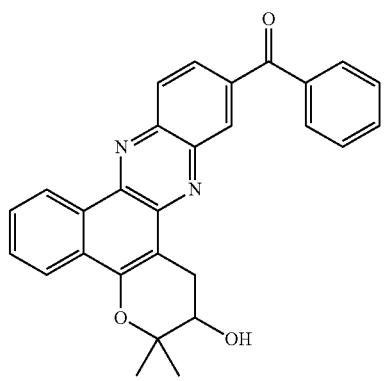
25
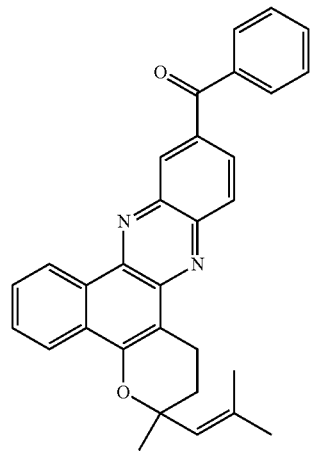
25'
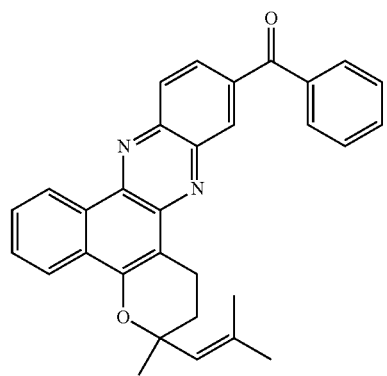
164
42
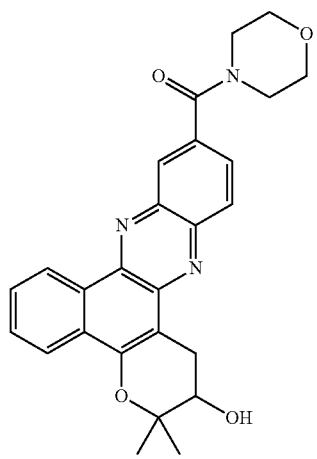
42'
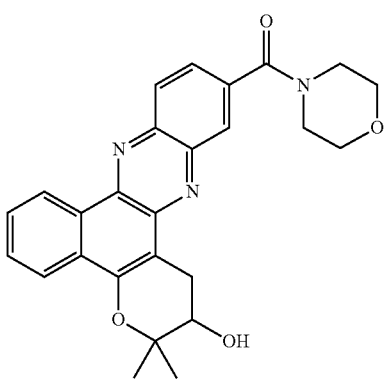
43
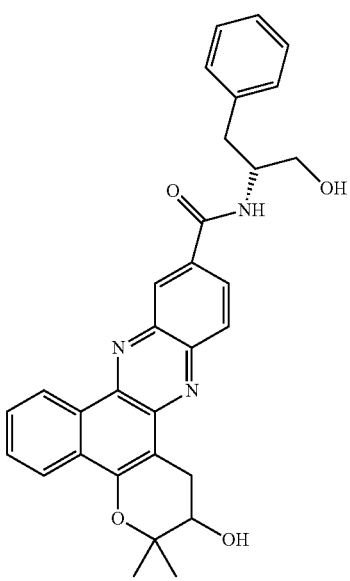

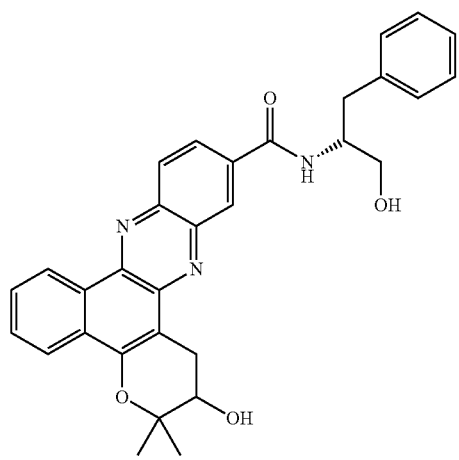
43'
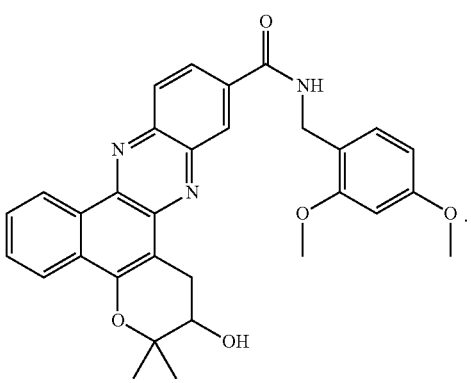
44'
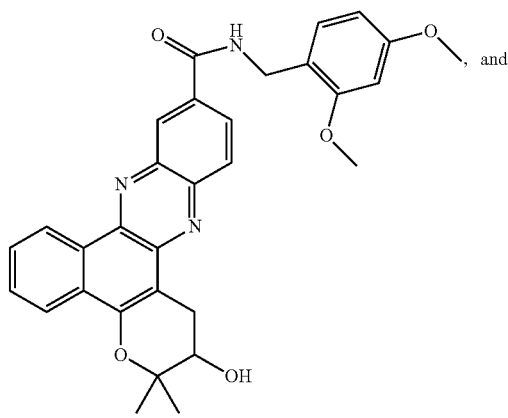
44 , and
6. A medicament comprising the compound according to claim 1 or a pharmaceutically acceptable salt thereof.
7. A pharmaceutical composition comprising the compound according to claim 1 or a pharmaceutically acceptable salt thereof and at least one pharmaceutically acceptable carrier, diluent, excipient and/or adjuvant.
* * * * *